United States Patent
Spence et al.

(10) Patent No.: US 6,190,397 B1
(45) Date of Patent: *Feb. 20, 2001

(54) MEANS AND METHOD FOR PERFORMING AN ANASTOMOSIS

(75) Inventors: Paul A. Spence, Louisville, KY (US); Warren P. Williamson, IV, Loveland, OH (US); George Christakis, Toronto (CA)

(73) Assignee: Origin Medsystems, Inc., Menlo Park, CA (US)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/325,457

(22) Filed: Jun. 3, 1999

Related U.S. Application Data

(62) Division of application No. 09/220,395, filed on Dec. 24, 1998, which is a continuation of application No. 08/714,615, filed on Sep. 16, 1996, now Pat. No. 5,868,763.

(51) Int. Cl.⁷ .................................................. A61B 17/04
(52) U.S. Cl. ........................... 606/153; 606/151; 623/12
(58) Field of Search ........................... 606/139, 151–155; 623/11, 12

(56) References Cited

U.S. PATENT DOCUMENTS

| | | |
|---|---|---|
| 3,166,072 | 1/1965 | Sullivan, Jr. . |
| 3,254,650 | 6/1966 | Collito . |
| 3,258,012 | 6/1966 | Nakayama et al. . |
| 3,606,888 | 9/1971 | Wilkinson . |
| 3,683,926 | 8/1972 | Suzuki ................................. 606/153 |
| 3,774,615 | 11/1973 | Lim et al. . |
| 3,908,662 | 9/1975 | Razgulov et al. . |
| 3,974,835 | 8/1976 | Hardy, Jr. . |
| 4,214,586 | 7/1980 | Mericle . |
| 4,214,587 | 7/1980 | Sakura ................................. 606/134 |
| 4,233,981 | 11/1980 | Schomacher . |
| 4,423,592 | 1/1984 | Daniel . |
| 4,474,181 | 10/1984 | Schenck . |
| 4,523,592 | 6/1985 | Daniel . |
| 4,657,019 | 4/1987 | Walsh et al. . |
| 4,676,245 | 6/1987 | Fukuda . |
| 4,747,407 | 5/1988 | Liu et al. . |
| 4,873,975 | 10/1989 | Walsh et al. . |
| 4,899,744 | 2/1990 | Fujitsuka et al. . |
| 4,930,502 | 6/1990 | Chen . |

(List continued on next page.)

FOREIGN PATENT DOCUMENTS

| | | |
|---|---|---|
| WO 95/17127 | 6/1995 | (WO) . |
| WO 95/17128 | 6/1995 | (WO) . |
| WO 95/35065 | 12/1995 | (WO) . |
| WO 98/02099 | 1/1998 | (WO) . |
| WO 98/19630 | 5/1998 | (WO) . |

OTHER PUBLICATIONS

C.A.F. Tulleken et al., "End–to–end anastomosis of small vessels using an ND:YAG laser with a hemispherical contact probe", Technical Note, J. Neurosurg., vol. 76, Mar. 1992, pp. 546–549.

*Primary Examiner*—Gary Jackson
(74) *Attorney, Agent, or Firm*—Limbach & Limbach, L.L.P.

(57) ABSTRACT

An anastomosis is performed using a mounting structure mounted on the outside of at least one vessels. The mounting structure includes a flexible mounting structure that is attached to the vessel by a special instrument. A graft vessel is attached to the mounting structure either directly or by means of another mounting structure attached to the graft vessel. Tools for attaching a mounting structure to a vessel are disclosed, and a tool for attaching two mounting structures together is also disclosed. Methods for carrying out the anastomosis according to the invention are also disclosed.

16 Claims, 40 Drawing Sheets

U.S. PATENT DOCUMENTS

| | | |
|---|---|---|
| 4,997,439 | 3/1991 | Chen . |
| 5,037,428 | 8/1991 | Picha et al. . |
| 5,089,008 | 2/1992 | Chen . |
| 5,123,908 | 6/1992 | Chen . |
| 5,188,638 | 2/1993 | Tzakis . |
| 5,234,447 | 8/1993 | Kaster et al. . |
| 5,250,057 | 10/1993 | Chen . |
| 5,263,973 | 11/1993 | Cook . |
| 5,336,233 | 8/1994 | Chen . |
| 5,366,462 | 11/1994 | Kaster et al. ......................... 606/153 |
| 5,403,333 | 4/1995 | Kaster et al. ......................... 606/153 |
| 5,486,187 | 1/1996 | Schenck . |
| 5,653,743 | 8/1997 | Martin ................................. 606/153 |
| 5,683,453 | 11/1997 | Palmaz ................................ 606/153 |
| 5,695,504 | 12/1997 | Gifford, III et al. ................ 606/153- |

SECTION B-B

SECTION A-A

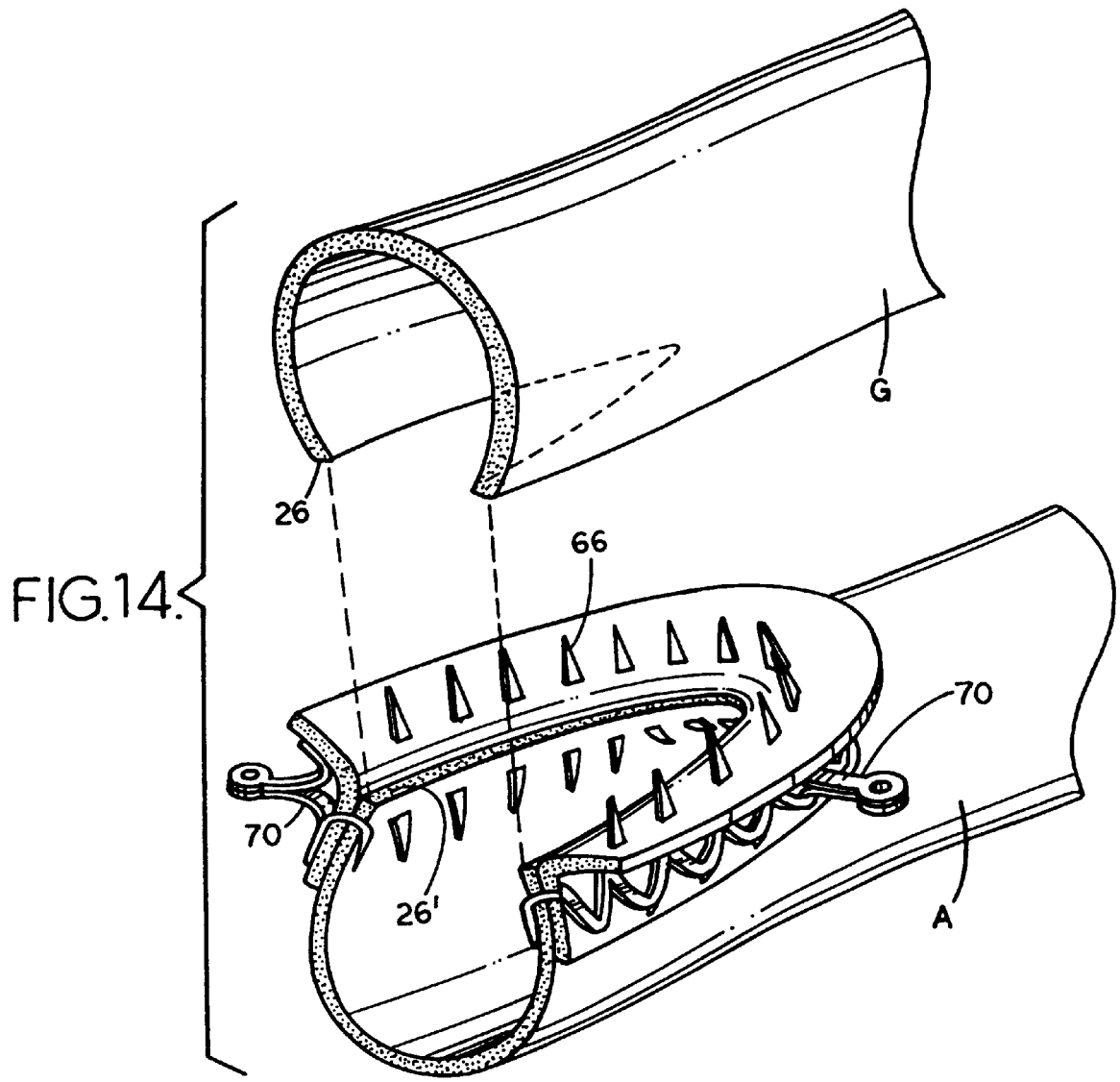

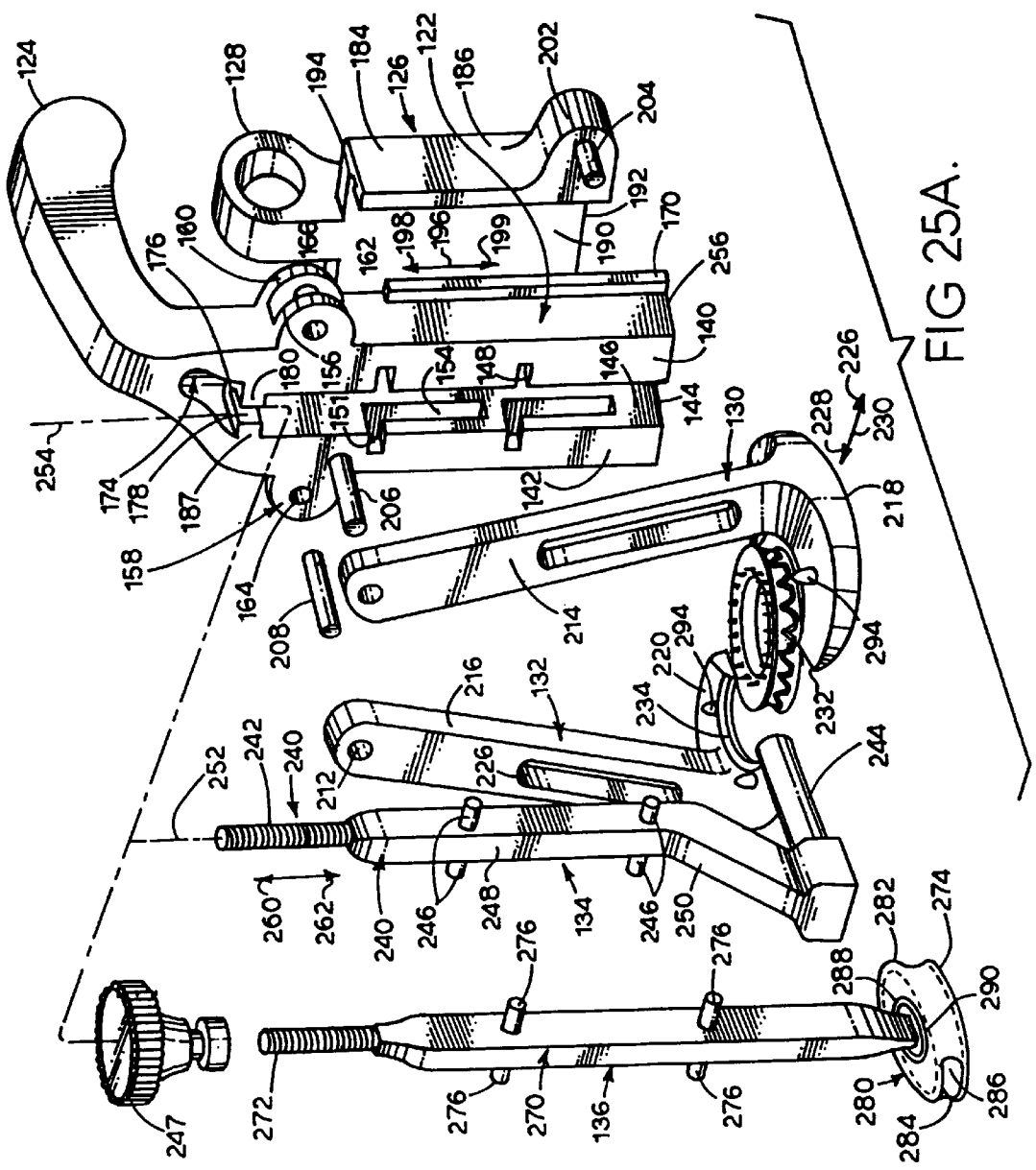

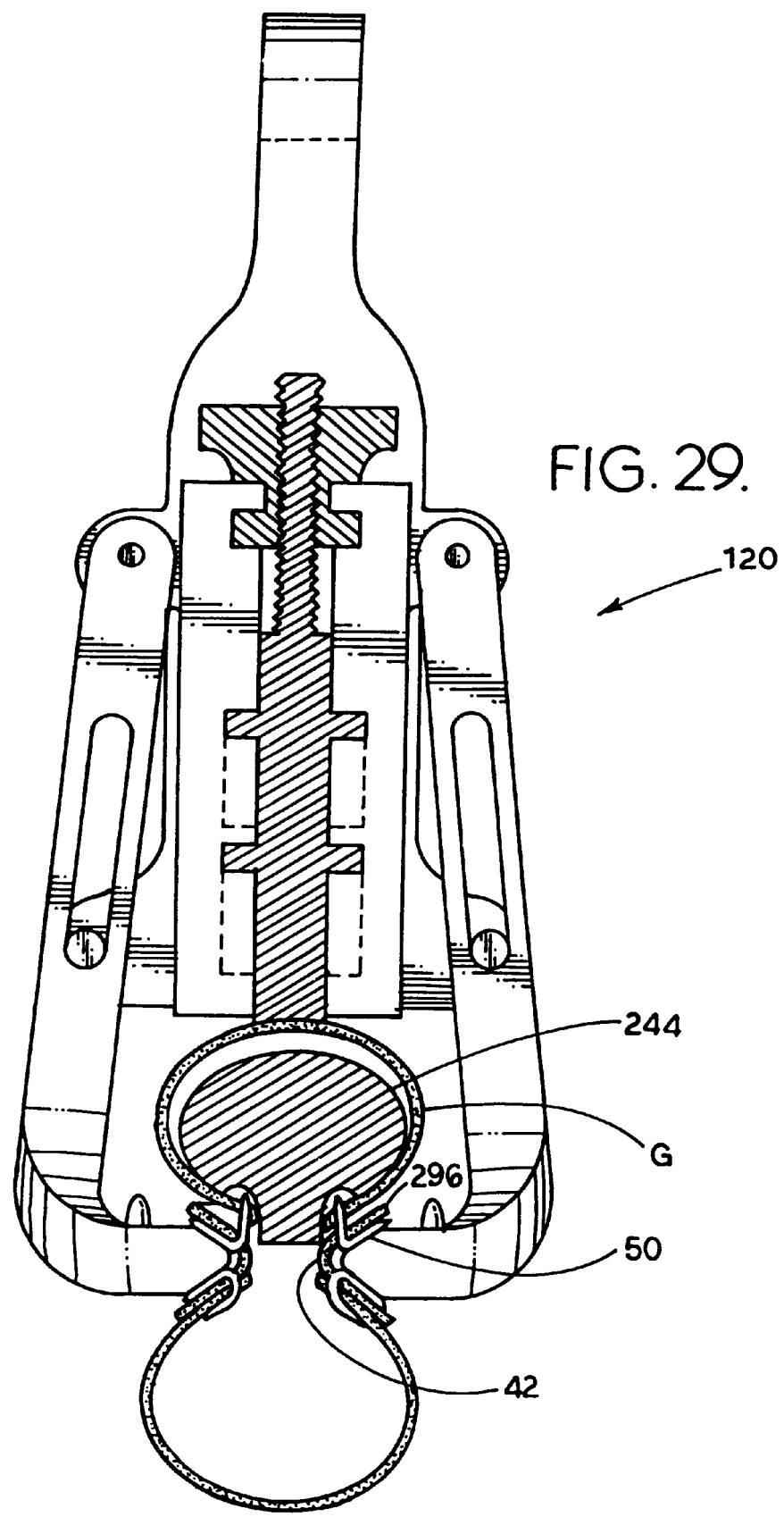

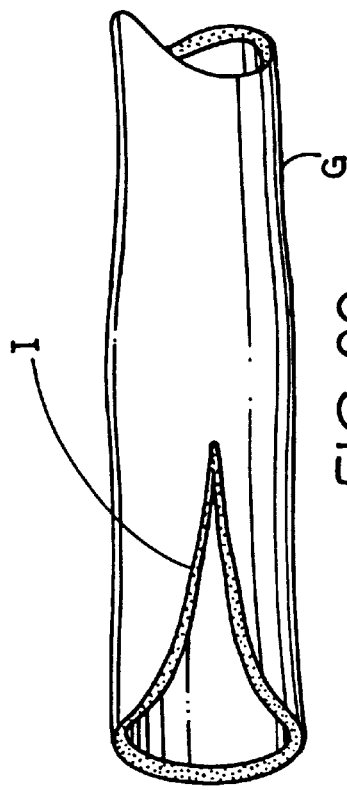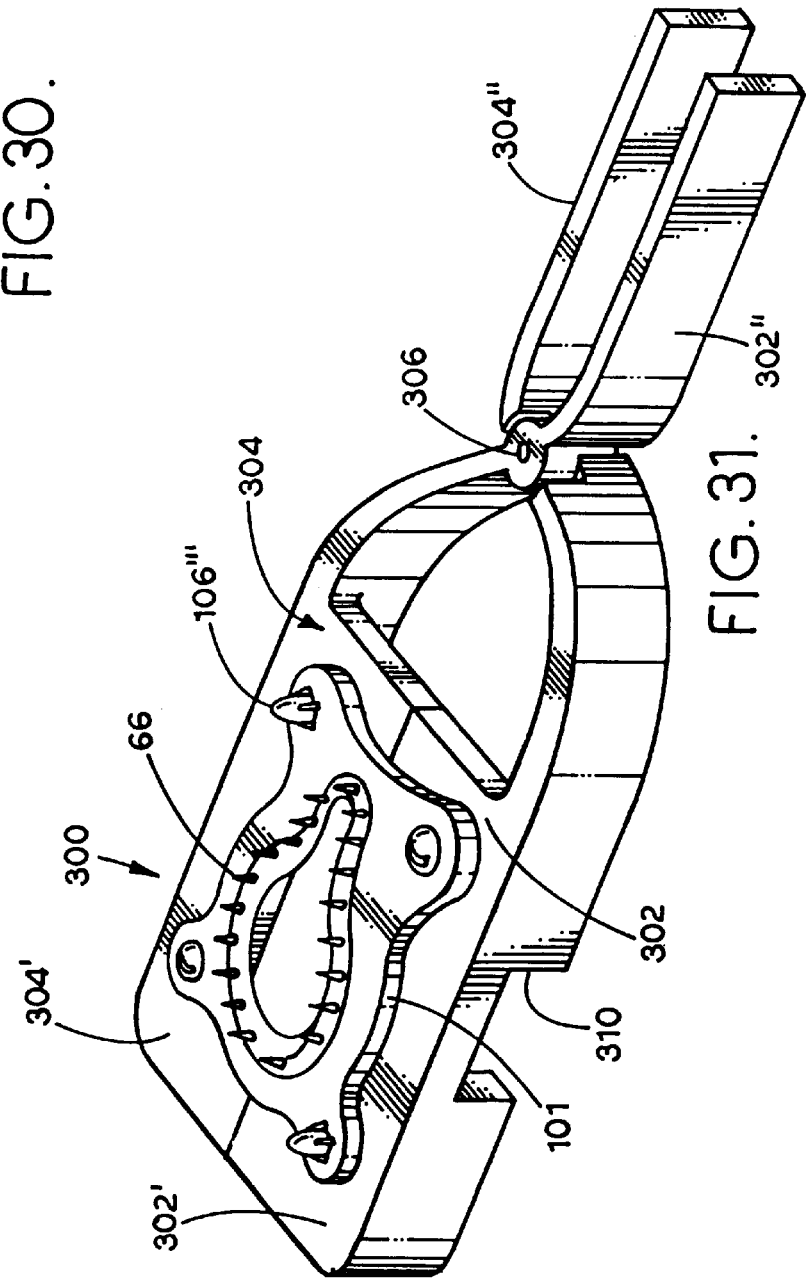

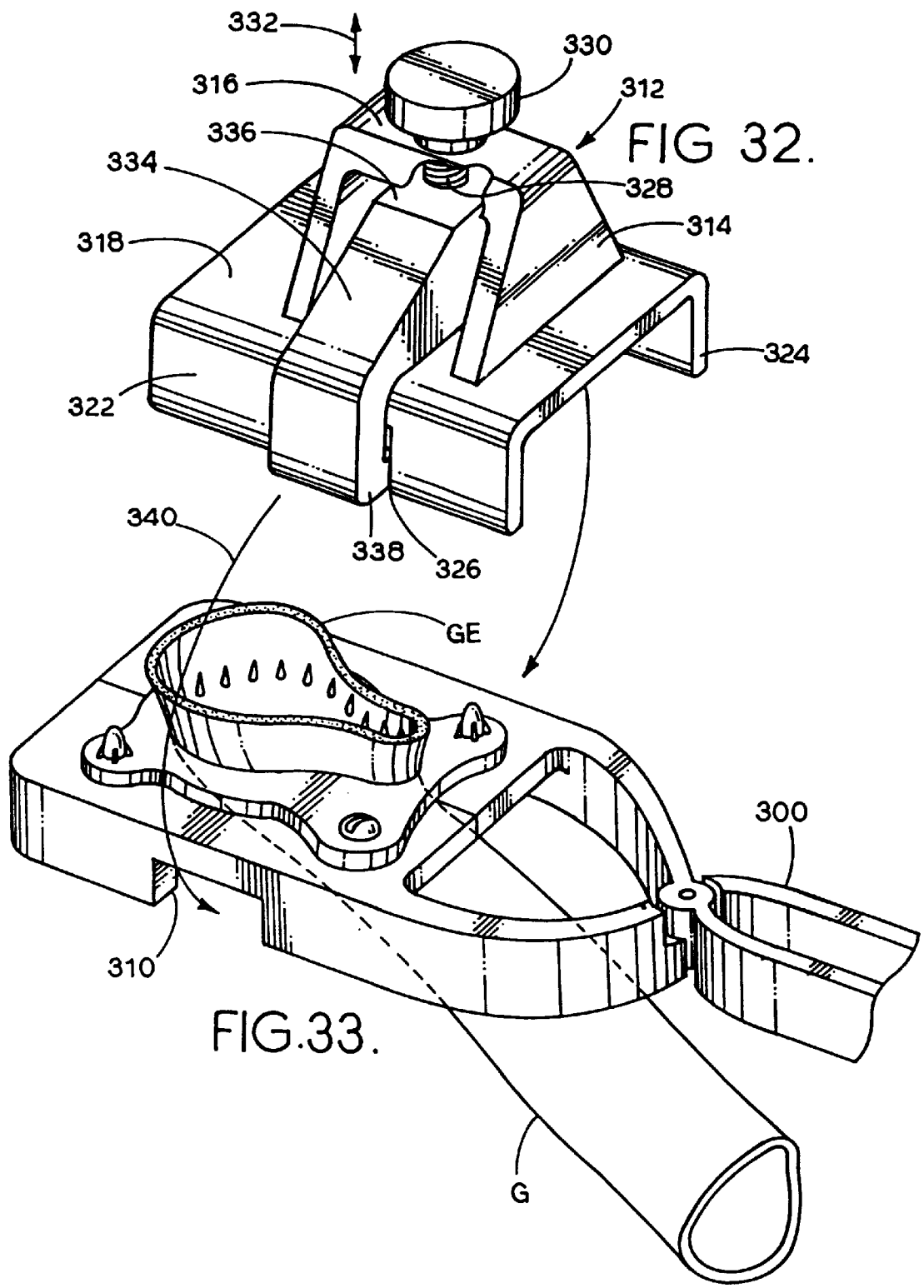

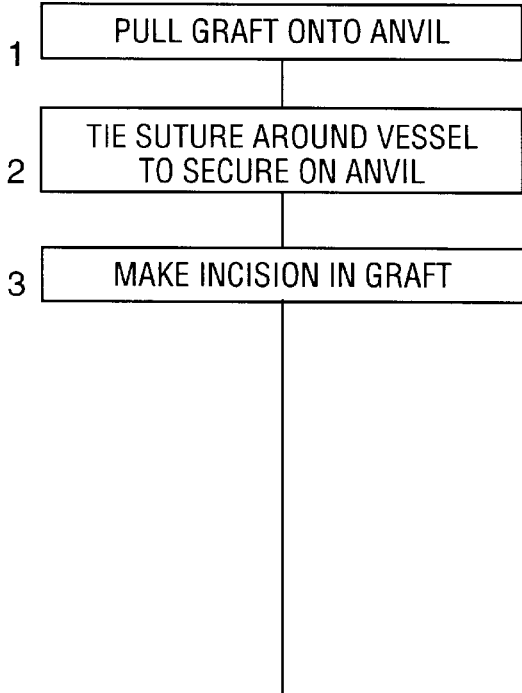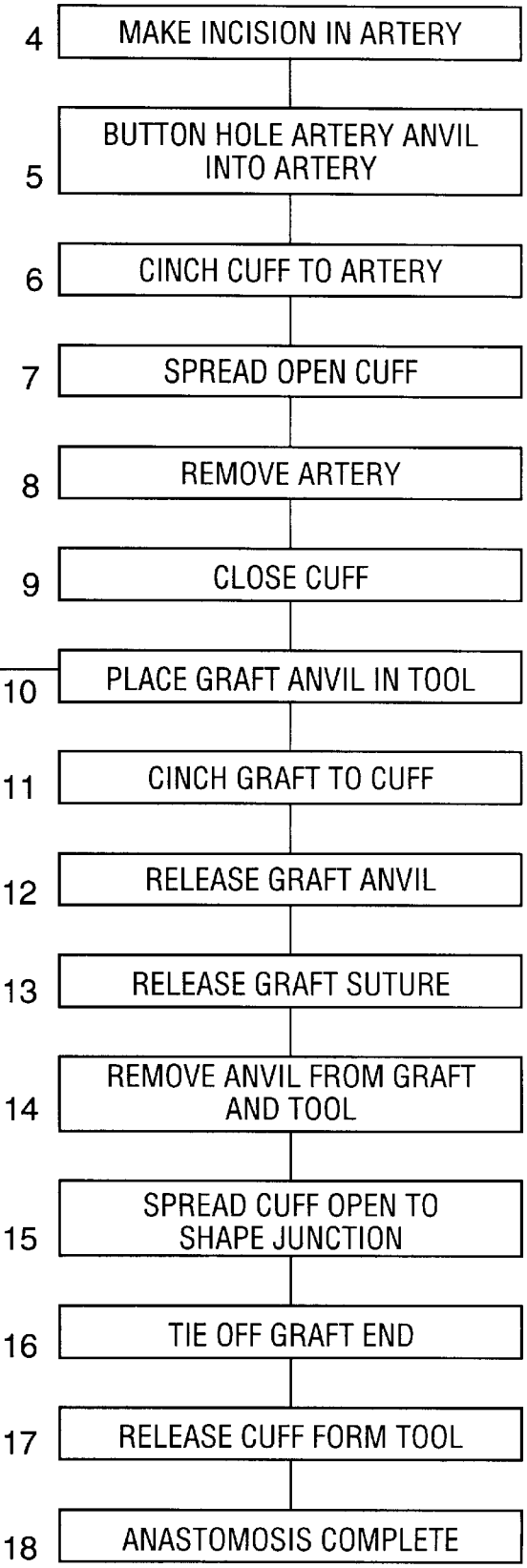
FIG. 41

MEANS AND METHOD FOR PERFORMING AN ANASTOMOSIS

This is a divisional of application Ser. No. 09/220,395, filed Dec. 24, 1998, pending, which in turn is a continuation of application Ser. No. 08/714,615, filed Sep. 16, 1996, now U.S. Pat. No. 5,868,763.

TECHNICAL FIELD OF THE INVENTION

The present invention relates to the general art of surgery, and to the particular field of means and methods associated with anastomoses.

BACKGROUND OF THE INVENTION

In the United States, there are currently as many as 300,000 coronary artery bypass graft (CABG) procedures performed on patients annually. Each of these procedures may include one or more graft vessels which are hand sutured. Until recently, coronary artery bypass procedures have been performed with the patients on cardiopulmonary bypass whereby the heart is stopped with cardioplegia and the surgery is performed on an exposed, stationary heart.

The vast majority of CABG procedures performed currently are accomplished by opening the chest wall to gain access to the coronary vessels. Through the use of heart lung bypass machines and a drug to protect the heart muscle, the heart is stopped and remains still during the procedure. In this setting, the surgeon has ample time and access to the vessels to manipulate hand suturing instruments such as forceps, needle holders and retractors.

However, with increasing costs of hospital stays and increased awareness by patients of other minimally invasive surgical procedures, interest in developing a minimally invasive CABG procedure is increasing. Hospitals need to reduce costs of procedures and patients would like less post-operative pain and speedier recovery times.

In the past, two significant developments in the technology played a major role in advancing the whole area of cardiac surgery. The heart-lung machine was invented in the 1950's but underwent significant improvement in design to become a reliable clinical device in the 1960's. The heat-lung machine allows the surgeon to take the heart out of the blood circulation system to work on it in isolation.

The second major development was in myocardial protection. When the heart was isolated from the circulation, it was no longer perfused. After twenty to thirty minutes of ischemia, irreparable damage occurred and no matter how good the repair, the heart function was frequently inadequate to allow the patient to survive. Cardioplegia, a solution which is generally cold and high in potassium, changed everything. This development occurred in the 1970's. This allowed very satisfactory protection of the heart so the surgeon could perform an unhurried repair and still expect the heart to work afterward.

A secondary consequence of these developments was the decline in interest in technology to facilitate heart surgery. When speed of the surgery was initially of utmost importance, all sorts of developments were proposed to speed surgery. Therefore, the art in the 1960's and 1970's contained numerous examples of such devices.

Now with an increased incentive to reduce costs, there is a renewed interest in redesigning cardiothoracic procedures. A few pioneering surgeons are now performing minimally invasive procedures whereby the coronary artery bypass is performed through a small incision in the chest wall. There are some surgeons that believe that the best way to perform a minimally invasive coronary artery bypass procedure is to perform the procedure on a beating heart, i.e., without heart-lung bypass and cardioplegia. This minimizes the time it takes to perform the procedure and reduces the cost of the operation by eliminating the heart lung bypass machine.

In the case of minimally invasive procedures on a beating heart, the surgeon starts by making a mini-thoracotomy between the fourth and fifth ribs and, sometimes, removing the sternal cartilage between the fourth or fifth rib and the sternum. The space between the fourth and fifth ribs is then spread to gain access to the internal mammary artery (IMA) which is dissected from the wall of the chest. After dissection, it is used as the blood supply graft to the left anterior descending artery of the heart (LAD). Below the IMA lies the pericardium and the heart. The pericardium is opened exposing the heart. At this point, the LAD may be dissected from the fissure of the heart and suspended up with soft ligatures to isolate the artery from the beating heart. Some companies are making a special retractor to gently apply pressure to the heart muscle to damp the movement right at the LAD. A small arteriotomy is performed in the LAD and the graft IMA is sutured to the LAD.

Traditionally, to gain access to the cardiac vessels to perform this procedure the sternum is sawn in half and the chest wall is separated. Although this procedure is well perfected the patient suffers intense pain and a long recovery.

Until recently all bypass graft procedures have been performed by hand suturing the tiny vessels together with extremely fine sutures under magnification. The skills and instruments required to sew extremely thin fragile vessel walls together have been perfected over the last twenty years and are well known to the surgical community that performs these procedures.

In the 'open chest' surgical setting, the surgeon has adequate access and vision of the surgical site to manipulate the anatomy and instruments.

The push for less invasive surgical approaches is fueling interest in many areas that were abandoned long ago—including that of coronary fastening and valve replacement. The inventors have thus identified a need for a device and a method to perform CABG surgery on a beating heart.

Some surgeons are attempting minimally invasive CABG procedures using femoral artery bypass access rather than opening the chest for bypass via the aorta. However, since use of cardioplegia requires additional support and expense during the anastomosis procedure, the inventors believe that it is best to attempt to fasten the anastomosis while the heart is beating. However, this procedure when performed with a hand suturing technique is very imprecise due to the translation of movement from the beating heart to the suspended artery. This may cause imprecise placement of the suture needles. Any imprecise placement of the sutures may cause a distortion of the anastomosis which may cause stenosis at this junction. The sutures used for this procedure are extremely fine (0.001" in diameter) and are placed less than 1 mm apart.

As one can imagine it is difficult enough to place suture needles the size of a small eyelash into a vessel wall with placement accuracy of better than 1 mm. To accomplish this feat of precision on a moving target is extremely difficult. To make matters worse, the site is often bloody due to the fact that the heart has not been stopped.

Therefore, there is a need for a means and method which permits the forming of a precise anastomosis without requiring the stopping of a beating heart. Still further, there is a need for performing such an anastomosis in a minimally invasive manner.

The current method of hand suturing is inadequate for the following reasons:

On a beating heart it may be difficult to place the sutures with the position precision required. In a beating heart procedure the surgeon can attempt to minimize the deleterious effects of the movement by using suspension or retraction techniques. However, it is impossible to isolate all movement of the vessel during an anastomosis procedure.

Methods that attempt to stabilize and isolate the artery from the movement of the beating heart can damage the vessel or cause myocardial injury (MI).

In addition to the problem of placing sutures accurately one must make an incision through the artery wall to open the artery. This too is a delicate procedure even on a still heart because the incision must be of a precise length. It is also critical to not penetrate the back wall or side wall of the vessel which will lead to complications. The placement of the initial incision is of paramount importance. The surgeon must pick a suitable location free from calcium deposits, fat and side branches.

Without cardioplegia, one must also provide blood flow to the heart muscle while the heart is beating, therefore, after the initial arteriotomy, the surgical field is very bloody and obscured.

Access to the heart vessels other than the LAD will be extremely difficult with minimally invasive hand suturing due to the anatomical location of the posterior wall of the heart.

Although minimally invasive CABG procedures are taking place now with sutured anastomosis they require superlative skills and are therefore not widely practiced.

One of the most vexing problems is that of adequate access. The procedure takes place through an access site created between two ribs. The ribs cannot be spread too far without risk of breaking and the heart lies deep within the chest. The access is through a small, long, dark tunnel. The surgeon must then manipulate his tools down this tunnel without obscuring his vision.

If special tools are constructed to allow the surgeon to be able to hold suture needles on the end of a long instrument, the added length of the tool only amplifies any inaccurate manipulation. The same holds true for any special suturing devices contemplated.

If the sutures are not placed correctly in the vessel walls, bunching or leaks will occur. In the minimally invasive procedure this is disastrous, usually resulting in the conversion to an open chest procedure to correct the mistake. Any rough handling of the vessel walls is detrimental as inflammation can cause further postoperative complications.

The anastomosis must seal leak tight to prevent exsanguination. Therefore, any improvement over sutures must provide a leak free seal in a very confined space, yet should provide proper flow areas in the vessel after healing is complete.

As is apparent from the above discussion, it is necessary to find a way to control the beating heart movement of the vessel while performing the anastomosis in such a way that still allows for exact placement of the fastening means.

While the art contains disclosures of several devices that are used to join blood vessels, these devices are primarily directed to an end-to-end anastomosis, which is inadequate for CABG procedures. Furthermore, the techniques disclosed in the prior art often require the vessels to be severely deformed during the procedure. The deformation may be required to fit the vessels together or to fit a vessel to an anchoring device. One cannot just slit the tissue and pull it through a ring to anchor it on a flange. Pulling or stretching the vessel walls produces a very unpleasant and unexpected result. Vessel walls are made of tissue fibers that run in the radial direction in one layer and the longitudinal direction in another layer. In addition the elasticity of the tissue fibers in the longitudinal direction is greater than those that run radially. Therefore, the tissue will not stretch as easily in the radial or circumferential direction and results in a narrowing or restriction when pulled or stretched in the prior art devices. Vessel walls also have a layer of smooth muscle cells that can spasm if treated harshly. Such manhandling will result in restrictions and stenotic junctions because the vessel walls will react poorly to being treated in such a rough manner and the stretching of the vessel wall will telegraph up the vessel wall due to the high radial stiffness of the vessel structure, causing restrictions and spasms in the vessel wall. The prior art fails to teach that the vessels are living tissue and must not be made to conform to rigid fitting-like shapes. Therefore, there is a need for an anastomotic technique that permits handling of blood vessels in a manner that is not likely to cause those blood vessels to react poorly.

Additionally, prior art systems fail to teach methods of ensuring hemostasis so as not to have leakage under pressure. It is noted that mechanical devices used to join blood vessels are extremely difficult to seal. No attempt has been made in the prior art to include a hemostatic medium in conjunction with an anastomotic device. Prior art devices are directed to accomplishing hemostasis through excessive clamping forces between clamping surfaces or stretching over over-sized fittings.

In order to effect good healing, healthy vessel walls must be brought into intimate approximation. This intimate approximation is now accomplished by the skilled hands of a surgeon with sutures. A vascular surgeon is taught how to suture by bringing the vessel edges together with just the right knot tightness. Too loose and the wound will leak and have trouble healing causing excessive scar tissue to form. Too tight will tear through the delicate tissue at the suture hole causing leaks. The key is to bring the edges together with just the right amount of intimate approximation without excessive compression.

It must be further noted that the junctions taught in the prior art are not anatomically correct both for blood flow and for healing. A well made anastomotic junction is not made in a single plane and should accurately follow blood vessel geometry. The junction is more of a saddle shape, and the cross section is not necessarily a circle. The junction where the vessel units join is not a constant cross section angle, but an angle that varies continuously throughout with respect to any linear reference. In addition, the length of the junction should be many times the width of the opening in order to assure a low blood flow pressure gradient in the junction and to assure a proper flow area. In fact, the best results are obtained if the confluence area is actually oversized. The prior art junctions do not account for such flow characteristics and parameters and are thus deficient. Therefore, there is a need for an anastomotic technique which can establish proper flow characteristics and parameters and that accurately preserves blood vessel geometry, specifically the plural planar nature in which the junction occurs. Furthermore, most anastomoses are made between vessels that are not similar in size. It is therefore necessary to provide a means and method which allow for the accommodation and joining of dissimilarly sized vessels.

In addition, the inventors have found through post surgical follow-up that the supply vessels grow in diameter to accommodate their new role in providing oxygenated blood to the heart; therefore, there is a need to provide an oversized junction to accommodate any increase in the dimension of the graft vessel size. With a rigid ring that is a singular circular cross section of the graft, the fitting does not allow the vessel to provide this increase in flow as the vessels expand to meet the needs of the heart muscle. Still further, the inside lining of the vessel walls (intima) should make contact with each other to have proper healing. The walls of the vessels must come together with just the right amount of approximation to promote good healing. If the incised edges are too far apart scarring will occur causing restrictions. The walls cannot be compressed between two hard surfaces which will damage the vessels. The prior art teaches plumbing-like fittings clamped onto vascular structures. However, clamping and compressing the vessel walls too tightly will cause necrosis of the vessel between the clamps. If necrosis occurs the dead tissue will become weak and most likely cause a failure of the joint. Still further such rings and tubes used to clamp vessels together do not follow the correct anatomical contours to create an unrestricted anastomosis. Failing to account for the way healing of this type of junction occurs, and not accounting for the actual situation may cause a poor result. A suture technique has the advantage of having the surgeon making on-the-fly decisions to add an extra suture if needed to stop a leak in the anastomosis. In a mechanical minimally invasive system it will not be possible to put an 'extra suture throw' in so the system must provide a way to assure complete hemostasis. Being a mechanical system the approximation will not be 100% perfect. And since the design errs on the side of not over-compressing the tissue there may be very small areas that may present a leak between the edges of the vessel walls. Accordingly healing with prior art techniques using mechanical joining means is not as efficient as it could be. Therefore, there is a need for an anastomotic technique that accounts for the way healing actually occurs and provides proper structural support during the healing process.

When vascular integrity is interrupted the body quickly reacts to reestablish hemostasis. Circulating blood platelets are quickly mobilized to the injury site and initiate and support the coagulation sequence that leads to the formation of a fibrin plug at the site of injury. Large breaks in vessel walls which are under pressure cannot be effectively sealed by platelets and fibrin without a substrate to collect on. It is critical that the junction of an anastomosis bring two healthy vessel surfaces in close approximation to provide an optimal region for vessel repair and healing, minimizing the distance between healthy endothelial cells on either side of the junction. This allows for the natural control processes which prevent platelet aggregation from extending beyond the area of injury. A more detailed description of the clot limiting process and the healing process can be found in various reference texts, such as "Coagulation: The Essentials", by Fischbach, David P and Fogdall, Richard P, published by Williams and Wilkins of Baltimore in 1981, the disclosure of Chapter 1 thereof being is incorporated herein by reference.

Still further, some vessels are located or sized in a manner that makes placing elements thereon difficult. In such a case, the fewer elements used to perform an anastomosis the better. Therefore, there is a need for a means and a method for. performing an anastomosis that can be effected without the need of a hemostatic medium.

Many times when a CABG operation is undertaken, the patient has multiple clogged arteries. At the present time, the average number of grafts is 3.5 per operation. When multiple grafts are performed, there is sometimes the opportunity to use an existing or newly added supply vessel or conduit for more than one bypass graft. This is known as a jump graft, whereby the conduit, at the distal end thereof is terminated in a side-to-side anastomosis first, with an additional length of conduit left beyond the first junction. Then, an end of the conduit is terminated in an end-to-end junction. This saves time and resources and may be necessary if only short sections or a limited amount of host graft material is available.

At the present time, existing means and methods of performing an anastomosis do not permit the formation of multiple anastomotic sites on a single graft vessel such as at both proximal and distal ends. Thus a surgeon will have to use multiple tools to perform multiple anastomoses. This will be either impossible or very expensive.

Therefore, there is a need for a means and a method for performing an anastomosis which will lend itself to efficient and cost-effective multiple by-pass techniques.

Therefore, there is also a need for a means and a method for performing an anastomosis which will lend itself to efficient and cost-effective jump graft techniques.

As discussed above, performing a sutured anastomosis in a minimally invasive manner while the patient's heart is beating requires an extremely high degree of dexterity. Any instrument used in such a procedure must therefore be as easy and efficient to use as possible whereby a surgeon can focus most of his attention on the anastomosis site. The instrument should thus reflect the above-discussed needs as well.

Still further, any instrument used in such a procedure must be amenable to efficient manufacture.

OBJECTS OF THE INVENTION

It is a main object of the present invention to provide a means and method of performing an anastomosis without stopping the patient's heart.

It is also an object of the present invention to provide an instrument which can be used to efficiently, accurately and effectively form a proper anatomically correct anastomosis.

It is another object of the present invention to provide an instrument which can be used to efficiently, accurately and effectively form a proper anastomosis without stopping the patient's heart.

It is another object of the present invention to provide a means and method of performing an anastomosis without stopping the patient's heart in a minimally invasive manner.

It is another object of the present invention to provide a means and method of performing an anastomosis without stopping the patient's heart in a minimally invasive manner in which the blood vessels are joined together in such a way as to most efficiently promote healing.

It is another object of the present invention to provide a means and method of performing an anastomosis without stopping the patient's heart in a minimally invasive manner in which the blood vessels are joined together without squeezing, compressing or otherwise manhandling them.

It is another object of the present invention to provide a method and means to stabilize a vessel while performing an anastomotic procedure.

It is another object of the present invention to provide a means and method of performing an anastomosis without stopping the patient's heart in a minimally invasive manner in which the blood vessels are joined together to form a confluence area that accurately accounts for flow characteristics and flow parameters.

It is another object of the present invention to provide a means and method of performing an anastomosis without stopping the patient's heart in a minimally invasive manner in which blood vessels can be joined together in a side-to-side configuration.

It is another object of the present invention to provide a means and method of performing an anastomosis without stopping the patient's heart in a minimally invasive manner in which blood vessels can be joined together in an end-to-side configuration.

It is another object of the present invention to provide a means and method of performing an anastomosis without stopping the patient's heart in a minimally invasive manner in which blood vessels can be joined together to form a junction that is anatomically correct and accurately reflects blood vessel geometry at the junction.

It is another object of the present invention to reduce tissue inflammation and necrosis due to mishandling and over compression.

It is another object of the present invention to provide a means to hold the edges of the vessel walls in close approximation to promote healing with a minimum of scarring.

It is another object of the present invention to provide an anastomotic stapling device that provides blood flow to the heart while making the anastomosis.

It is another object of the invention to provide an anastomotic stapling device that obviates bunching of the tissue due to imprecise placement of fasteners.

It is another object of the invention to provide an anastomotic device that is amenable to efficient manufacture.

It is another object of the present invention to provide an anastomotic means and method which can join dissimilarly sized vessels.

It is another object of the present invention to provide an anastomotic means and method which will accommodate joining vessel walls at a junction angle that varies with respect to a reference line.

It is another object of the present invention to provide an anastomotic means and method that has a living hinge at a junction site.

It is another object of the present invention to provide an anastomotic means and method which can effect a junction without a hemostatic medium.

It is another object of the present invention to provide an anastomotic means and method which can be used in proximal junctions and in multiple anastomotic sites on the same vessel.

It is another object of the present invention to provide an anastomotic means and method which can be used in a means and a method for performing an anastomosis which will lend itself to efficient and cost-effective multiple by-pass techniques.

It is another object of the present invention to provide an anastomotic means and method which can be used in a means and a method for performing an anastomosis which will lend itself to efficient and cost-effective jump graft techniques.

It is another object of the present invention to provide an anastomotic means and method which is especially well suited for all types of blood vessel anastomosis procedures and techniques, such as, but not limited to, proximal, side-to-side, end-to-side, jump grafts as well as others that will occur to those skilled in the art based on the teaching of the present disclosure.

SUMMARY OF THE INVENTION

When a patient shows symptoms of cardiac insufficiency which are not severe enough to warrant surgical intervention, the cardiologist is called on to clean out or open up the clogged arteries. One way to open the artery is to install an internal stent such as disclosed in U.S. Pat. No. 5,425,739. This stent is a prop that is most often configured like a cylindrical cage. The stent is delivered to the site over a balloon catheter. When in place, the catheter is inflated, expanding the stent which in turn holds or props open the narrowed artery. Since the stent is made of a material that has no material memory, it will retain the shape determined by the inflation of the balloon. The balloon is removed from the artery and the stent stays inside the artery. Such memoryless material is suitable for use for a bridge and for the stiffening framework discussed above.

The present invention uses a similar concept, however, the "stent" is external to the blood vessel wall. It has the similar function of holding the vessels open, but is also used as the means for joining the vessels. The external "stent" is the cuff discussed above.

The above-mentioned objects, as well as additional objects as will occur to one skilled in the art based on the teaching of the present disclosure, are achieved by a minimally invasive means and method for forming a precise and anatomically accurate anastomosis on a patient without requiring the patient's heart to be stopped using an instrument that precisely places fasteners on the outside surface of a blood vessel in a position to cause the anastomosis to have a proper flow area and to accurately reflect the geometry of the junction and which positions the inside edges of the incised blood vessels in abutting contact with each other whereby proper healing is promoted. The means and method of the present invention also provide the ability to create an oversized junction which will accommodate future anticipated growth of the vessels. The means and method of the present invention accomplish this without requiring the mishandling of the blood vessels, and can be used for side-to-side anastomoses as well as end-to-end anastomoses. The device is also amenable to efficient manufacture.

In addition, these objects are accomplished by providing a flexible hemostatic medium to hold a malleable stiffening framework. The hemostatic media can be absorbable material or a fabric material that allows tissue ingrowth. The medium provides a supportive surface at the edges of the anastomosis for the natural vessel repair process.

Therefore, to address the need of hemostasis, the inventors have included a cuff material which can be made from a variety of materials to allow the anastomosis to perform in a leak free manner with the proper substrate for healing to occur. It is also anticipated that through more development, a special coating such as collagen coatings could be incorporated into the hemostatic medium to encourage tissue ingrowth, and to discourage excessive thrombosis. Such coatings and treatments will occur to those skilled in the art based on the teaching of the present disclosure. It is further anticipated that research will suggest that these media may be absorbable or made from non-woven fabrics, or combinations of both.

It is therefore shown that the use of a hemostatic medium is a novel approach to providing a complete minimally invasive anastomotic device which does not use excessive clamping forces.

Although a hemostatic material is shown in the preferred embodiment as a woven synthetic cuff, those skilled in the art will be taught by this disclosure to substitute other materials without departing from the scope of the present invention. The term "cuff" can be used to describe a form of hemostatic medium but is not meant to be limiting.

The means and method places one or more configurations of hemostatic medium on the outside surface of blood vessels being joined with the inner edges of the media spaced from the edges of an incision made in the blood vessel at a distance so no evagination of the vessel occurs and no gapping occurs during the healing process. Each cuff is flexible and can be shaped to match the blood vessel at the junction site. When the cuff or cuffs are closed, the blood vessels are drawn together in a manner which places the inside edge of each of the blood vessels adjacent to the incisions in abutting contact with each other whereby proper healing can occur without unduly contorting the blood vessels. The cuff, or cuffs, have a means which permit each cuff to be shaped and to retain the set shape whereby the cuff accurately matches the blood vessel shape and the junction can be shaped to establish the most efficient flow conditions.

The present invention can be used to provide an oversized confluence area so the change in size of the blood vessel to provide oxygenated flow to the heart can be accommodated. This is done by providing a fastener that allows for an oversized length junction and the ability to size and shape the junction after the two vessels are attached to assure a wide cross-sectional opening between the vessels. Mechanical fasteners or sutures can be used to mount the cuff on the blood vessels. The procedure can be performed while permitting virtually uninterrupted blood flow.

The instrument used to attach the cuffs to the blood vessels includes a main body which is adapted to accommodate anvils for both graft vessels and arteries. The device includes a cuff engaging means for engaging a cuff to attach the cuff to the blood vessel and to adjust the shape of the cuff to accurately reflect the shape of the junction. A linkage connects the cuff engaging means to an operating element so a surgeon can easily operate the device. One of the anvils is received in a graft vessel and the other anvil is received in the artery to which the graft vessel is to be attached. The artery accommodated anvil includes a blood passage defining portion so blood can continue to flow through the artery during the procedure. Furthermore, the instrument stabilizes the vessel from the beating heart. The artery accommodated anvil is actually larger than the incision in the artery and is "button holed" into the artery via the incision. Once in place in the artery the surgeon can pull up on the vessel at the incision thereby moving the work area in conjunction with the vessel and isolating the work surface from the beating heart. This makes the cuff fastening accurate and precise. Also, it assures that the tool and the vessel are moving together to isolate the beating heart movement from the tool.

The device engages the cuff and not the blood vessel so shaping and movement occurs while applying only minimal and gentle pressure to the blood vessels. This permits the junction to be properly and fully customized without mishandling the blood vessels. The instrument also has guides for forming the fasteners or staples.

As can be understood from the foregoing, and as one skilled in the art will be able to understand from the teaching of the present disclosure, the means and method of the present invention can be applied to multiple grafts and to jump grafts thereby making such techniques possible and cost effective.

While the means and method embodied in the present invention is especially suited for beating heart surgery, it may also be utilized for minimally invasive procedures that use cardioplegia as well as standard "open chest" procedures due to its novel time saving and precision features.

BRIEF DESCRIPTION OF THE DRAWING FIGURES

FIGS. 3, 4, 5A, 5B, and 6–9 illustrate prior art means and methods of performing an anastomosis.

Figure 10:
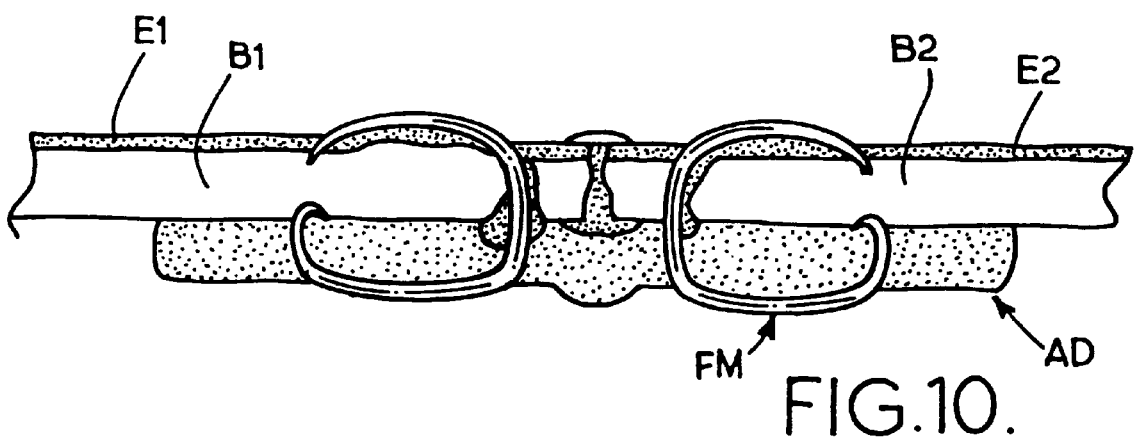

FIG. 10 illustrates the principle of the present invention in which an anastomosis includes a hemostatic medium located in such a manner that clots will form externally of the blood vessel.

Figure 11:
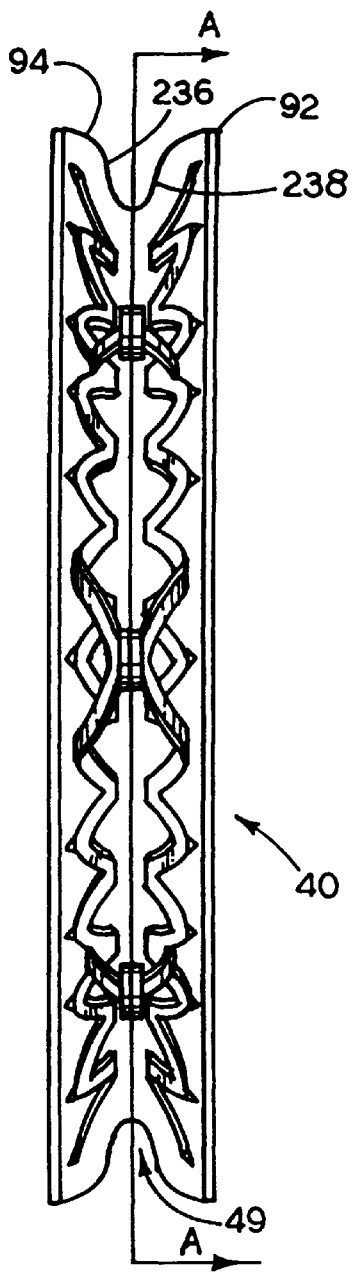

FIG. 11 is a side view of a cuff which is included in the means for performing an anastomosis according to the present invention.

Figure 11A:
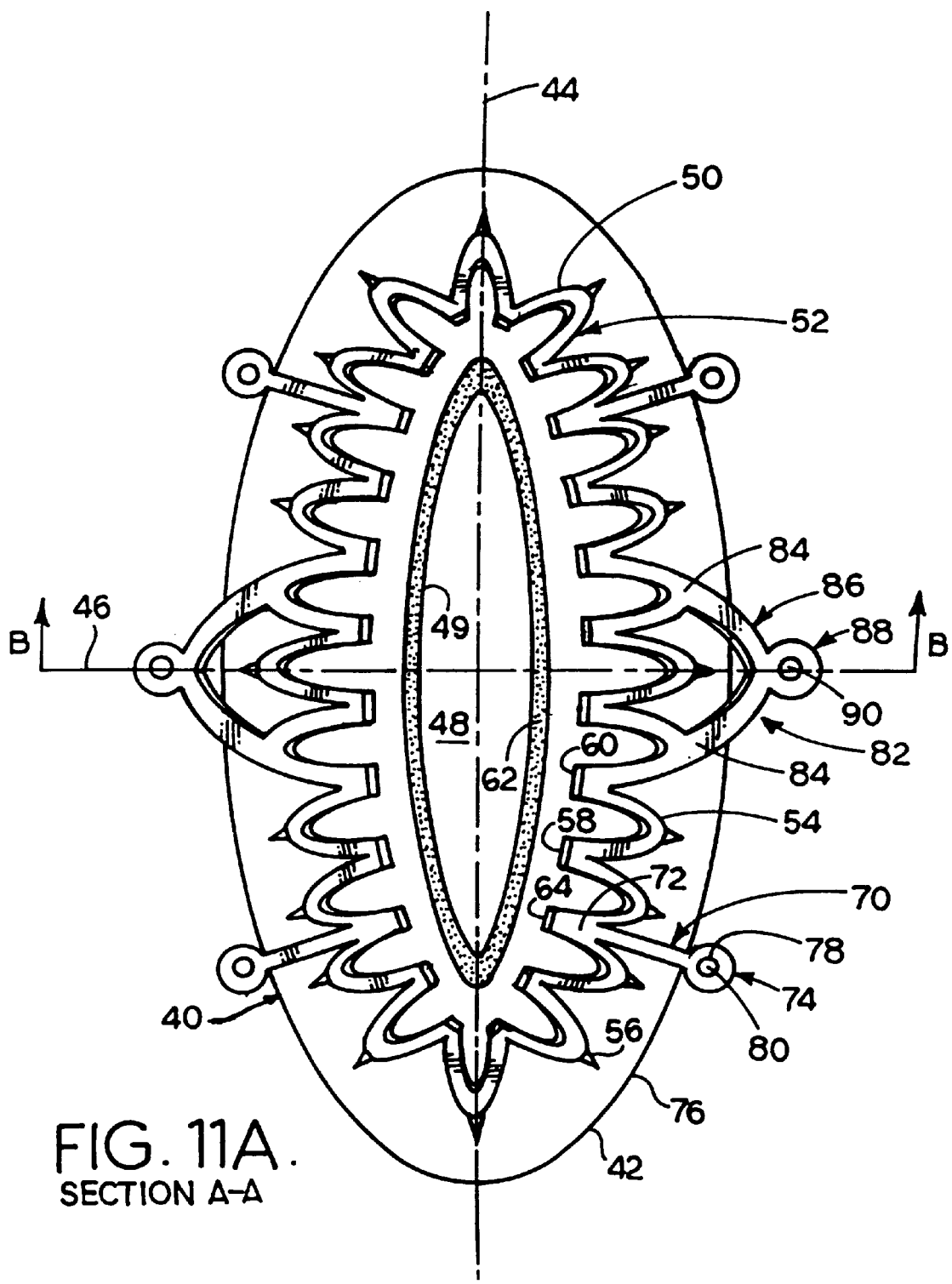
Figure 13A:
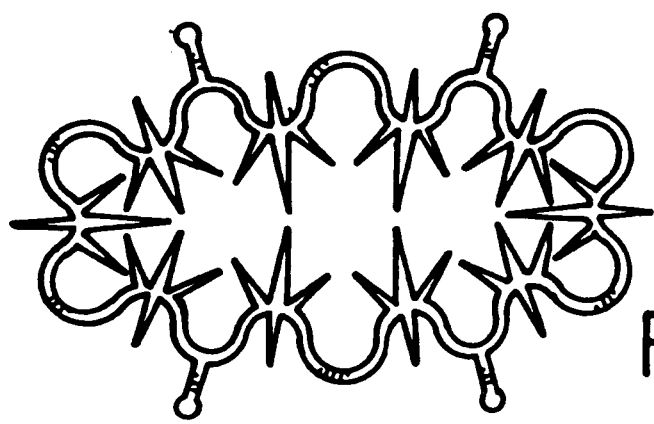
Figure 13B:
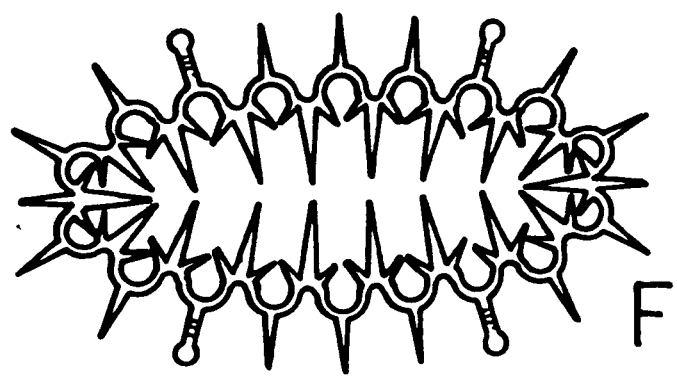
Figure 13C:
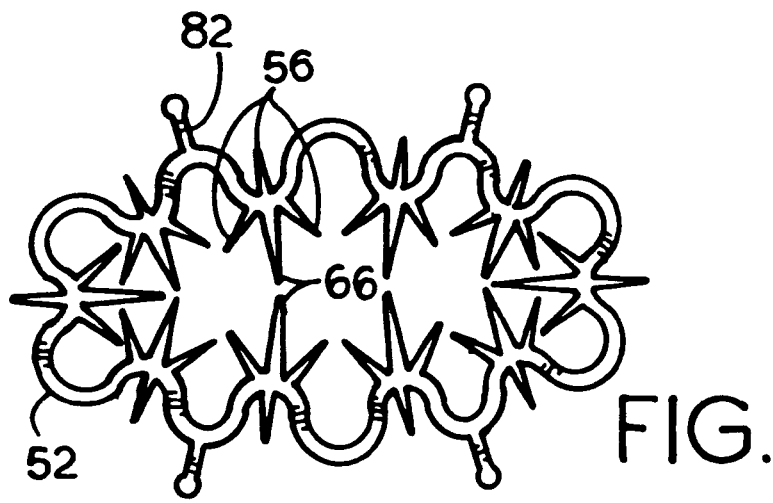
Figure 13D:
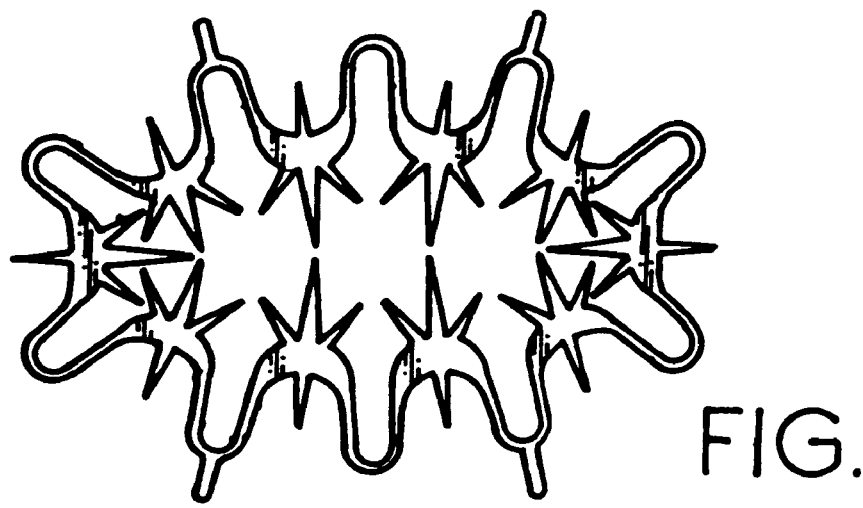
Figure 13E:
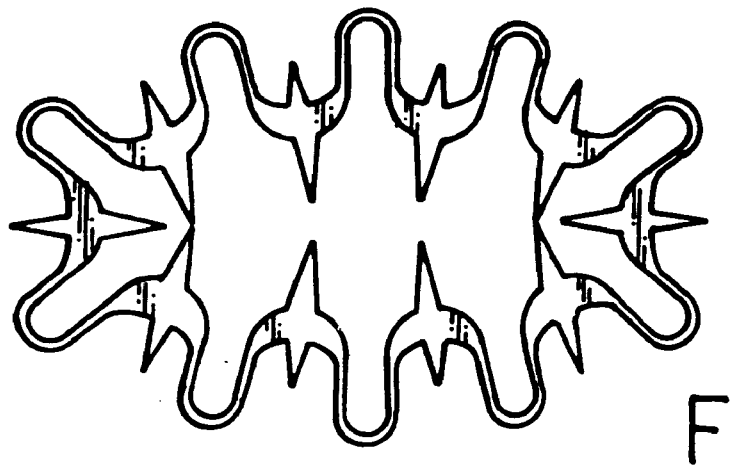
Figure 13F:
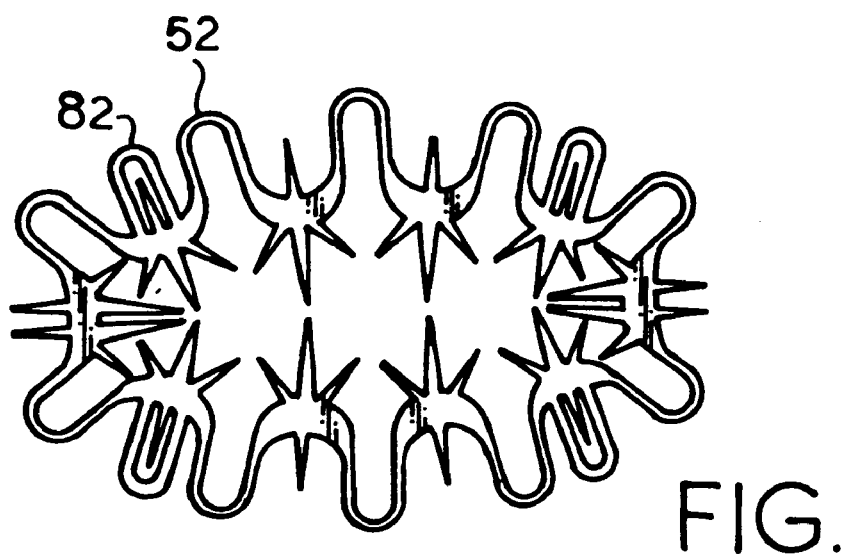

FIG. 11A is a sectional view taken along section line A—A of FIG. 11.

Figure 12:
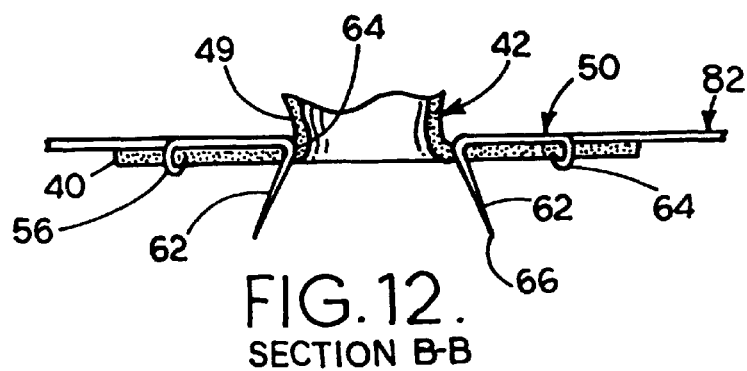

FIG. 12 is an sectional view of the cuff taken along line B—B of FIG. 11A.

FIGS. 13A–13F show alternative forms of a cuff.

FIG. 14 is an exploded view showing a single cuff form of the invention prior to joining a graft and an artery.

Figure 15:
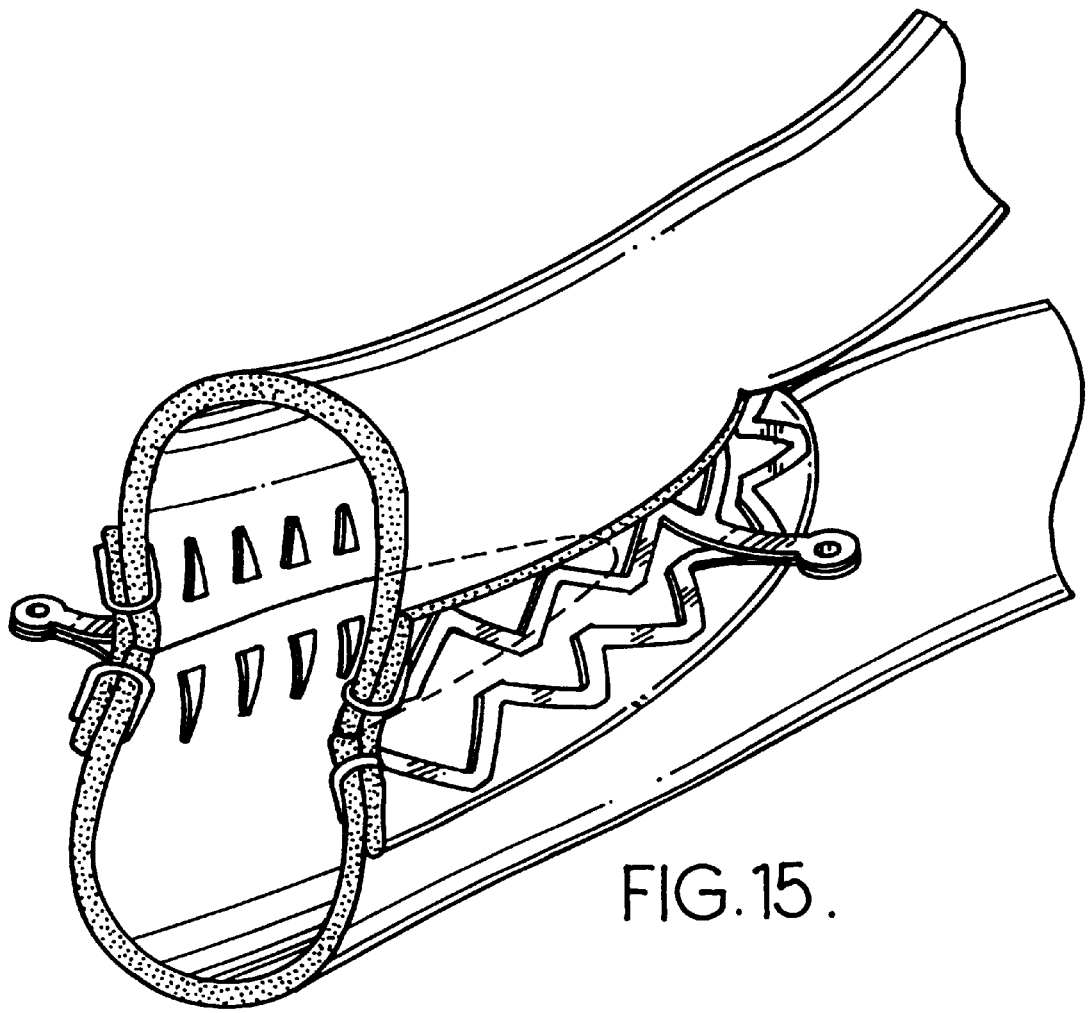

FIG. 15 is a cut away view showing the single cuff form after the graft has been joined to the artery.

Figure 16:
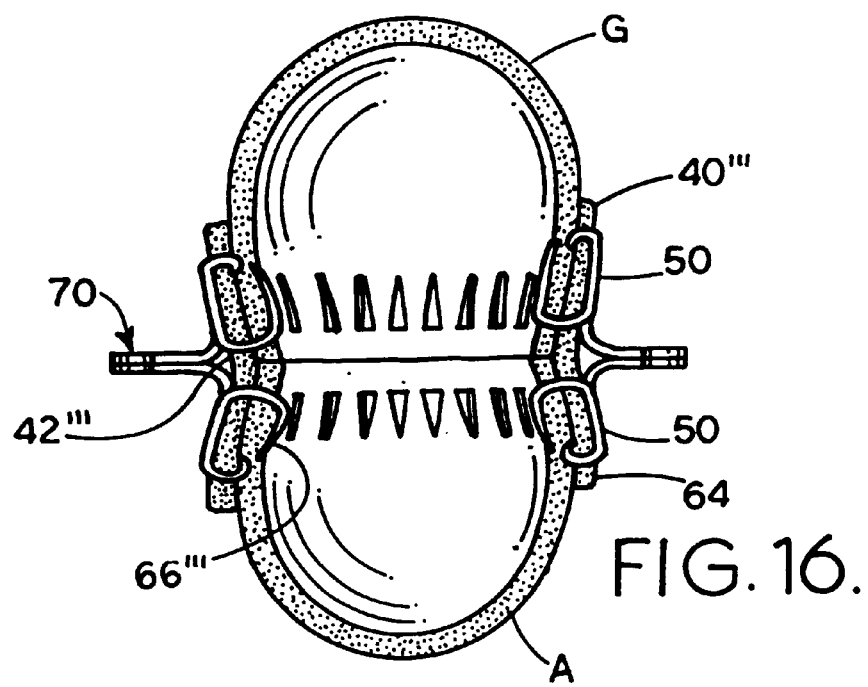

FIG. 16 is an elevational cross sectional view of the single cuff form of the invention joining a graft to an artery.

Figure 17:
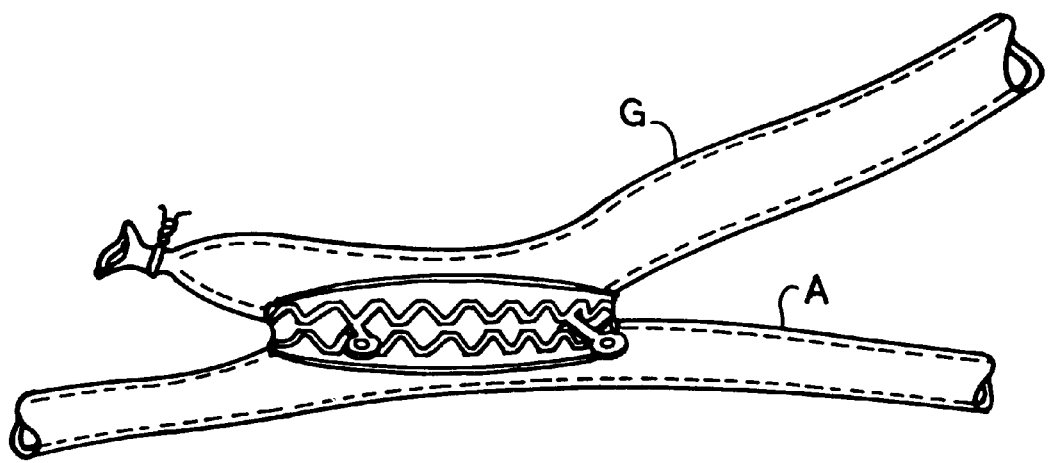

FIG. 17 is a perspective view of an anastomosis formed using the single cuff form of the invention in a side-to-side configuration, those skilled in the art being able to understand what an end-to-side configuration will look like based on the teaching of the present disclosure.

Figure 18A:
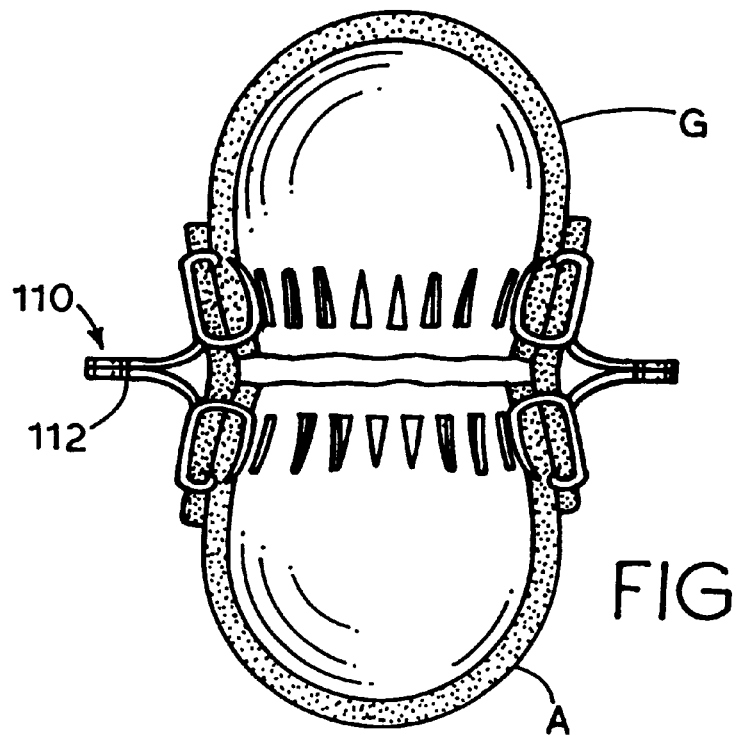

FIG. 18A shows a single cuff form of the invention just prior to drawing the ends of the two blood vessels together.

Figure 18B:
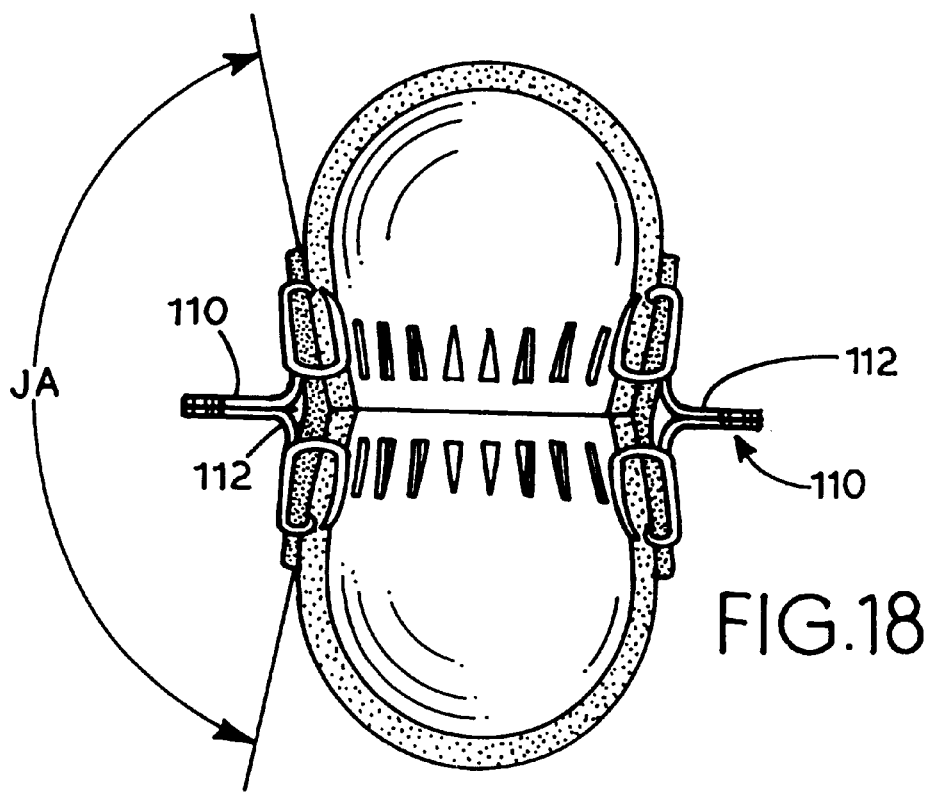

FIG. 18B shows the single cuff form of the invention after the ends of the blood vessels have been drawn together.

Figure 19:
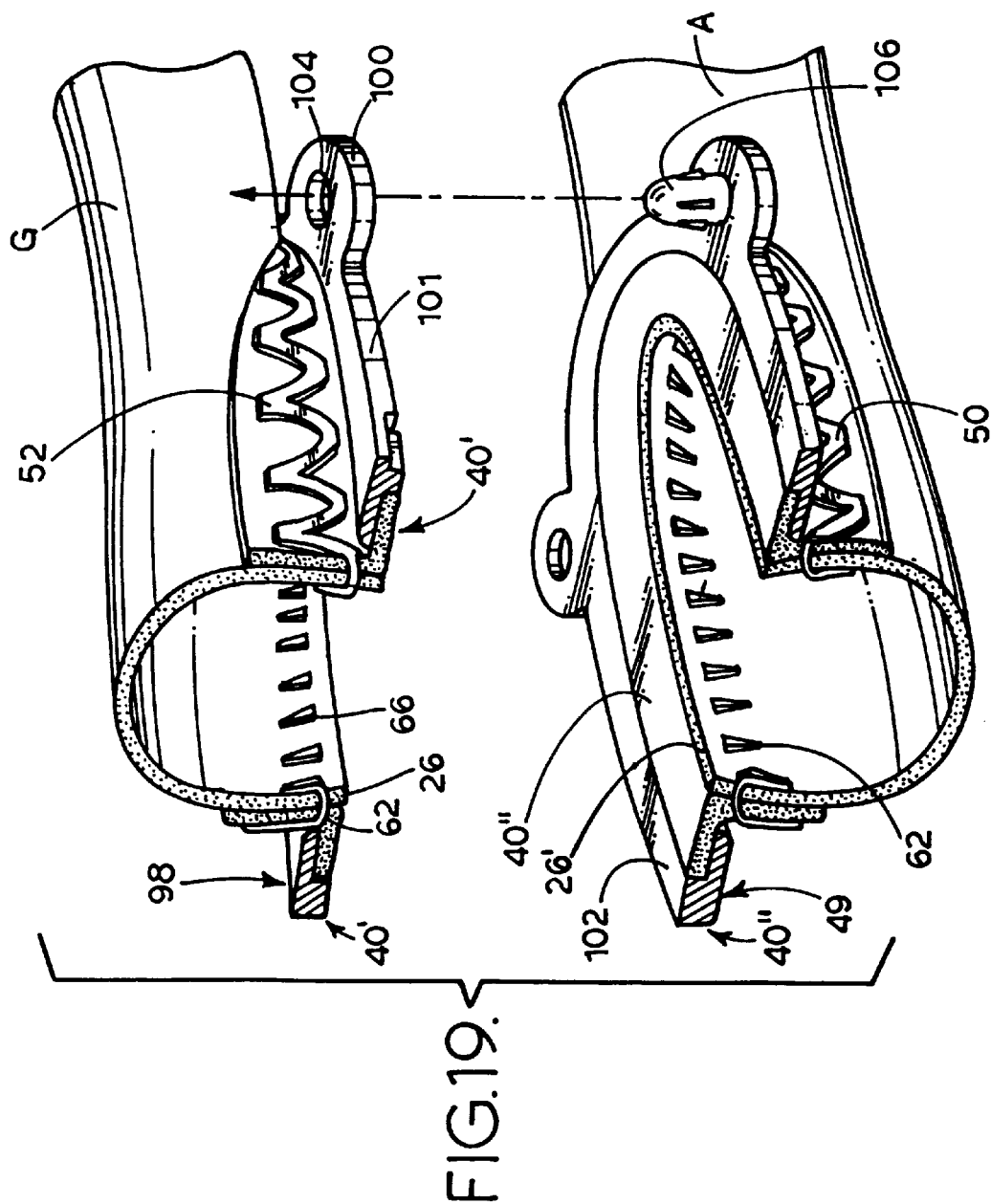

FIG. 19 is an exploded perspective view of one form of the invention in which two cuffs are used to join an artery with a graft.

Figure 20:
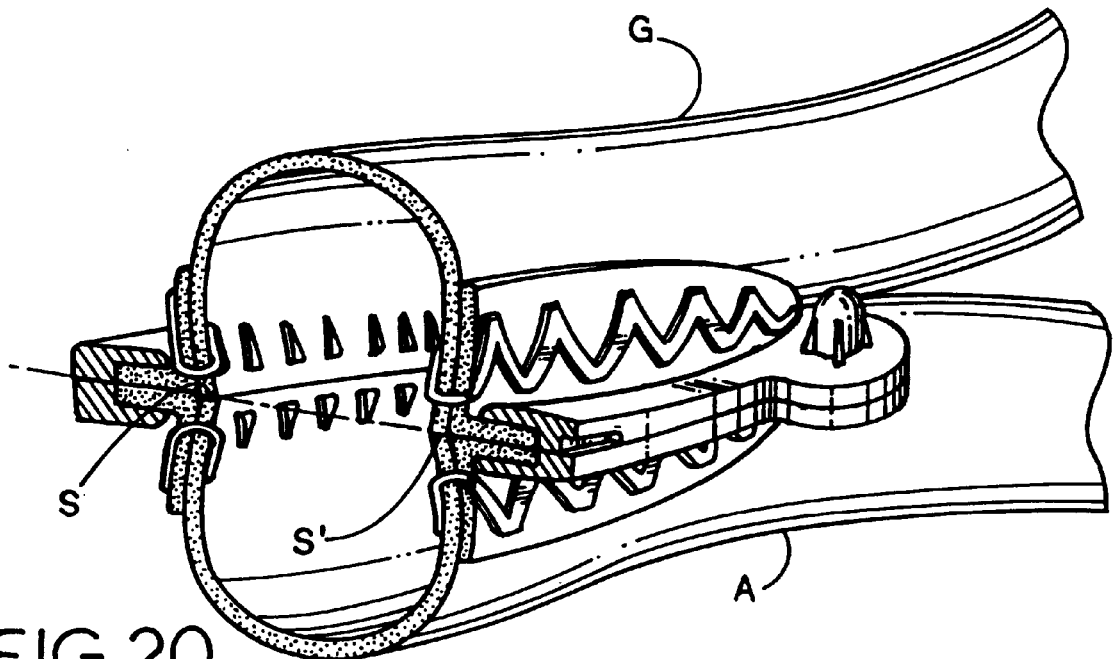

FIG. 20 is a perspective view of a section of the joined artery and graft using two cuffs.

Figure 21:
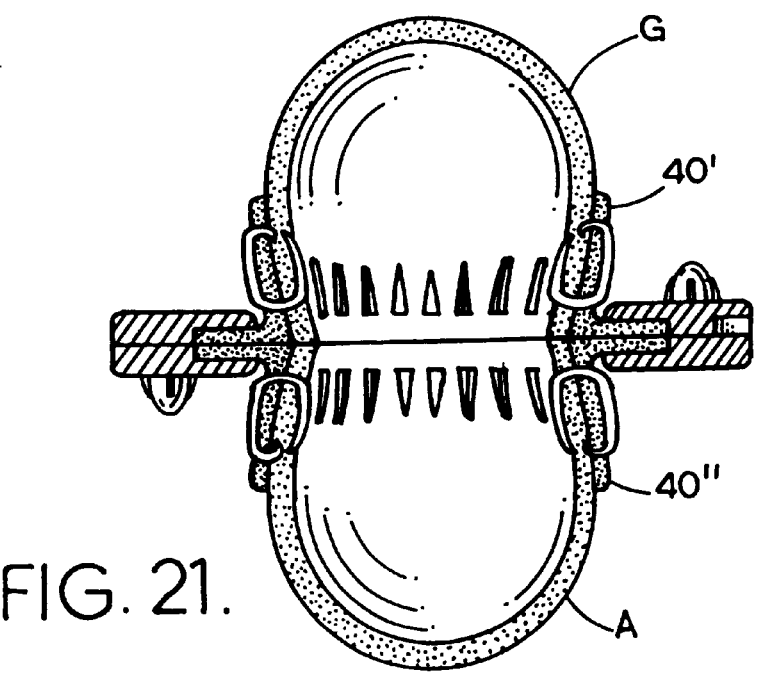

FIG. 21 is an elevational cross sectional view of the two cuff form of the invention in situ.

Figure 22:
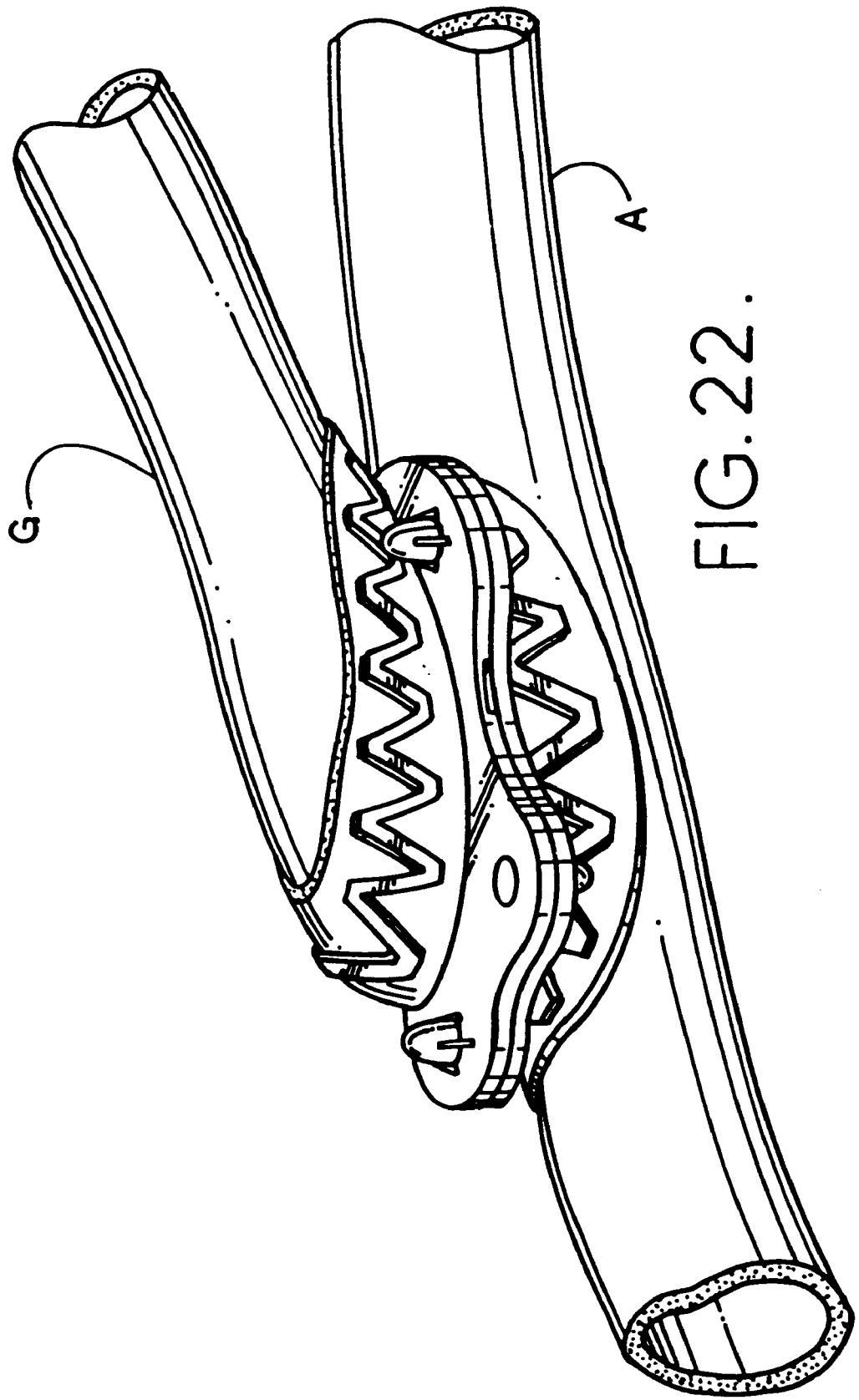

FIG. 22 is a perspective view of the two cuff form of the invention in an anastomosis which joins a graft to an artery in an end-to-side configuration.

Figure 23:
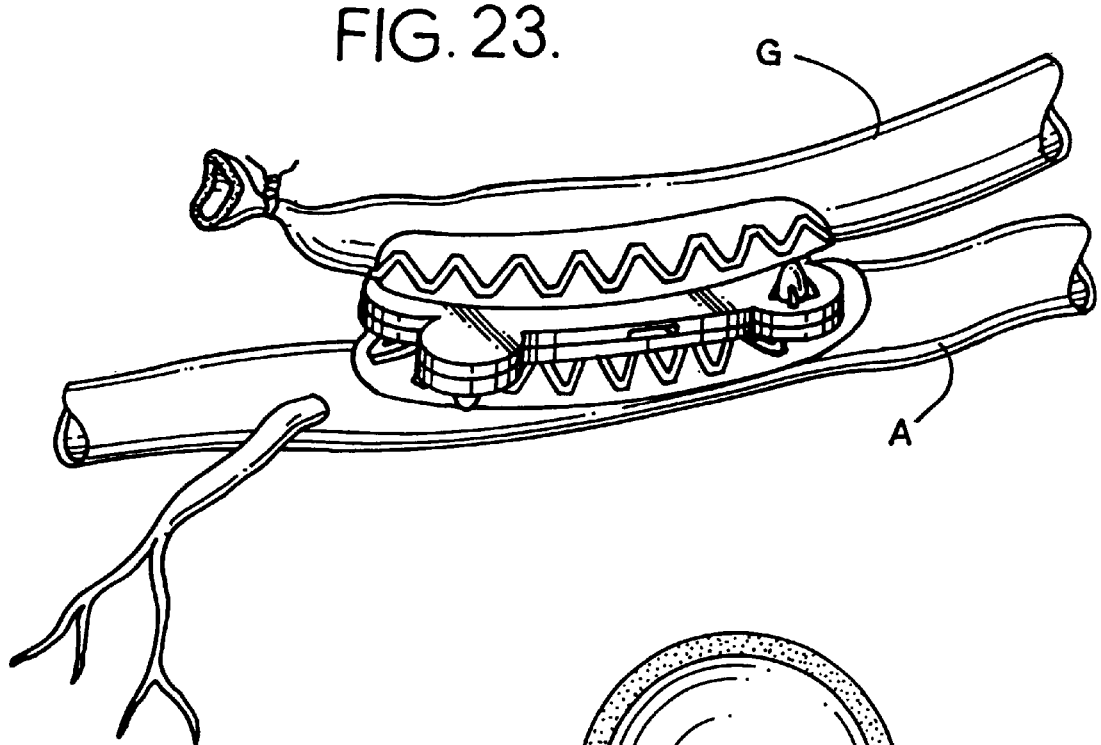

FIG. 23 is a perspective view of the two cuff form of the invention in an anastomosis which joins a graft to an artery in a side-to-side configuration, with the graft being tied off by a suture.

Figure 24:
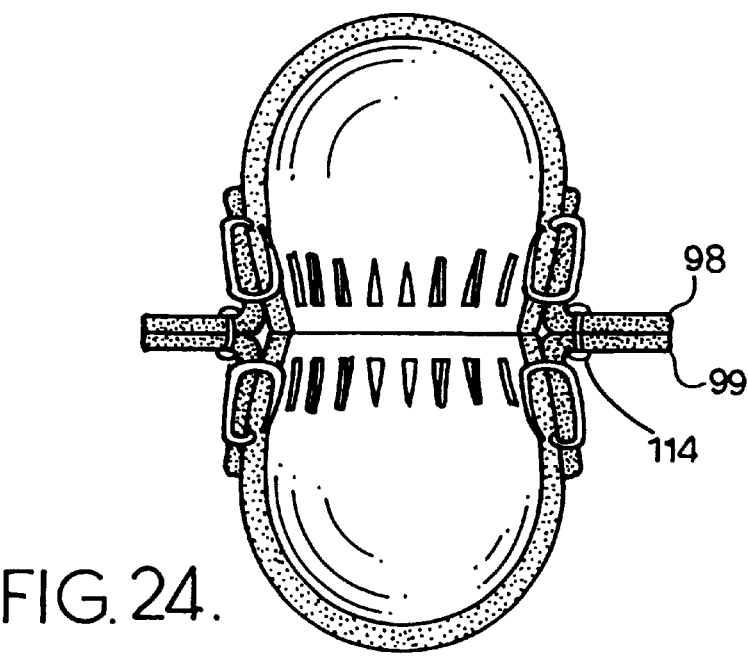

FIG. 24 is an elevational view of another form of the two cuff form of the invention showing how the two cuffs are held together whereby the graft and the artery are pulled together in healing abutment.

Figure 25:
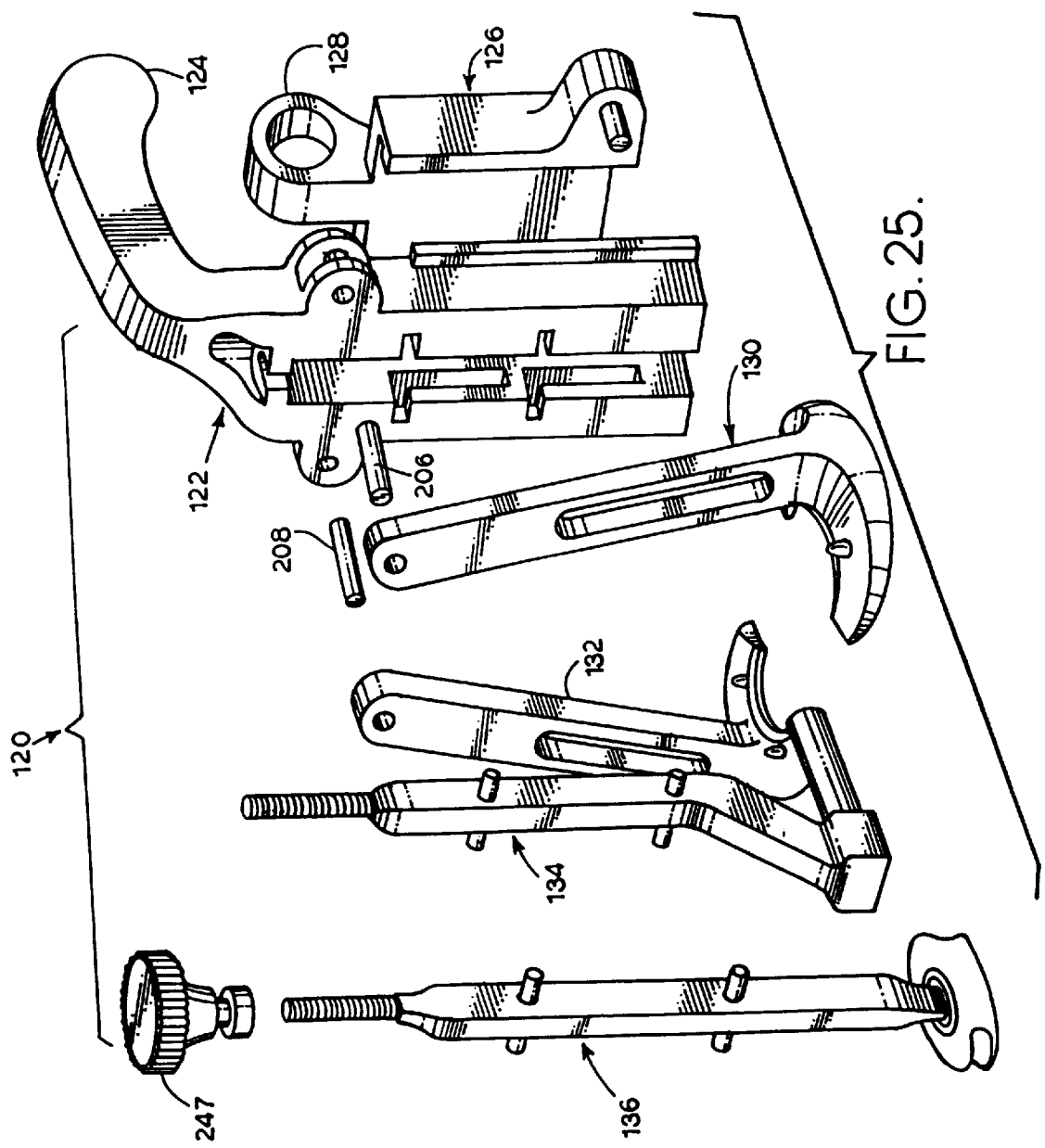

FIG. 25 is an exploded perspective view of a tool used in performing the anastomosis according to the present invention.

FIG. 25A is an exploded perspective view of a tool used in performing the anastomosis according to the present invention, with a cuff in place.

Figure 26:
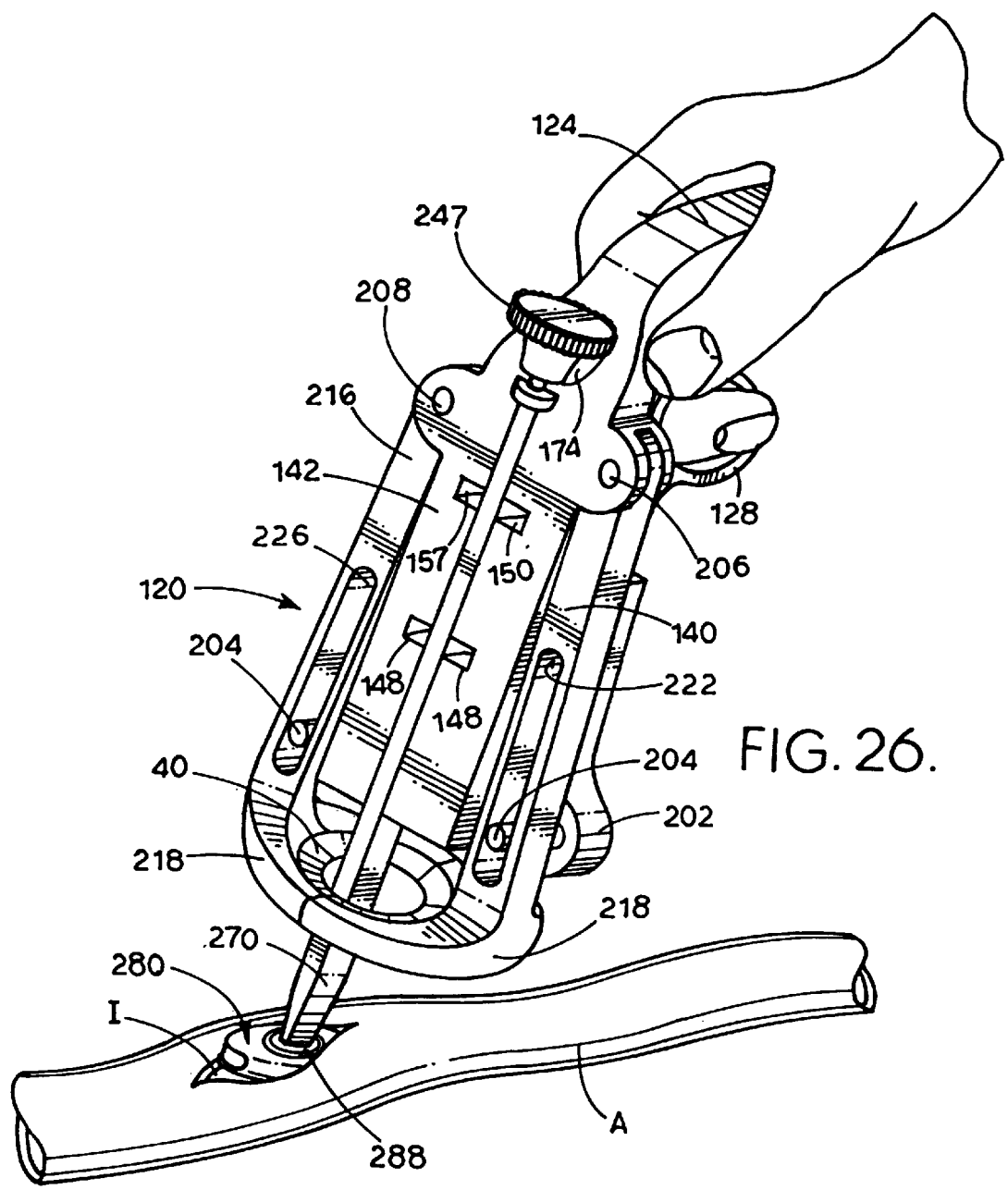

FIG. 26 is a perspective view indicating the tool in use in placing a cuff on an artery.

Figure 27:
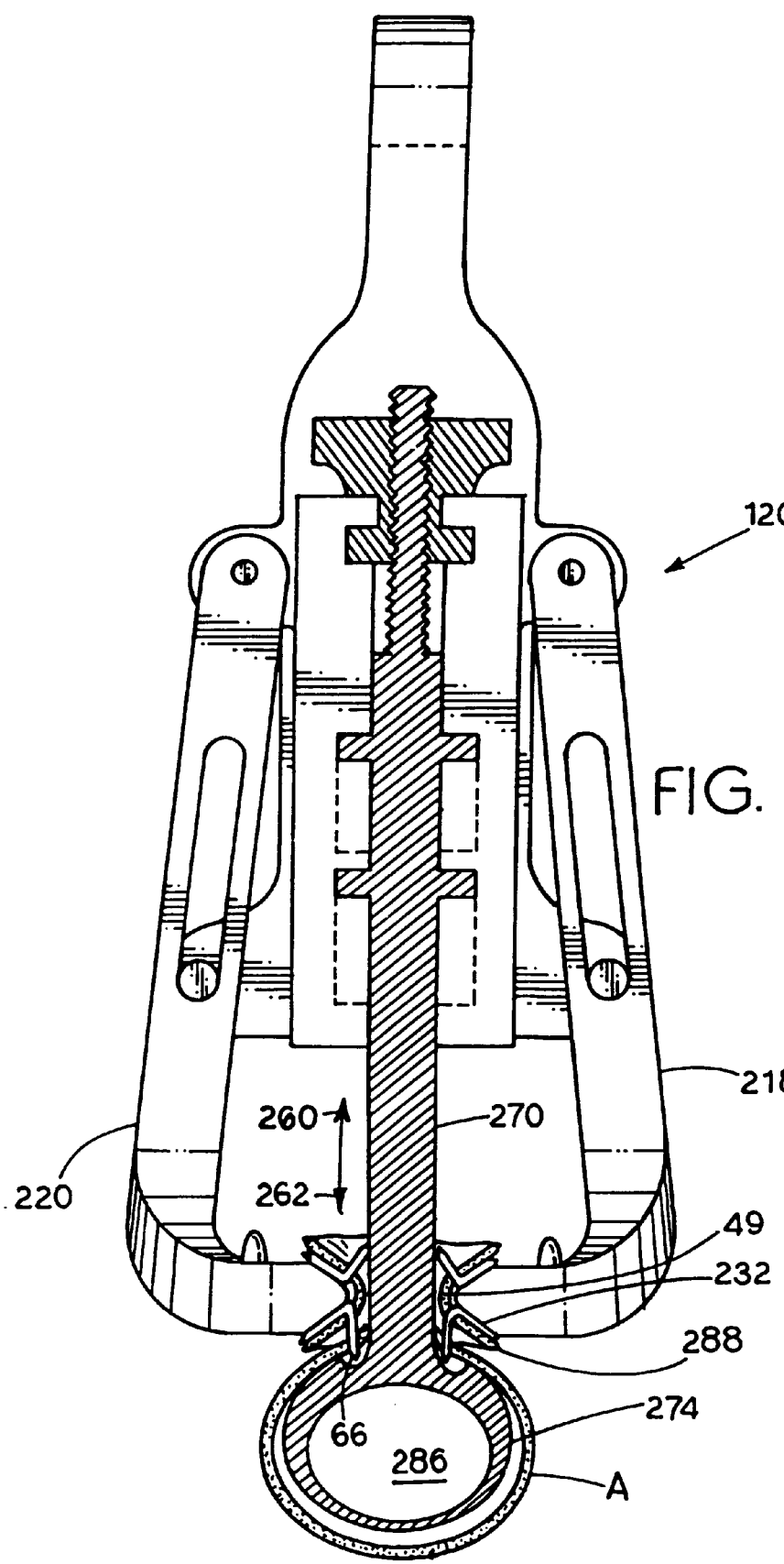

FIG. 27 is an elevational view of a tool in place in an artery just prior to setting a cuff on the artery.

Figure 28:
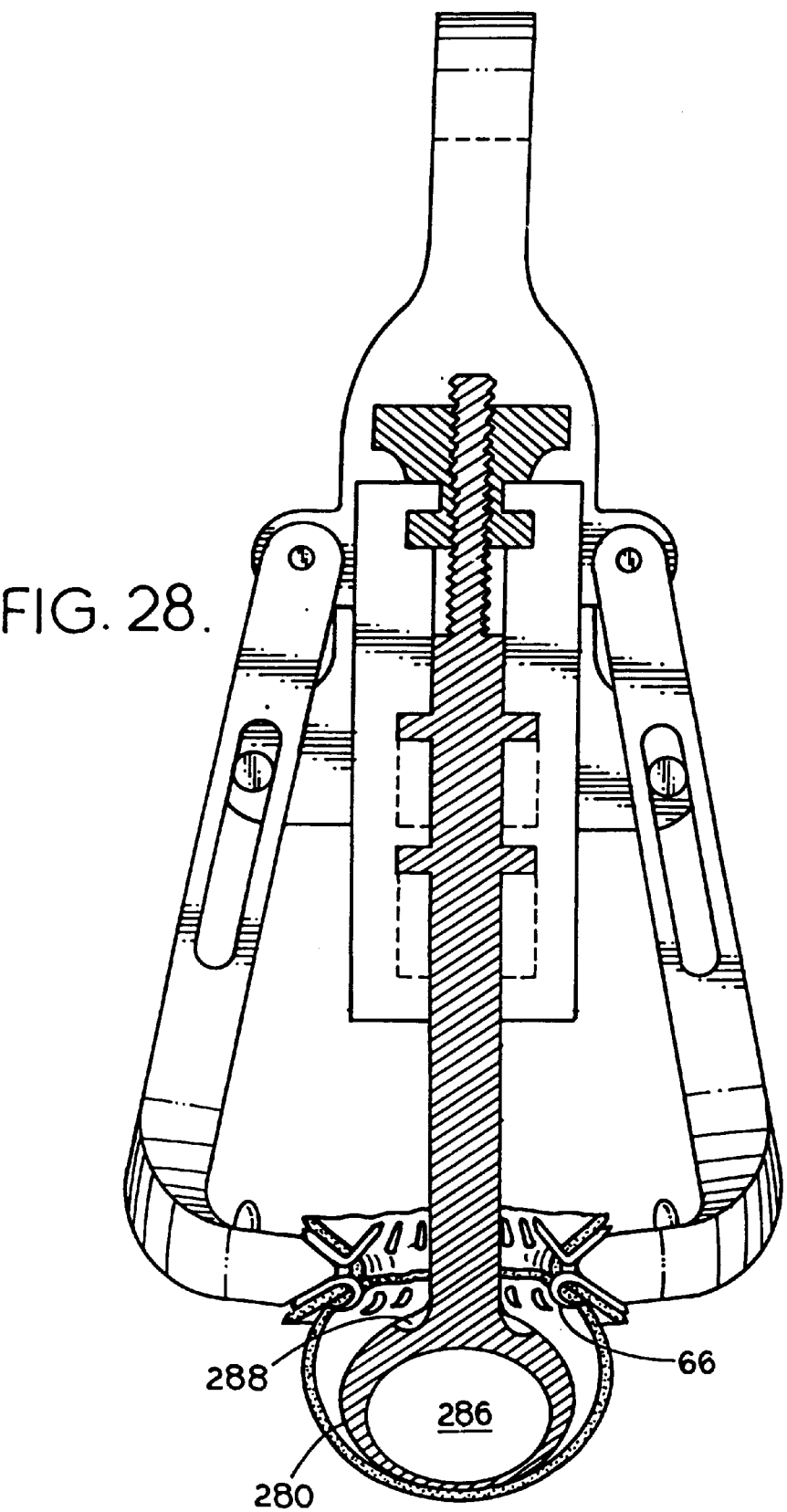

FIG. 28 is an elevational view of a tool in place after a cuff has been set onto an artery and just prior to removing an anvil of the tool from the artery.

FIG. 29 is an elevational view of a tool with an anvil in place in a graft for placement of a single cuff form of the invention.

FIG. 30 shows a graft vessel prepared to receive a cuff.

FIG. 31 shows a tool holding a cuff prior to placing the cuff on the graft vessel shown in FIG. 30.

FIG. 32 shows a tool used to cinch a cuff to a graft vessel that has been located in a cuff.

FIG. 33 shows a graft vessel located in a cuff prior to being cinched to that cuff by the tool shown in FIG. 32.

Figure 34:
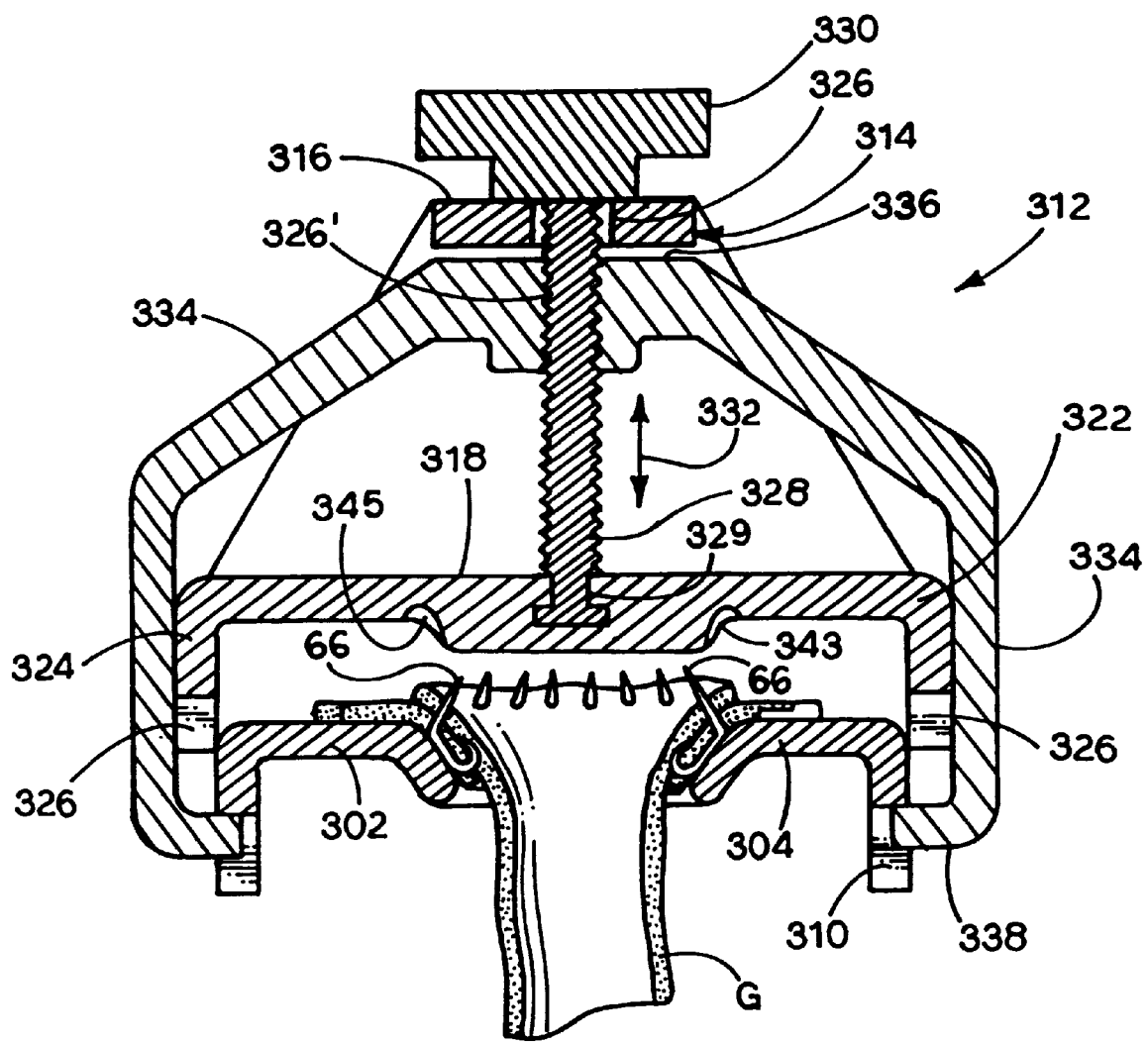

FIG. 34 shows the tool just prior to setting the means for attaching the cuff to the graft vessel.

Figure 35:
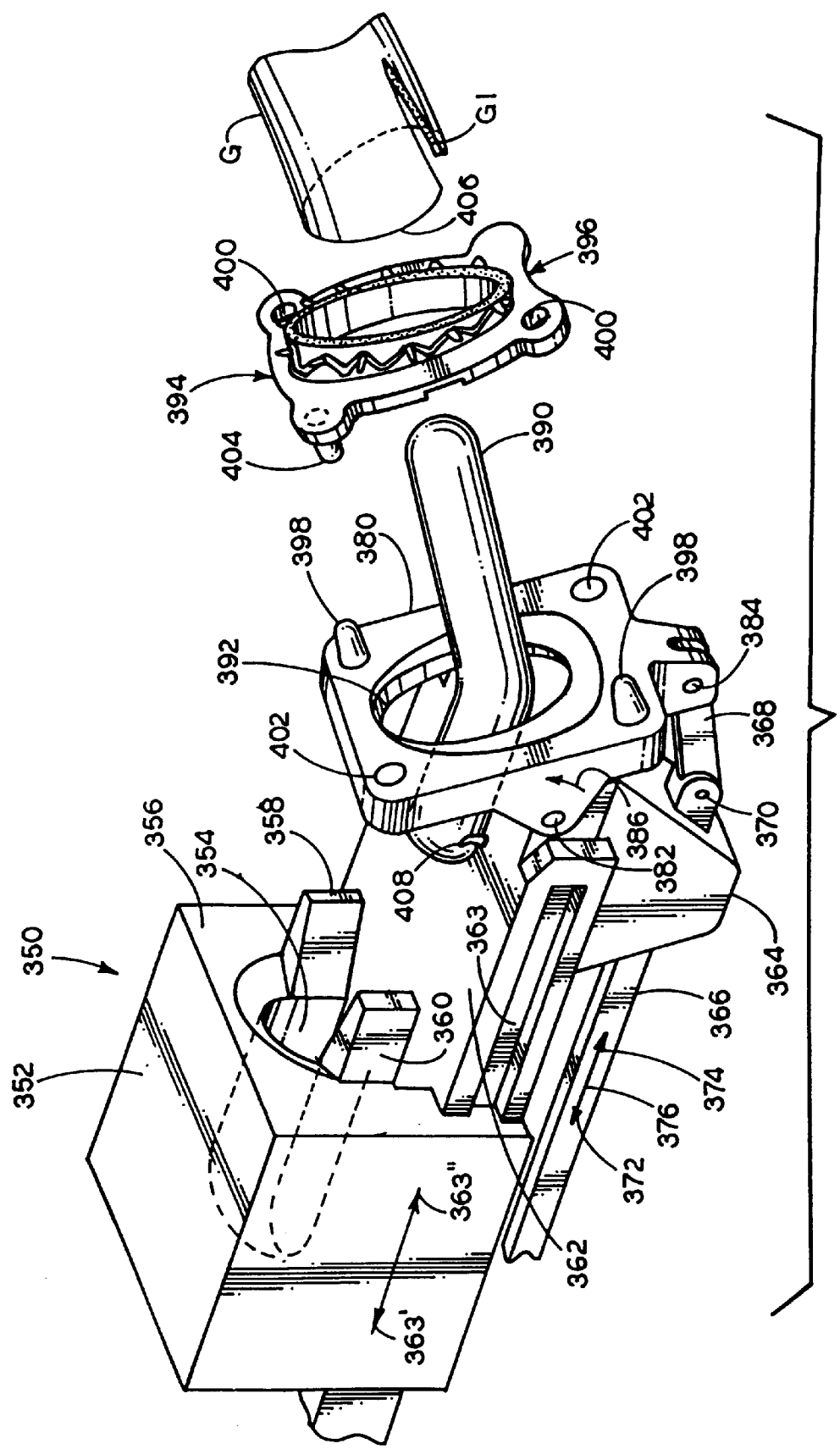

FIG. 35 shows an alternative form of a tool for applying a cuff to a graft vessel.

FIGS. 36A–36D show the steps used in applying a cuff to a graft vessel using the tool shown in FIG. 35.

Figure 37:
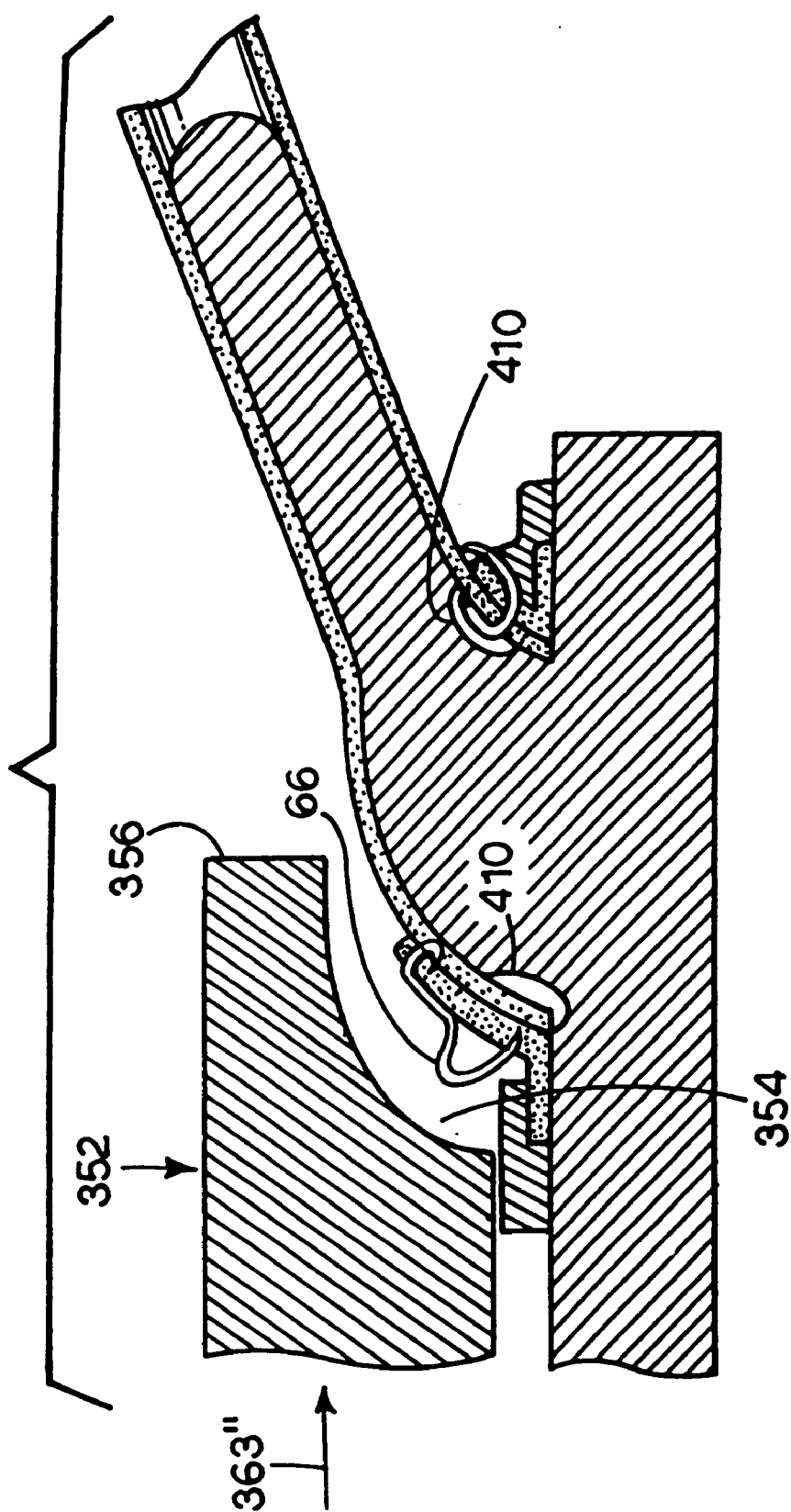

FIG. 37 shows a tool applying the means for holding the cuff to the vessel in which the means is such that the vessel will not be damaged.

Figure 38:
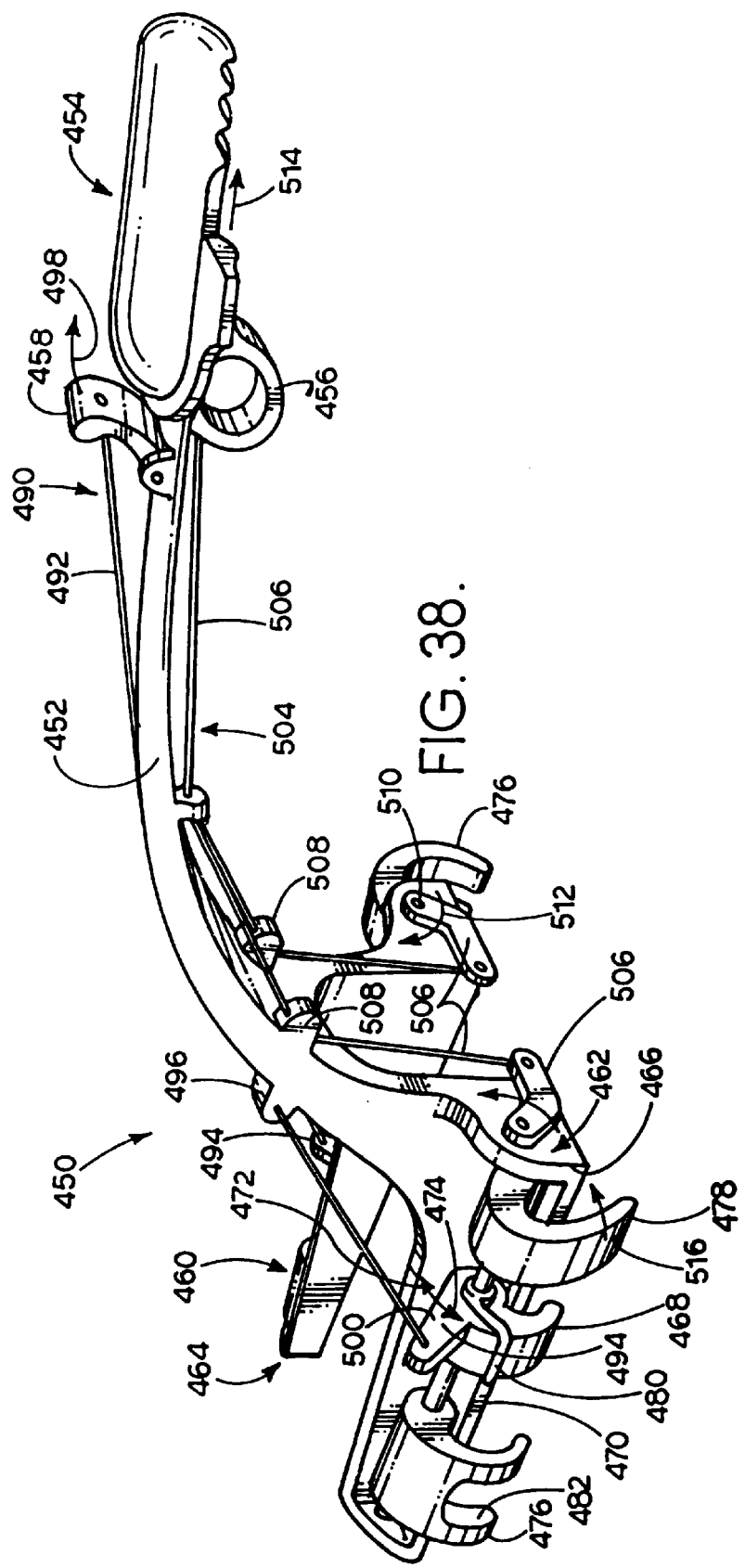

FIG. 38 shows a tool used to join two cuffs together.

Figure 39:
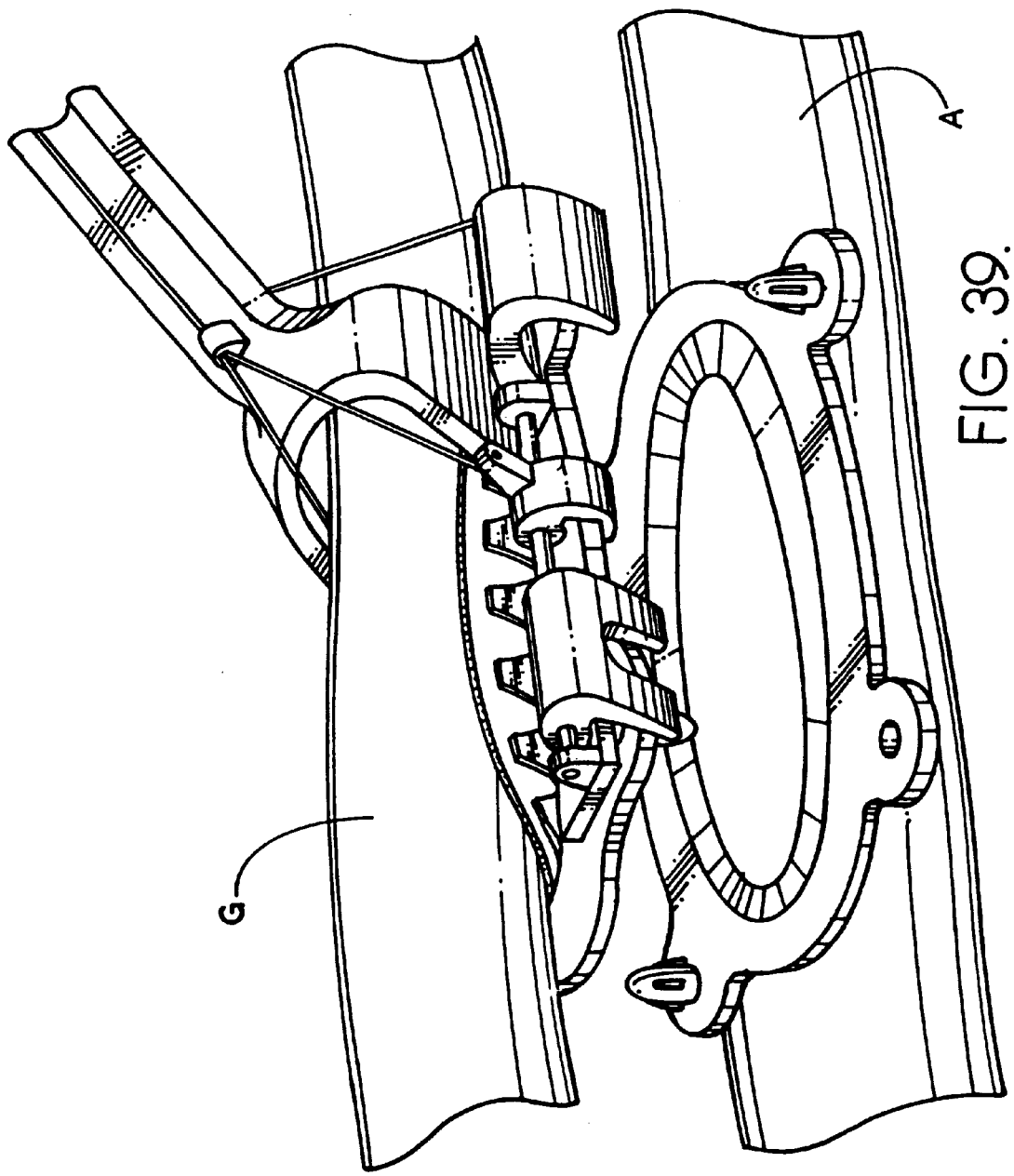

FIG. 39 shows the tool used to join two cuffs together docked to one cuff and prior to joining that cuff to another cuff.

Figure 40:
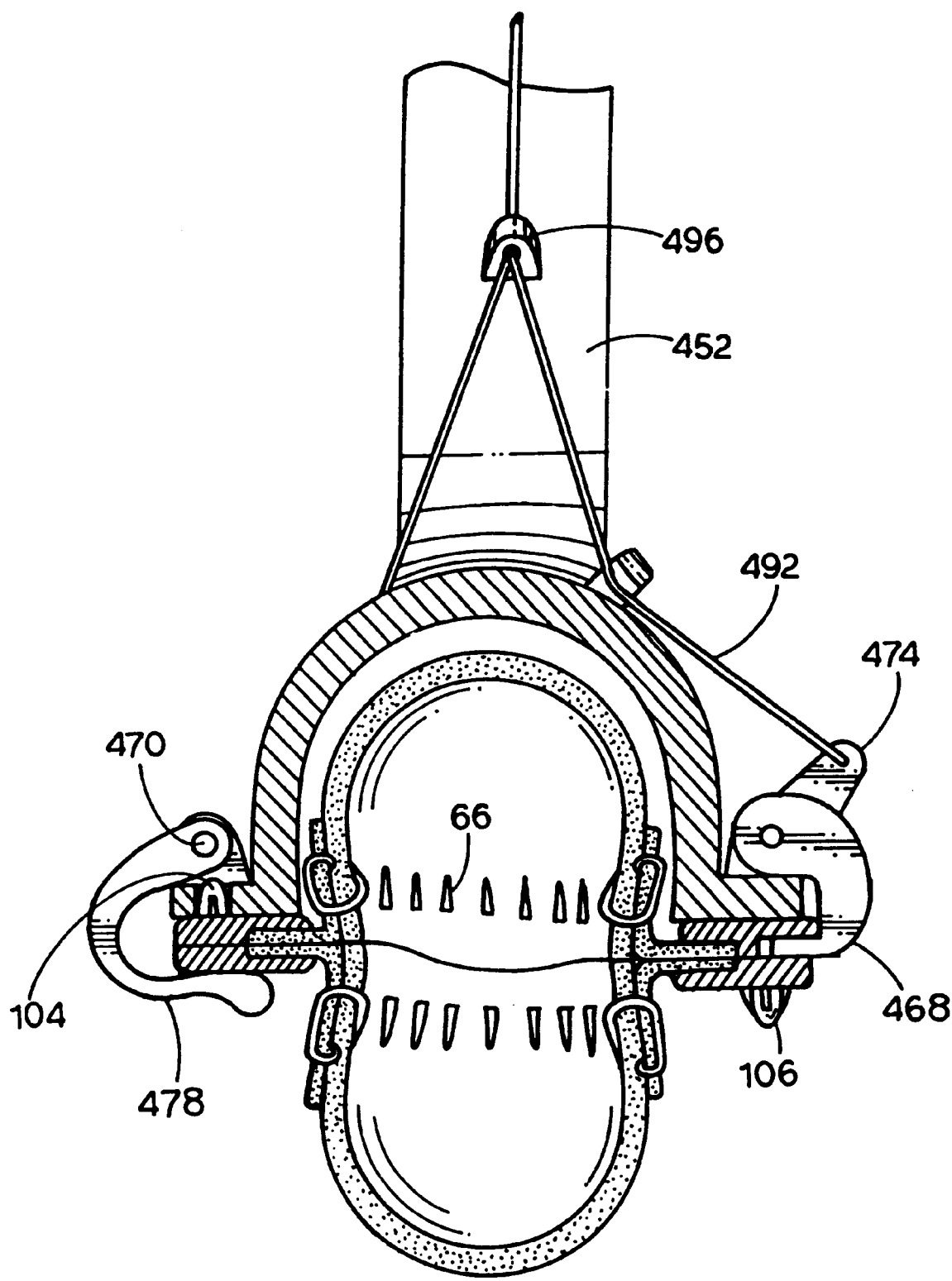

FIG. 40 shows the tool docked to one cuff and joining that cuff to another cuff.

FIG. 41 is a flow chart for the method of performing an anastomosis for a single cuff form of the invention with the vessels being joined in a side-to-side configuration.

Figure 42A:
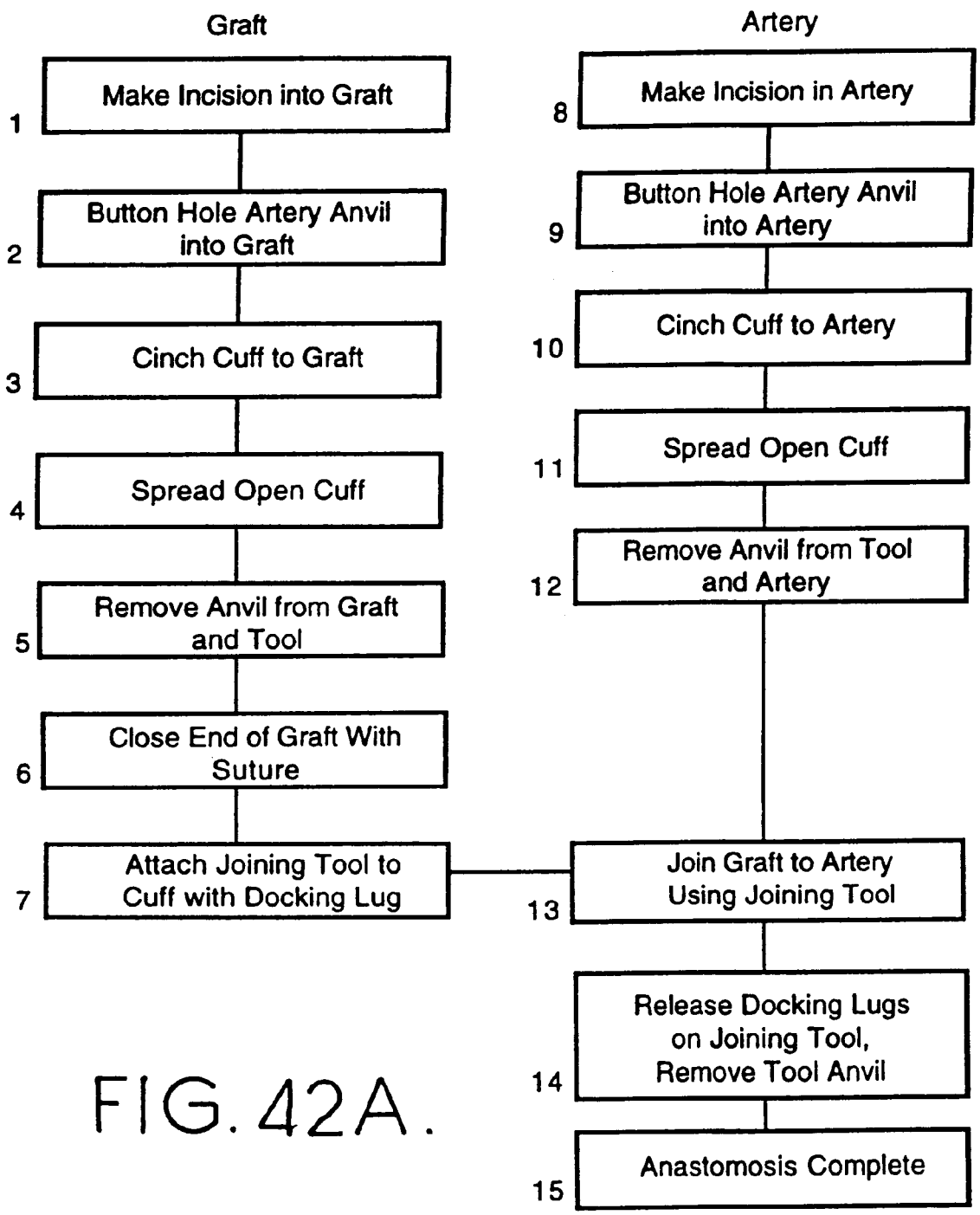

FIG. 42A is a flow chart for the method of performing an anastomosis for a double cuff form of the invention with the vessels being joined in a side-to-side configuration.

Figure 42B:
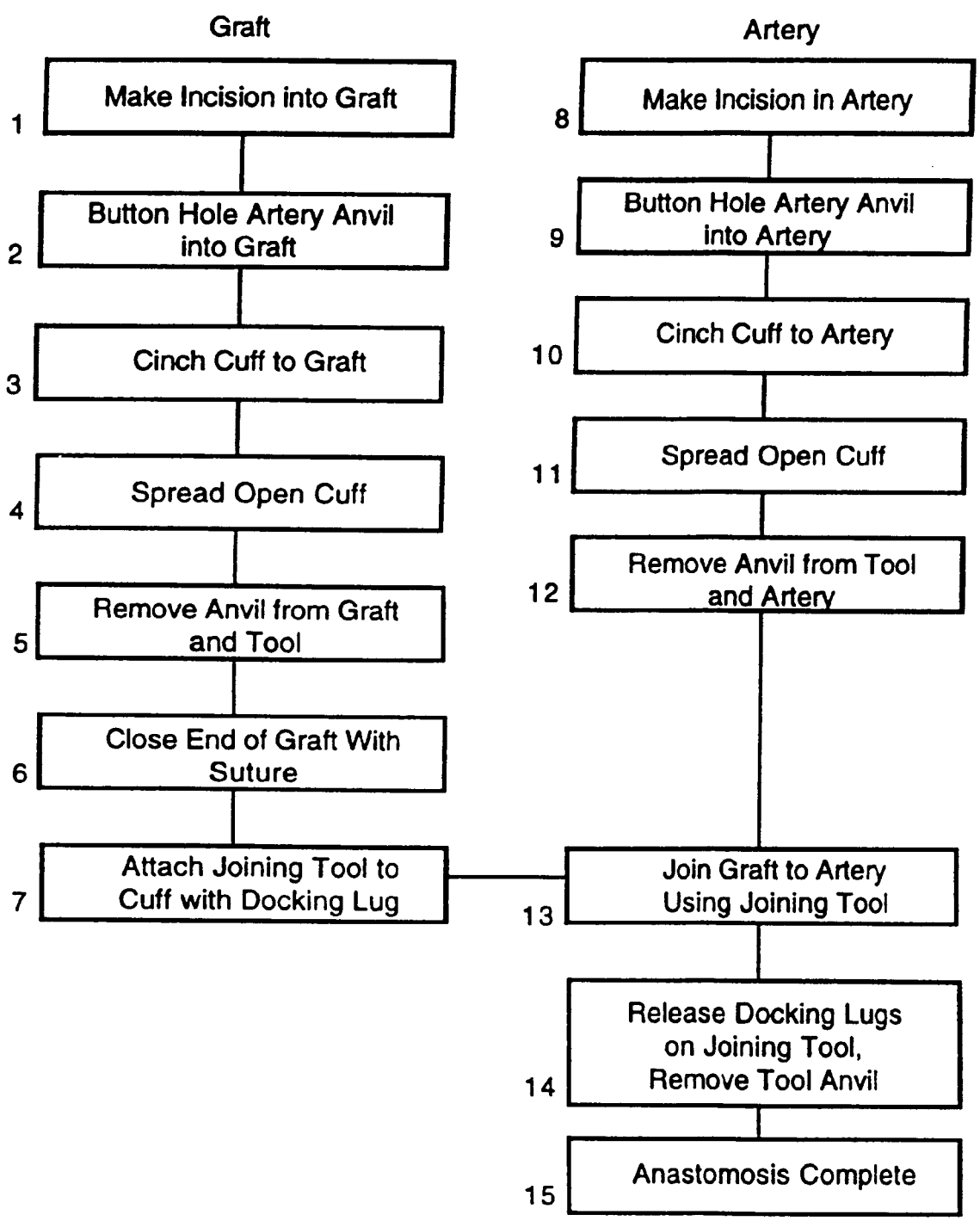

FIG. 42B is a flow chart for the method of performing an anastomosis for a double cuff form of the invention with the vessels being joined in an end-to-side configuration.

Figure 43:
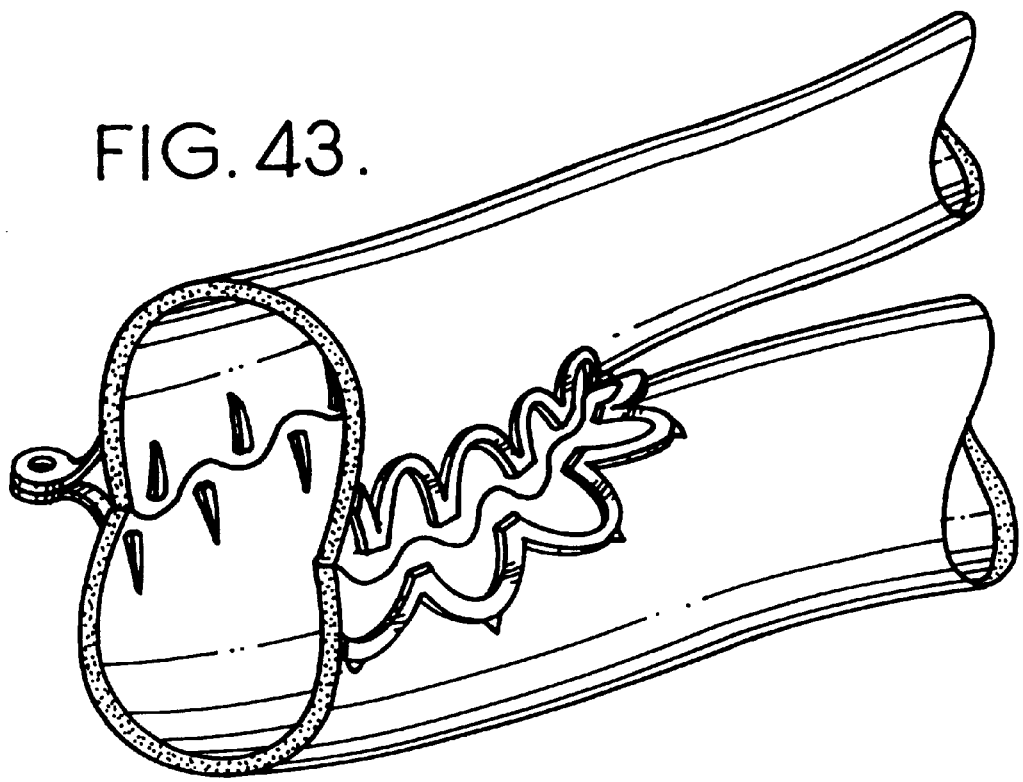

FIG. 43 shows a single cuff form of the invention which has omitted the hemostatic medium.

Figure 44:
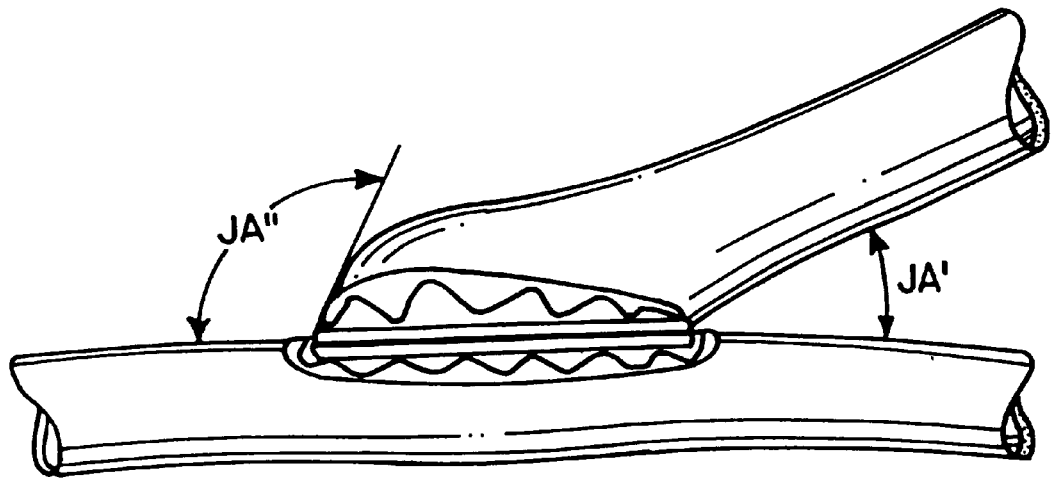

FIG. 44 shows the continuously varying nature of the junction angle.

Figure 45:
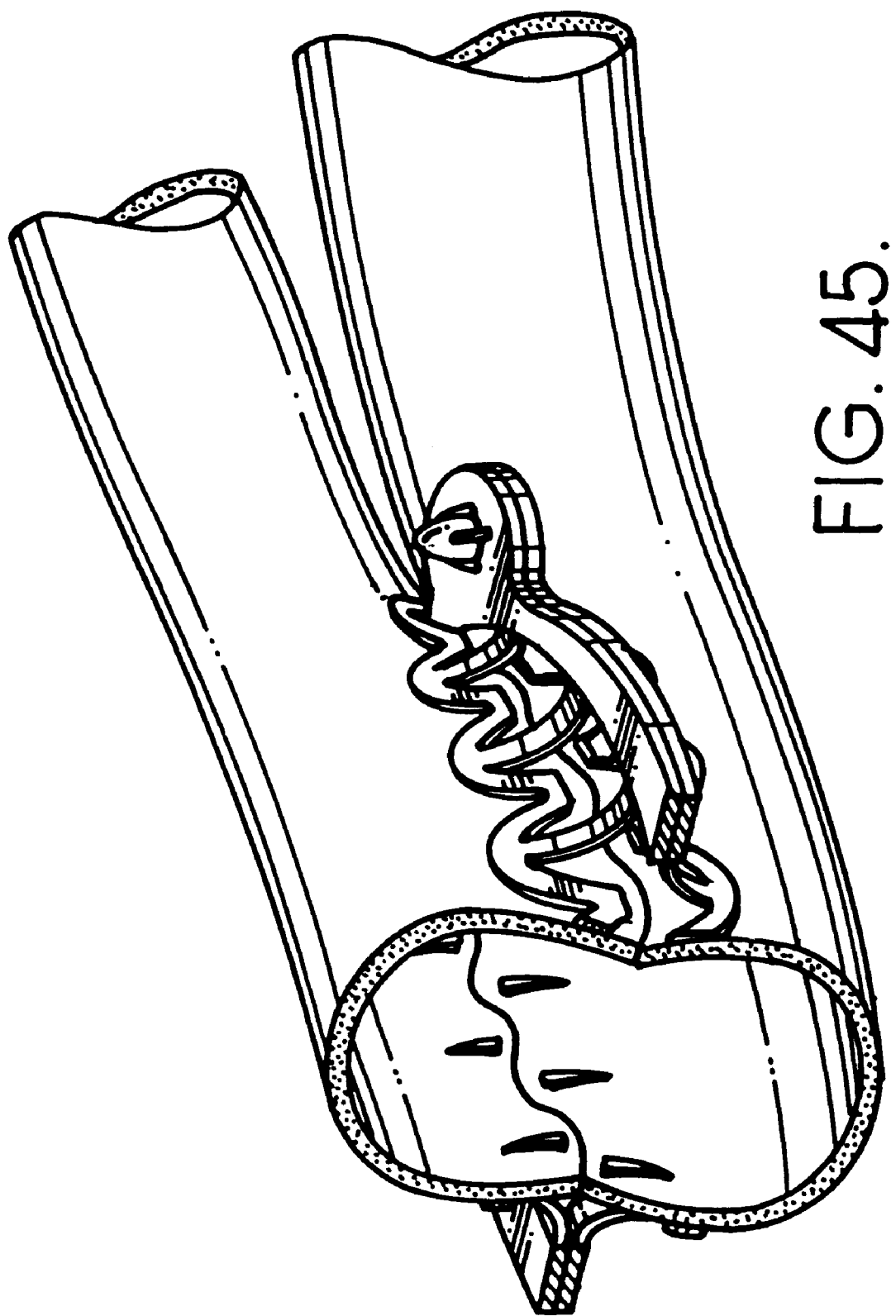

FIG. 45 shows the double cuff form of the invention which has omitted the hemostatic medium.

Figure 46:
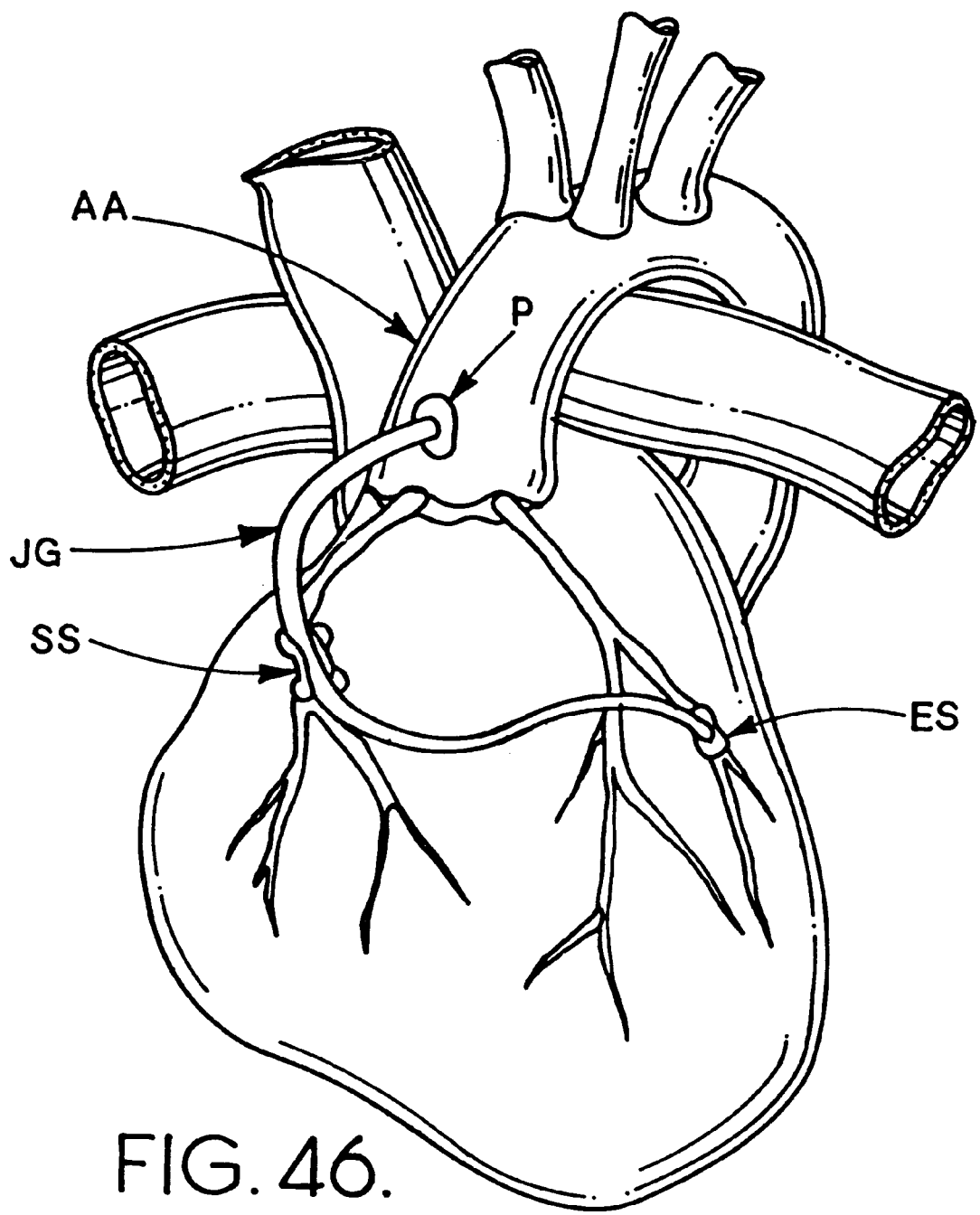

FIG. 46 shows how the means and method of the present invention can be applied to a multiple graft technique.

DETAILED DESCRIPTION OF THE PREFERRED EMBODIMENT OF THE INVENTION

Locating and Performing the Arteriotomy

Figure 1:
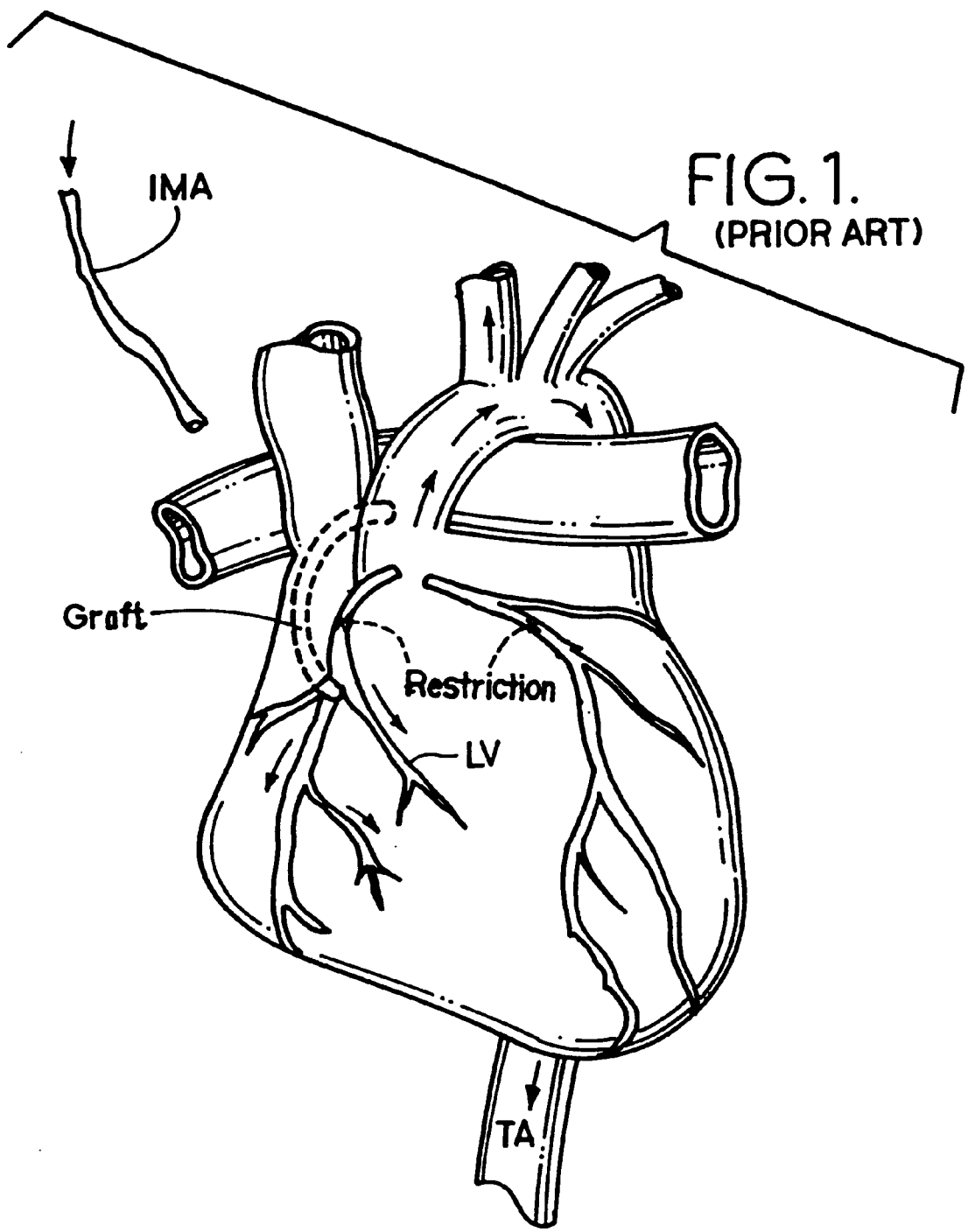
FIG. 1 is a schematic showing a heart.
Figure 2:
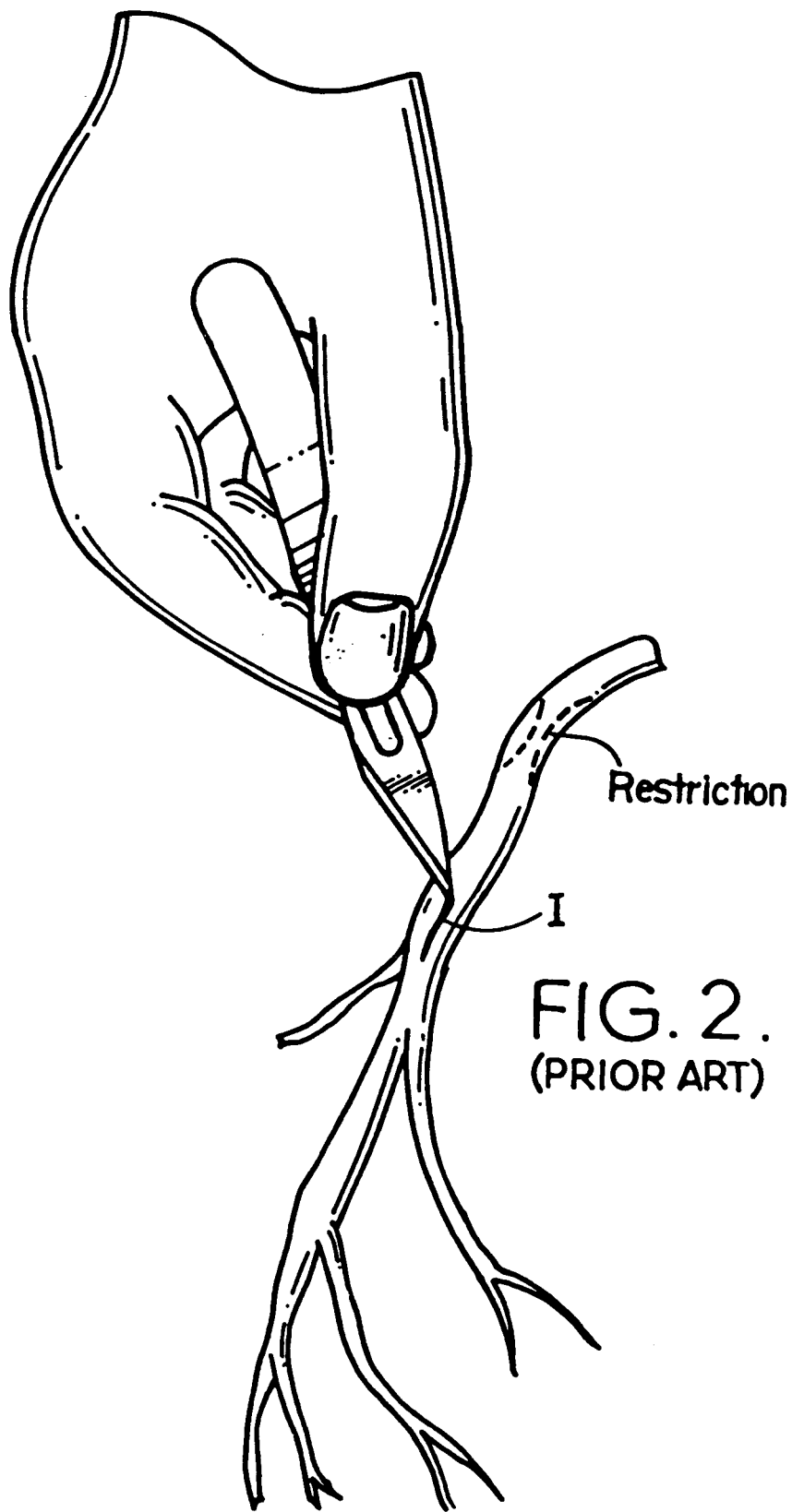
FIG. 2 illustrates a prior art method of locating an incision in an artery for performing an anastomosis.

By way of orientation, FIGS. 1 and 2 indicate the locating and performing of an arteriotomy. As is well understood to those skilled in the art, locating the position of an anastomosis is extremely important and extremely delicate. The location must be selected with extreme accuracy and precision. This is especially so since the blood vessels are often extremely small. This is indicated in FIGS. 1 and 2 where the location of a restriction is indicated as R and an arteriotomy is indicated at I in FIG. 2. The arteriotomy must be made in a proper location with respect to the restriction R or the surgery will not be as effective as it could be. Furthermore, an anastomosis must be performed accurately and effectively to be successful. The present invention discloses and teaches a means and a method of performing such an anastomosis.

Prior Art

Figure 3:
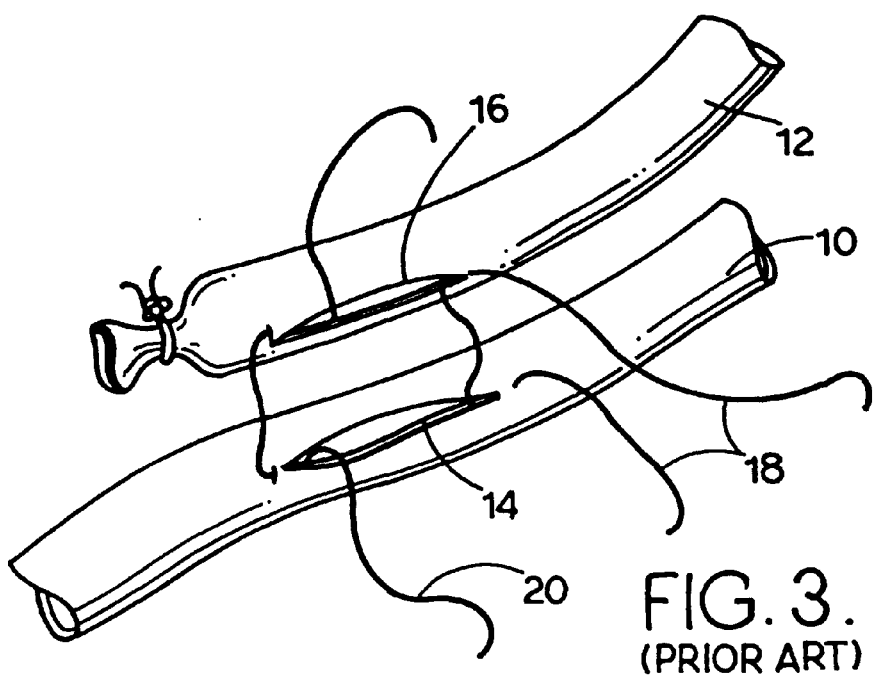
Figure 4:
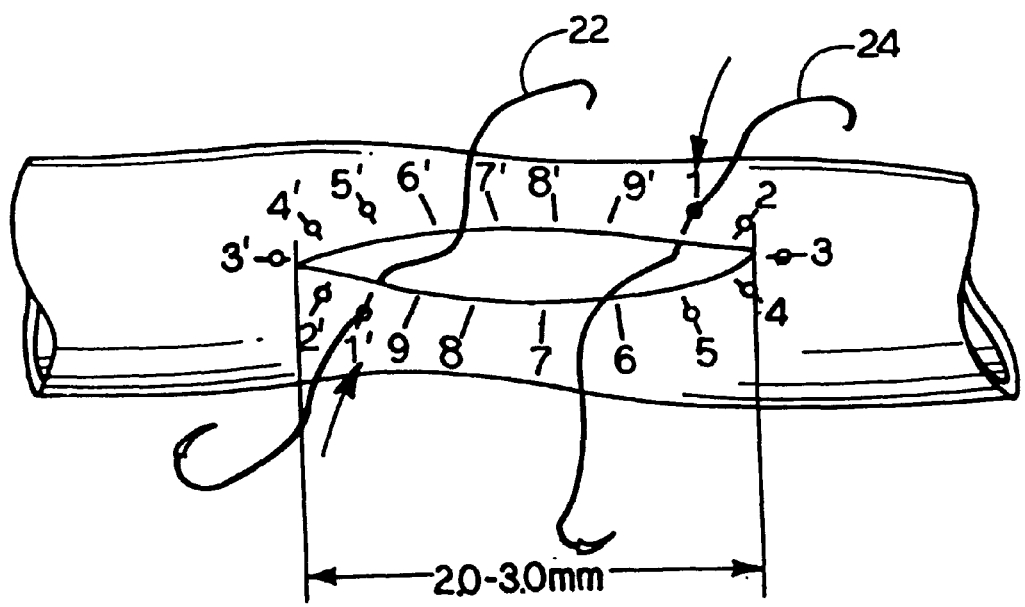
Figure 5A:
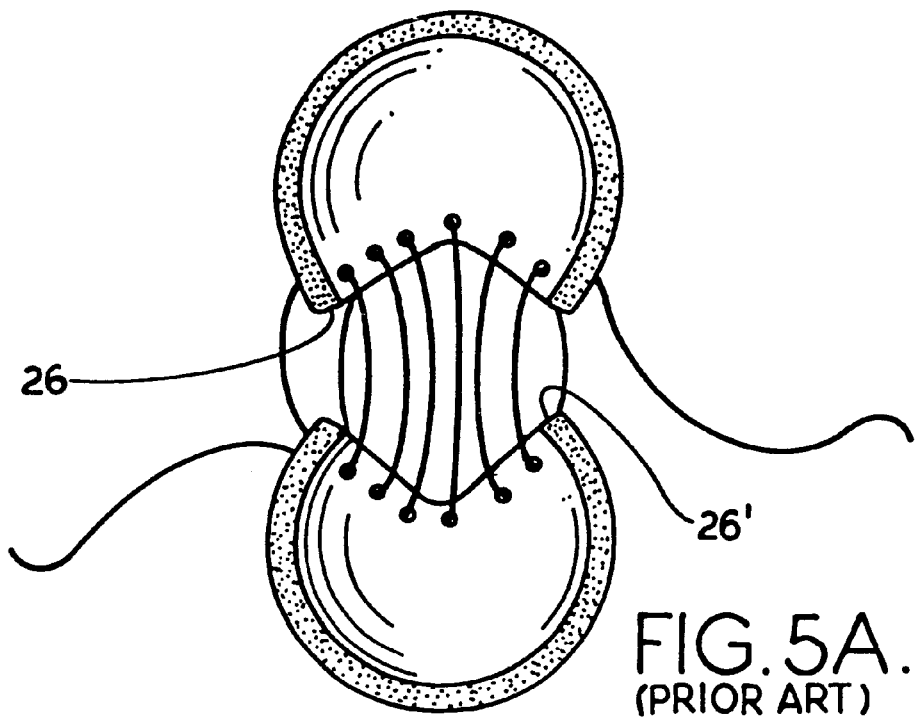
Figure 5B:
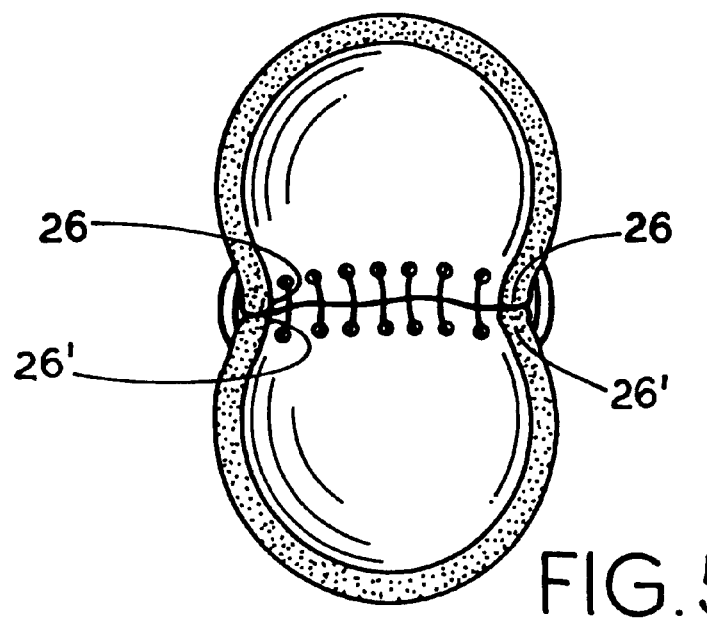
Figure 6:
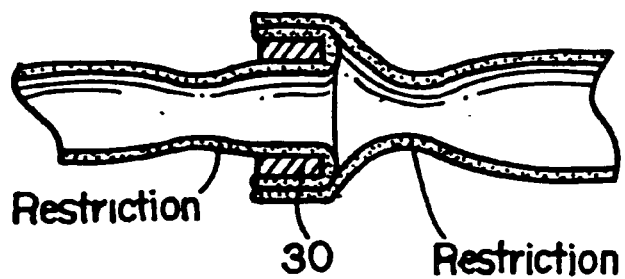
Figure 7:
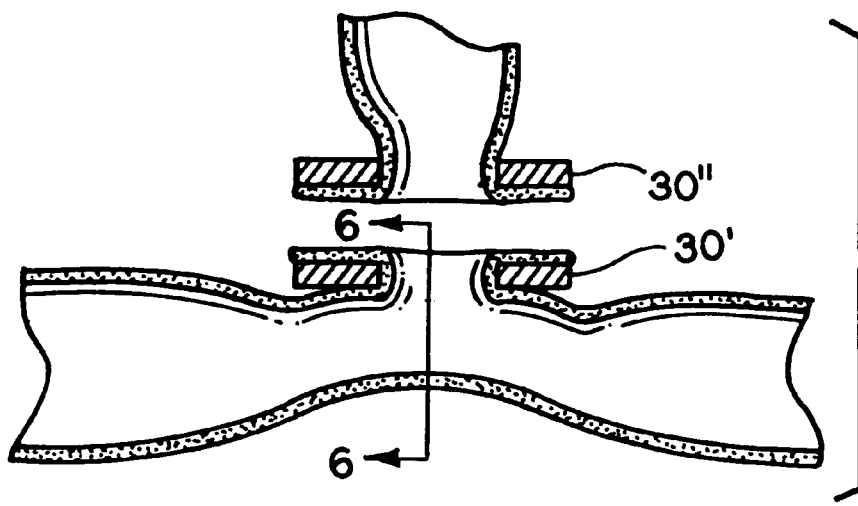
Figure 8:
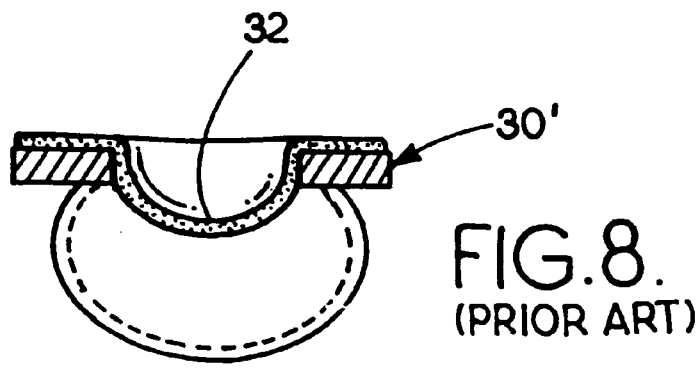

Shown in FIG. 3 is an anastomosis involving a artery 10 and a graft 12 that is performed according to the prior art. That is, an incision 14 is defined in artery 10 and a corresponding incision 16 is defined in graft 12. Sutures 18 and 20 are set near the ends (heel and toe) of the incisions. Additional sutures are set as indicated in FIG. 4 by reference numerals 1–9 and 1'–9'. Sutures are indicated at 22 and 24. Once the sutures are set, the graft and the artery are drawn together as indicated in FIGS. 5A and 5B.

Ideally, the inside edges of the graft and the artery adjacent to the incisions are placed into abutting contact with each other to promote proper healing. The inside edge of the graft vessel is indicated in FIG. 5A at 26 and the inside edge of the artery is indicated at 26' in that same figure. As can be seen in FIG. 5B, the ideal situation has inside edge 26 in abutting contact with inside edge 26' of the artery. However, as discussed above, this is not always the case. While most surgeons are extremely skillful and dexterous, hand suturing is susceptible to errors and imprecision, especially when the graft and/or artery is extremely small. In the case of a minimally invasive surgery, this precise placement may be nearly impossible.

Figure 9:
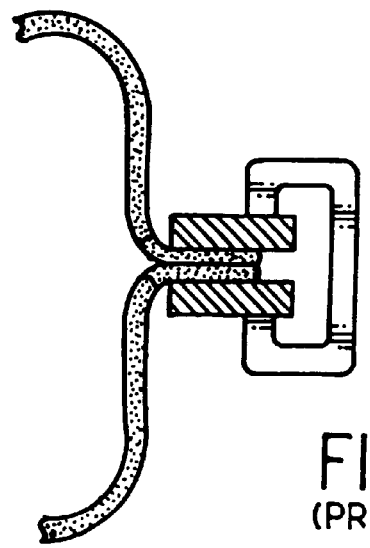

As discussed above, some prior art anastomosis techniques have used a ring to join two vessels together. This technique is indicated in FIGS. 6–9 where ring 30 is placed between two end-to-end vessels in FIG. 6 and rings 30' and 30" are used with two end-to-side joined vessels in FIG. 7. The rings serve as the means for holding the joined vessels together. However, the rings have several drawbacks, including evaginating the vessels, restricting the vessels so growth due to higher blood flow is restricted, and stretching the vessel which causes flattening of the vessel as indicated at portion 32 in FIG. 8. As discussed above, the use of rings suggests that an anastomosis is being viewed as a plumbing connection between two conduits. As was also discussed above, this is simply not the case with actual blood vessels. As discussed above, if too much clamping is applied to the vessels, necrosis may occur. Unhealthy tissue may cause scarring and in fact may fail to heal. This situation is illustrated in FIG. 9.

Therefore, the present invention is intended to permit the performance of an anastomosis in a minimally invasive manner yet to perform the procedure in an accurate manner and in a manner that promotes proper healing. The most effective healing will occur when the hemostatic medium is located on the outside of the blood vessel so any clots will form on the outside of the vessel. This basic concept is illustrated in FIG. 10 which shows an anastomotic device AD comprising a hemostatic medium HM having a stent which includes means FM for fastening the stent to the vessel and which is located on the outside of one blood vessel B1 which is to be joined to another blood vessel B2 and for bringing vessel walls, and the endothelial lining E1, of the one blood vessel into intimate approximation with other vessel walls, represented by endothelial lining E2, of the other blood vessel whereby fibrin clot FC is formed in the proper location to effect a successful procedure. Still further, excessive clamping is avoided in the present invention by obviating the need for clamps, such as are commonly used in prior art techniques.

Cuff

There are two forms of the invention, a single cuff form (see FIGS. 11–18B) and a double cuff form (see FIGS. 19–24). In the interest of brevity, this mounting element will be referred to as a cuff. However, no limitation is intended by this shorthand reference.

The single cuff form of the invention has the cuff mounted on the artery and the graft blood vessel with the vessels being brought into contact with the vessel attaching elements of the cuff to attach the two vessels together. It is here noted that for the sake of brevity, the discussion will be directed to blood vessels; however, those skilled in the art will be able to understand that the teaching can be applied to vessels of any sort that occur in a patient. Accordingly, no limitation is intended by the reference to a "blood" vessel. The double cuff form of the invention has one cuff attached to the graft and a separate cuff attached to the artery. These cuffs are then attached to each other to effect the connection. The single cuff form of the invention has a single cuff attached to both the graft blood vessel and to the artery, with the single cuff attaching the two blood vessels together to effect the connection. The double cuff form of the invention has each cuff individually mounted on a blood vessel by an instrument, and the two cuffed vessels brought together with the cuffs then coupled together.

Shown in FIGS. 11, 11A and 12 is a single cuff 40 embodying the present invention. The cuff is applied to a blood vessel and will couple that vessel to another vessel or to another cuff. The cuff can be applied to a blood vessel by an instrument while blood still flows through the vessel by using a stabilizing cuff application tool with a flow-through anvil. This enables anastomotic surgery to be performed without stopping the heart so the procedure can be carried out in a minimally invasive manner. The cuff also permits proper shaping of the junction without mishandling the blood vessels and places the two vessels in an orientation that promotes efficient healing.

Specifically, cuff 40 includes an oval shaped flexible body 42 having a long axis 44 and a short axis 46 with an oval shaped opening 48 defined therein by the cuff body central section 49. The preferred form of body 42 is a woven fabric suitable for use in surgery. A stiffening framework 50 of a retention means, such as a malleable material, is integrated into body 42 for retaining the cuff in a selected shape on a blood vessel. The preferred form of the retention means is sinuous and includes a plurality of malleable sections, such as section 52. In the present context, this element will be referred to as a retention means. However, as will occur to those skilled in the art based on the teaching of the present disclosure, depending on the context of the discussion, this element can also be referred to as a "stent" or a "stiffening band." One form of the material is a wire that is suitable for use in the surgical environment associated with this invention. The retention means has little material memory in that once deformed from one shape into another, it will not move back into the first shape from the second. A second potential form for the retainer means is shaped from flat stock which is processed using precise methods such as wire EDM or photo etching. Shaping the cuff is therefore efficiently carried out by deforming it into the desired shape after it is mounted on a blood vessel. The retention means will maintain the cuff in the shaped condition. Sections of the stiffening framework may be separate from other sections, such as quartered sections or the like.

Each malleable section has an apex, such as apex 54, with a cuff retaining pin, such as pin 56, thereon. Cuff retaining pins 56 attach the stiffening framework 50 to the cuff, and anchor means 58 attach base 60 of each section 52 to body 42 to securely anchor the stiffening framework to body 42. However, many cuff pins may be used to secure the cuff frame to the cuff.

Tissue retention pins 62 are attached at a proximal end 64 thereof to the body 42 and have a distal end 66 which engages a blood vessel to anchor the cuff to that blood vessel in the manner of a surgical staple. The instrument discussed below is used to force the retention pin into the blood vessel tissue to anchor the cuff to the blood vessel.

Means for shaping the cuff once it is anchored on the blood vessel includes docking extensions, such as docking extensions 70, having a proximal end 72 unitary with a base of a malleable section of the stiffening framework and a distal end 74 spaced from the outer perimeter 76 of the cuff body 42. An eyelet 78 is located on distal end 74 having a central hole 80 defined therein to engage a corresponding element on the instrument used to place the cuff. The means for shaping the cuff also includes a plurality of second docking extensions 82 having proximal ends 84 integral with alternate apexes of the stiffening framework 50 and a distal end 86 having an eyelet 88 with a central hole 90 for releasable connection to a corresponding element on the instrument used to place the cuff.

As will be discussed below, the docking extensions are engaged with the instrument, and once the cuff is anchored to a blood vessel, the instrument can be manipulated by the surgeon to shape opening 48 to the desired size and shape. Once the desired size and shape have been established, the cuff and framework is released from the instrument.

As can be seen in FIG. 11, the cuff has an hour glass shape in elevation, with body 42 having a first end section 92 and a second end section 94 of roughly the same outer dimension, with central section 49 having an outer dimension of less than those outer dimensions to define a waist section. Other forms of the single cuff are illustrated in FIGS. 13A–13F.

Use of the single cuff form of the invention is illustrated in FIGS. 14–18B. The tool for effecting the placement of the cuff and the coupling of the two vessels will be discussed below in connection with FIGS. 25 et seq. For present purposes, the results will be shown and discussed. As shown in FIG. 14, after the graft vessel G and the artery A have been prepared, the cuff is placed on the artery A. The graft vessel is then moved into proximity of the cuff as shown in FIG. 14 and joined to the cuff as shown in FIGS. 15 and 16.

As can be seen by comparing FIGS. 18A and 18B, once the cuffs are attached to the blood vessels, the blood vessels are brought together to form the desired connection, and then are shaped so the desired amount of abutting contact is formed between the two adjacent inside blood vessel edges. To effect the desired amount of abutting contact between the inside edges of the blood vessels, the single cuff form of the invention can include a means, such as bridge means 110 shown in FIGS. 18A and 18B to draw the adjacent blood vessel inside edges 26 and 26' together into abutting contact from the spaced positioning of these two edges shown in FIG. 18A to the abutting contact shown in FIG. 18B. Bridge means 110 includes a malleable wire 112 or extensions 70, 82, etc. that has essentially no material memory similar to that situation discussed above with regard to the stiffening framework 50. Thus, when bridge wire 112 is deformed from the FIG. 18A configuration to the FIG. 18B configuration, it will retain the FIG. 18B configuration thereby placing the inside edges 26 and 26' in abutting contact with each other. Deformation of wire 112 can be effected with a proper tool. The bridge can also be formed from shaping pins resistance welded together.

It can also be understood from this disclosure that as the edges of the vessels are brought into intimate contact, there is a defined junction angle noted by JA in FIG. 18B. This angle varies continuously with respect to a linear reference, such as the longitudinal centerline of the vessels at the junction, as a unit vector associated with the angle follows around the periphery at the anastomotic junction. The means and method of the present invention permits this variation in angle. This variation in junction angle effects a properly shaped anastomosis for dissimilarly sized vessels. This angle will also vary at the heel and the toe depending on the appropriate angle of the graft vessel, as shown in FIG. 44 at JA', JA" respectively.

By way of reference, a single cuff side-to-side anastomosis is shown in FIG. 17.

The double cuff form of the invention is illustrated in FIGS. 19–24. As can be seen (see, e.g., FIG. 21), one cuff 40' is attached to a graft blood vessel G, and a second cuff 40" is attached to the artery A. As can be seen in FIG. 19, there is a spacing between the fastening means attaching the cuff to the vessel and the edge of the artery. This spacing is selected so the loose edge of the vessel can still be controlled, but the fastening means is not located too close to the edge of the vessel. Bringing the cuffs together in this manner does not mishandle the blood vessels and promotes efficient healing of the junction. A spacing of ½ mm to 1 mm is shown in FIG. 19. However, this spacing is disclosed for the sake of completeness and is not to be taken as limiting.

Means for joining one cuff to the other in the double cuff form of the invention includes one unit 98 fixed to the graft (cuff) blood vessel G and one unit 99 fixed to the artery (cuff) A. As shown in FIG. 19, a female element 100 is fixed to cuff 40' and a corresponding male element 102 is fixed to cuff 40". Female element 100 includes an eyelet 104 that has an opening sized and shaped to snugly receive male element 106 mounted on element 102 to establish a friction fit between elements 100 and 102 that securely couples the two cuffs together. The preferred form of the cuff joining means includes four male elements and four female elements on each base 98 and 99, each being located on opposite sides of the cuffs as is shown in FIGS. 22 and 23. Each cuff has two male elements and two female elements with the male elements on each base whereby a secure attachment is effected.

As can be understood by those skilled in the art by comparing FIGS. 21 and 16, the double cuff form of the invention uses two cuffs, such as 40' and 40", to attach two blood vessels together, whereas, the single cuff form of the invention uses a single cuff 40''' to attach two blood vessels together. The double cuff form of the invention has two similar cuffs attached together by a coupling means. The single cuff form of the invention has a single cuff with the two ends thereof identical each having a stiffening framework therein and each having tissue retention pins 62''' therein. A single body unitary 42''' forms the cuff 40'''.

Both forms of the invention, the single cuff and the double cuff, can be used to form both a side-to-side anastomosis and the double cuff form can be used to form an end-to-side anastomosis.

The double cuff form of the invention is applied as indicated in FIGS. 19–23. A tool, which will be discussed below in connection with FIGS. 24 et seq, is used to place a cuff on the graft, and then a second cuff on the artery. The vessels are then oriented adjacent to each other as indicated in FIG. 19, and then brought together so the two cuffs are coupled as indicated in FIG. 20. The cuffs are then coupled together as indicated in FIG. 21 to form an end-to-side anastomosis as indicated in FIG. 22 or to form a side-to-side anastomosis as shown in FIG. 23. The two cuffs are coupled together by a suitable fastener, such as the above-discussed male/female coupling shown in FIG. 21.

An alternative form of the cuff joining means for the double cuff form of the invention is shown in FIG. 24. This form of the cuff joining means includes rivets or staples 114 in place of the male and female elements discussed above. The rivets or staples are placed in bases 98 and 99 and hold the bases together in the manner discussed above for the male and female elements 104 and 106.

Instrument

As discussed above, the anastomosis technique of the present invention is intended to be performed in a minimally invasive manner. Therefore, the cuffs discussed above must be placed on blood vessels that are located inside a patient, with the artery carrying blood. As was also discussed above, the anastomosis technique of the present invention may involve extremely small blood vessels. Accordingly, the instrument used to effect the anastomosis must be very accurate and precise, yet will not mishandle the blood vessels during performance of the technique. The instrument will place a cuff on the artery while permitting blood to flow through that artery, and then will place a corresponding cuff on the graft blood vessel, or will attach the graft blood vessel to the single cuff mounted on the artery in the single cuff form of the invention. The instrument will then be used to shape the cuffs so the junction is the most efficient and will permit proper healing. All of this must be carried out in a minimally invasive manner.

The preferred form of the instrument used to mount a cuff to the artery in both forms of the invention and to mount the cuff to the artery and to the graft in the double cuff form of the invention is shown in FIGS. 25–29, with FIG. 25A showing a cuff in conjunction with the instrument. Instrument 120 broadly comprises a handle frame 122 having a handle 124 that is grasped by a surgeon during operation of the instrument, and a finger frame 126 having a finger grip 128 which is operated by the surgeon, two driver elements 130 and 132 pivotally attached to the handle frame, a graft anvil 134 and an artery anvil 136.

More specifically, in FIG. 25A, handle frame 122 includes a U-shaped section having legs 140 and 142 attached at one end to handle 124 and which are spaced apart to define a channel 144 therebetween. Each leg has an inside surface 146 with L-shaped anvil alignment slots 148 and 150 defined in the legs to have short legs 151 that intersect the channel and long legs 154 defined to be parallel to the channel. The function of the anvil slots will be understood from the following discussion.

The handle frame further includes two ears 156 and 158. The ears include two spaced apart plates 160 and 162 with bores 164 and 166 defined in each plate to be centrally aligned with each other for a purpose that will be understood from the discussion. The handle frame further includes two rails, such as rail 170, on the outer edges of the legs 140 and 142.

An undercut region 174 is defined in the proximal end of the handle frame with a top shoulder 176 defined therein at the top entrance to channel 144. Shoulder 176 is U-shaped and has a channel 178 defined between leg 180 corresponding to leg 140 and leg 182 corresponding to leg 142.

Finger frame 126 includes a U-shaped base 184 having two legs 186 each connected to a center section 190 and defining a channel 192 therebetween. A slot 194 is formed at the intersection of each leg and the center section, with slots 194 being sized and located to slidably receive rails 170. Sliding engagement between the rails and the slots permits the finger frame to move with respect to the handle frame longitudinally of the channel 190 as is indicated by the double-headed arrow 196, with handle frame 122 moving in direction 198 with respect to finger frame 126 to open the instrument anvils and moving in direction 199 with respect to the finger frame to close the instrument anvils as will be discussed below.

Each leg 186 of the finger frame 126 further includes an ear, such as ear 202 on a distal end thereof to which a guide pin, such as guide pin 204, is fixed to extend past the handle frame leg adjacent thereto.

Instrument 120 further includes two pivot pins 206 and 208 accommodated in the aligned bores 164 and 166. Each of the driver arms 130 and 132 has a pivot pin receiving hole 210 and 212 respectively defined in the proximal end of arms 214 and 216 respectively. A crescent-shaped driver element 218.and 220 is located on the distal end of each arm 214 and 216 respectively with a cam slot 222 and 226 being defined in the arms 214 and 216 respectively.

The arms are pivotally attached to the handle frame by the pins 206 and 208 to move in directions 226 and 228 as indicated by double-headed arrow 230 when finger handle 126 moves directions 198 and 199 respectively to open and close the driver heads 218 and 220. Slots 222 and 226 slidably receive guide pins 204 to effect this opening and closing movement. Since the driver arms are fixed at an angle to handle frame 122 by pivot pins 206 and 208 and guide pins 204 move longitudinally with respect to the handle frame and slidably engage cam slots 222 and 226, longitudinal movement of the finger frame with respect to the handle frame will cause the above-mentioned pivotal movement of the anvil arms. The opening and closing of the driver arms is illustrated in FIGS. 27 (closing) and 28 (opening).

Each driver head, 218, 220 has a V-shaped cuff-engaging edge, such as edge 232 which is sized and shaped to engage the waist section 49 of a cuff. Each edge 232 also has two surfaces 234 that diverge away from each other from the edge 232 to engage surfaces 236 and 238 (see FIG. 11) respectively of the cuff sections 92 and 94. Engagement of the surfaces 234 and 236, 238 along with a movement of the anvils 136 and 134 forces the tissue fasteners 62 into the tissue of the blood vessel while shaping the cuff to the blood vessel.

The tissue fasteners must be turned in the manner of a staple in order to fully connect a cuff to a blood vessel. Accordingly, instrument 120 includes artery anvil 136 and graft anvil 134 which are removably fixable to the handle frame. Graft anvil 134 includes a body 240 having a threaded portion 242 on a proximal end thereof, a graft anvil head 244 on a distal end thereof and alignment pins 246 between the two ends thereof. A fastening knob 247 is also included with instrument 120, and is internally threaded to threadably engage threaded portion 242.

Knob 247 is accommodated in undercut area 174 and threaded portion 242 extends through channel 178 to be engaged by the threaded portion of the knob 247. Longitudinal movement of the graft anvil in directions 260 and 262 is effected by threading the knob 247 on the threaded portion 242. Threaded movement in one direction moves the graft anvil in direction 262 and threaded movement in the opposite direction moves the graft anvil in direction 260 whereby the location of the graft anvil head 244 with respect to the driver elements 218, 220 can be adjusted and set. The purpose of this movement will be understood from the discussion in this disclosure.

A groove in knob 247 engages shoulder 176 of handle 122. Since knob 247 remains stationary the anvil moves up or down to bend or cinch the fasteners 62. Body 240 includes a first portion 248 and a second portion 250 that is angled with respect to the first portion 248. Graft anvil head 244 has a proximal end thereof fixed to portion 250 to extend transverse to longitudinal centerline 252 of the body 240. The length of body 240 as measured between its proximal and distal ends is greater than the length of the handle frame as measured along its longitudinal centerline 254 between the shoulder 176 and distal end 256 whereby graft anvil head 244 is spaced from distal end 256 when the graft anvil 134 is mounted on the handle frame. Arm 248 is also long enough so that graft anvil head 244 is also spaced from driver heads 218 and 220 when the graft anvil is in place on the handle frame. Alignment pins 246 are received through anvil slots 148 and 150 and are slidably accommodated in slots 154 so the graft anvil is securely and movably affixed to the handle frame.

Artery anvil 136 includes a body 270 having a threaded portion 272 on a proximal end thereof and an artery anvil head 274 on a distal end thereof. Alignment pins 276 are located on the body to be received through alignment slots 152 and slidably accommodated in slots 154 on the handle frame. When the artery anvil is attached to the handle frame, threaded portion 272 extends through channel 178 and is threadably received by knob 247 to attach the artery anvil to the handle frame and to move that artery anvil in directions 260 and 262 with respect to the handle frame as was discussed above with regard to the graft anvil whereby the location of the artery anvil head 274 with respect to the driver heads 218, 220 can be set. The artery anvil head 274 is located beneath the driver heads so that the head can be inserted into an artery and a cuff being supported by the driver heads will be located outside that artery. Once the artery anvil head is positioned inside an artery, the knob 247 is operated to move the anvil head 274 toward the driver heads 218, 220 until the cuff supported in the heads 218, 220 engage the outside of the artery. The tissue retention pins can then be set.

Artery anvil head 274 includes a bullet shaped body 280 having two ends 282 and 284 with a bypass channel 286 defined longitudinally therethrough from one end 282 to the other end 284. This channel permits blood flow through the anvil head maintaining perfusion while the cuff is being attached. A fastener turning section 288 is defined in top surface 290 of the head 274 adjacent to the intersection of the head and the body 270 and in a location to receive ends 66 of the tissue fastening pins when they are forced through the blood vessel wall. The fastener turning section is concave so the pin is turned as it engages and follows the anvil head surface adjacent to the turning section. This rotates the fastener end so the fastener is gradually bent from the FIG. 27 shape to a curved shape shown in FIG. 28, for example. The tissue fastener is forced to follow this turning section by engagement of the driver head surface against the cuff and against the fastener body 62 as the heads 218, 220 are moved into engagement with the cuff by operation of the finger frame 126 and as the artery anvil is moved in direction 260 by operation of the knob 247 on threaded portion 272.

Driver heads 218, 220 include docking pins 294 which releasably engage holes 80 and 90 of the docking extensions 70 and 82 on the cuff to control the shape of the cuff. The friction fit between pins 294 and the extensions 70 and 82 is great enough to permit the cuff to be pulled and shaped by movement of the driver heads, but low enough so the pins 294 can be pulled out of the docking extensions without pulling the cuff off of the blood vessel. Alternatively, pins 294 could be retracted through a flexible shaft connected up to the handle. Pulling the driver heads outwardly in direction 226 will enlarge the junction and will change its shape from oblong toward circular. Therefore, a surgeon can shape the junction in the manner that is most efficient to healing and to defining an effective anastomosis.

An assembled instrument is shown in FIG. 26 with an artery anvil being inserted through an incision I in an artery A and a cuff 40 on the driver elements. As can be seen, once the incision is made, the artery anvil head is button holed into the artery via the incision. The anvil head is actually larger than the incision in the artery but can be angled through the incision into position as shown in FIG. 26. The knob 247 is operated to draw the anvil head and vessel surface at the incision up toward heads 218, 220. This action also isolates the working area from motion associated with the beating heart. As indicated in FIG. 27, after the head supported cuff contacts the outside of the artery, driver heads 218, 220 are operated to force the edges 232 against the waist 49 and against the surfaces 236 and 238, and the knob 247 is further operated to draw the anvil and the cuff together. Further operation of the knob 247 forces the tissue fasteners through the blood vessel tissue, into turning section 288 and around on themselves in the manner of a staple whereby the cuff is fixed to the blood vessel. During this operation, blood flows through the artery via channel 286. Once the cuff is attached to the artery, the driving heads 218, 220 are opened as shown in FIG. 28 so the anvil head 280 can be removed from the artery. Since the cuff is connected to the driver heads, opening the driver heads will enlarge the incision thereby permitting the artery anvil to be removed.

The graft vessel is prepared in a similar manner. The graft anvil is inserted into the graft blood vessel via the end of that blood vessel and is tied to the graft anvil head 244 with a garroting suture. The graft anvil 134 is attached to handle frame 122. The instrument is operated to attach a cuff to the graft blood vessel in a manner similar to that just described for attaching a cuff to the artery. Actually, the graft is prepared first because the surgeon has more time to work on the graft than on the artery. The graft anvil allows the surgeon to prepare the graft on the anvil first and then attach the anvil to the instrument at a later time when it is convenient to do so.

The instrument is then maneuvered so the graft blood vessel is adjacent to the cuff mounted on the artery. The knob 247 is then operated to force the graft blood vessel into contact with the cuff portion that is not attached to the artery to attach the graft vessel to the artery attached cuff. As shown in FIG. 29, the graft anvil head has a fastener turning section 296 which operates to turn the fasteners in that section of the cuff in a manner identical to the above-described turning of the fasteners in the artery. This is illustrated in FIG. 29 for a single cuff embodiment. Turning section 296 is used to turn the tissue retention pins to either attach a single cuff to the blood vessel or to attach a separate cuff to the blood vessel. Once the cuff is attached to the graft (for the single cuff embodiment), or the cuff on the graft is attached to the cuff on the artery (for the double cuff embodiment) by attaching the coupling elements 106 and 104 (for the double cuff form) or the bridges 110 are manipulated to bring the inside edges 26 and 26' of the vessels together, the driver heads 218, 220 are manipulated to enlarge the graft incision to permit the graft anvil head to be withdrawn from the graft vessel via the end of that vessel. The driver heads can then be further manipulated to size and shape the junction, and then manipulated to remove the docking extensions 70 and 82 from the anvil pins 294 to release the cuff or cuffs from the instrument. The garrot suture is cut and the graft anvil is removed from the graft. The graft blood vessel is then tied off and the anastomosis is complete.

Instrument for Mounting a Cuff on the Graft Artery

Shown in FIGS. 31–34 is one form of an instrument used to mount a cuff on a graft artery. An alternative form of the instrument is shown in FIGS. 35–37.

As shown in FIG. 30, a graft G is prepared by defining an incision I therein. The graft has been removed and is being prepared and cuffed outside of the patient..An instrument 300 is shown in FIG. 31 and includes tongs 302 and 304 having cuff-engaging ends 302' and 304' respectively, and handles 302" and 304" respectively which are gripped by the surgeon. A pivot 306 is located at the intersection of the tongs. Each of the tongs has a cutout portion which conforms to one-half of the shape of a cuff whereby a cuff will be securely held in the tongs as indicated in FIG. 31. Elements 106'" are located on the tongs to engage the female elements on the cuff to hold the cuff in position on the tongs. As can also be seen, each tong has a cutout section 310 for engaging anvil 312 shown in FIG. 32.

Anvil 312 includes a central section 314 having an opening defined in a top section 316 thereof. A section 318 includes two side sections 324 and 322, each of which has a cutout, such as cutout 326 in side 322, defined therein. Anvil 312 further includes a threaded element 328 extending through the opening defined through top section 316 and is pivotally attached to section 318 at 329. Threaded element 328 is threadably received through a threaded opening 326' defined through section 336. A knob 330 is unitary with the threaded element 328. Rotation of the knob moves top section 318 relative to arms 334 as indicated by double-headed arrow 332. Arms, such as arm 334 have top section 336 engaging the threaded element 328. Movement of the threaded element causes the hook sections 338 to move into and out of the cutouts.

As shown in FIG. 33, graft G is drawn upwardly through the cuff mounted on instrument 300 to located edge GE above the cuff, and above the fasteners 66 of the cuff. Then, as indicated by arrow 340, anvil 312 is moved to orient hooks 338 in cutouts 310. This condition is shown in FIG. 34.

Side sections 322 and 324 are unitary, and each includes a fastener turning area 343 and 345 located to engage fastener 66 when the anvil is operated.

After the anvil is engaged with the instrument 300, movement of the threaded element forces elements 322 and 324 downwardly until turning areas 343 and 345 engage the ends of fasteners 66. Further movement of the elements 322, 324, turns fasteners around to attach the cuff to the graft vessel in the manner of a staple. Once the cuff is secured to the vessel, the anvil is released, and the cuff and attached vessel removed from the instrument 300. As will be understood from the above discussion, the fasteners 66 are evenly turned by the anvil to evenly mount the cuff to the graft. The cuffed graft can then be laid aside until it is needed.

An alternative form of an instrument used to mount a cuff on a graft is shown in FIGS. 35–37. The graft is prepared in the manner discussed above.

End cuff attaching tool 350 includes a housing 352 having a forming cavity 354 defined therein to extend from end wall 356 adjacent to edge forming elements 358 and 360. Housing 352 is slidably mounted on plate 362 by a track 363 to be moved by hand pressure in directions 363' and 363". Housing 364 is mounted on plate 362 and slidably receives a pushrod 366. Pushrod 366 has a link 368 attached at one end thereof by a pivot pin 370. Pushrod 366 can be operated by hand to move in directions 372 and 374 as indicated by double-headed arrow 376.

A tilt table 380 is pivotally attached to the plate 362 by pivot pins, such as pin 382, and is pivotally attached to the link 368 by pin 384. As can be seen in FIG. 35, movement of the pushrod in direction 374 tilts the table in direction 386 about pin 382, and vice versa for pushrod movement in direction 372. The table moves from the position shown in FIG. 35A to the position shown in FIG. 35C under the influence of this pushrod movement.

A vessel receiving element 390 is mounted on one end of the plate 362 to extend upwardly and outwardly therefrom at an angle as shown in FIG. 35. Table 380 includes a cutout section 392 which receives a cuff with cuff toe 394 on top and cuff heel 396 on the bottom. Table 380 includes alignment pins 398 that are received in alignment holes 400 on the cuff, and alignment holes 402 that receive alignment pins 404 on the cuff to releasably secure the cuff to the table.

Figure 36A:
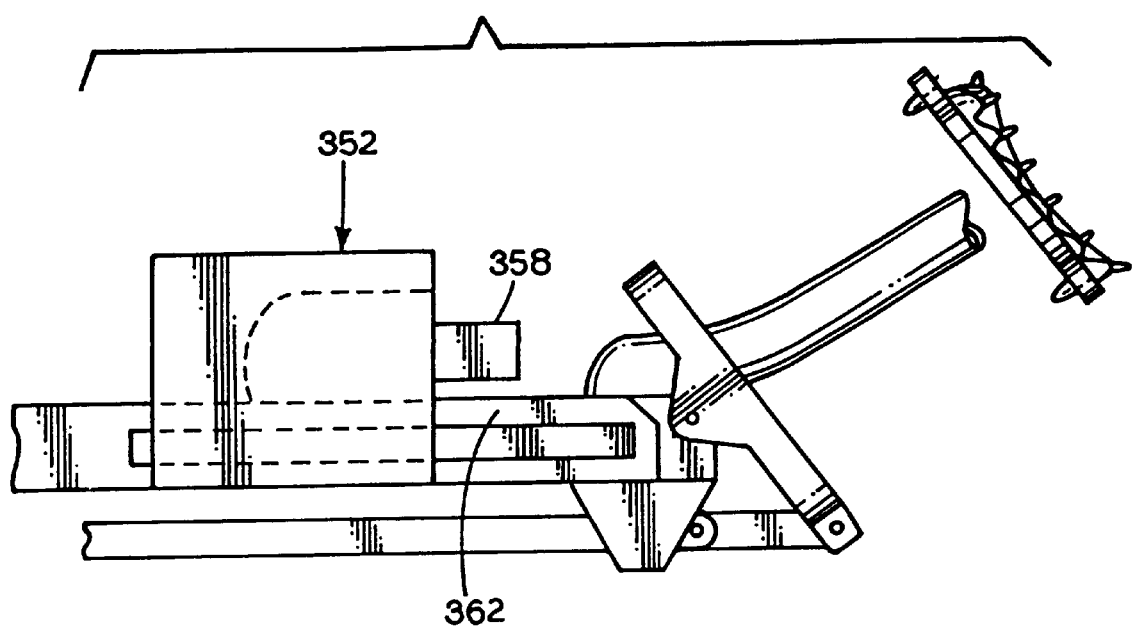
Figure 36B:
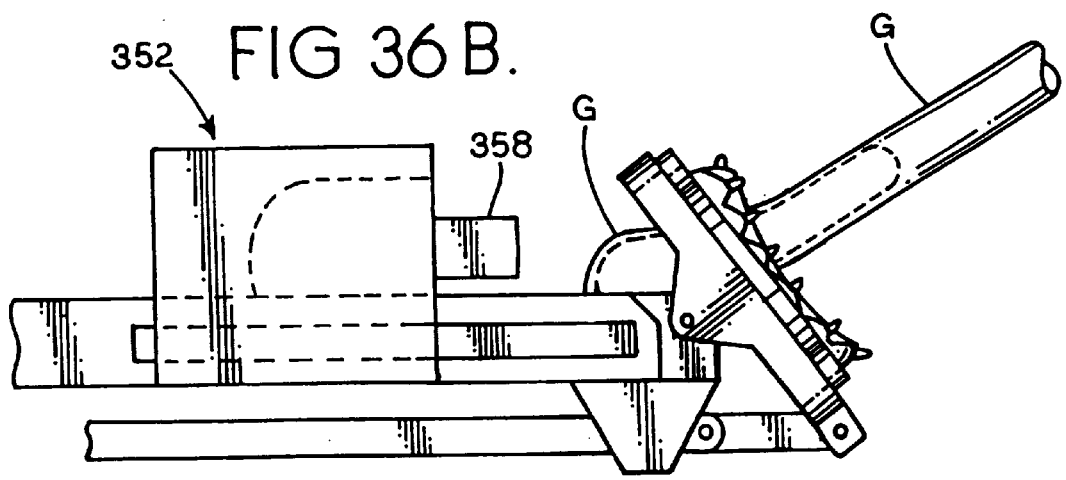
Figure 36C:
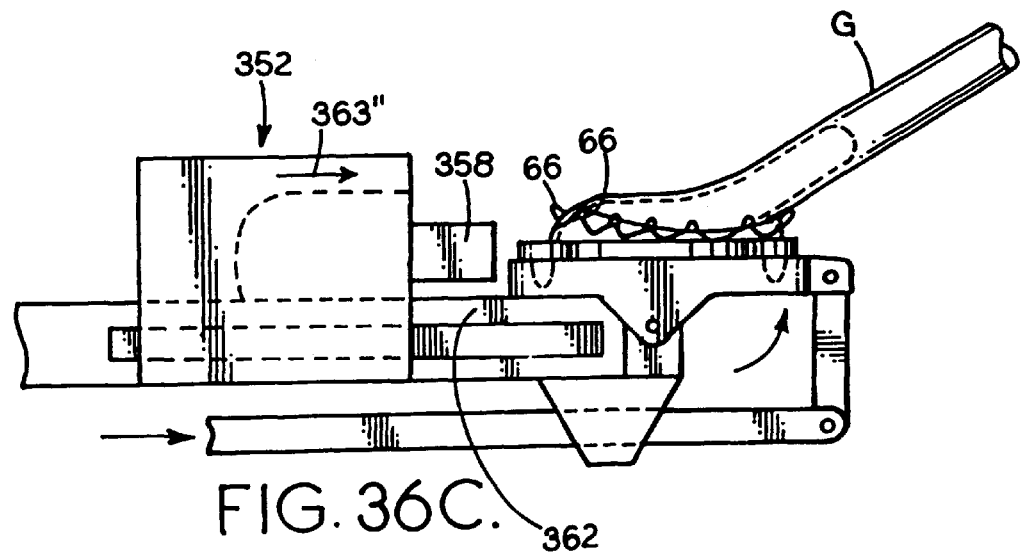
Figure 36D:
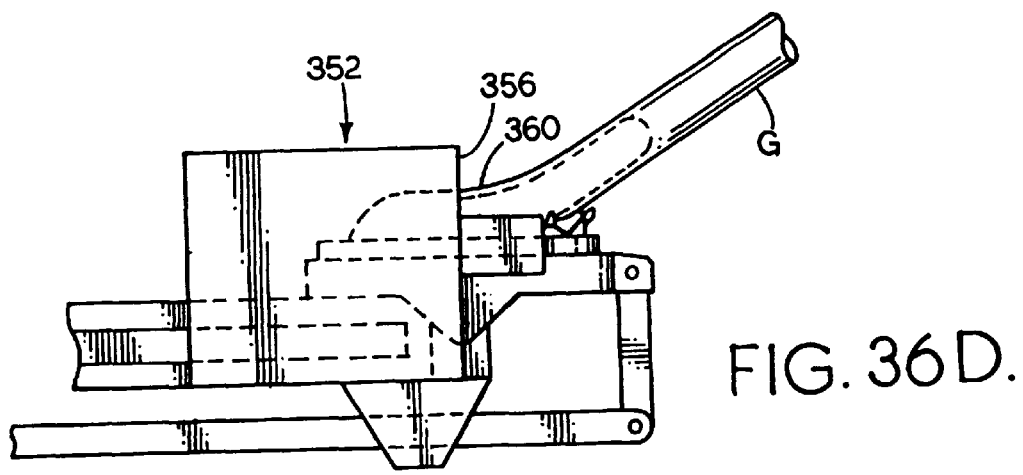

As can be seen in FIG. 35, shaft 390 will extend through the cuff-receiving section 392 and through the cuff mounted on the table. Graft G is placed over the shaft to extend through the cuff with end 406 attached to hooks 408 on the table to temporarily mount the graft to the instrument plate 362. Operation of the pushrod tilts the table in direction 386 to bring the cuff down on top of the graft as can be understood from FIGS. 36A, 36B and 36C. Once the cuff is in place as shown in FIG. 36C, the housing 352 is moved toward the end of the table in direction 363″ as shown in FIGS. 36C and 36D. The cuff and graft are guided into cavity 354 and the front end of the cuff and graft engage the end of the cavity as indicated in FIGS. 36D and 37. The shaft 390 includes fastener turning areas, such as area 410 and the turning movement of the table forces cuff fasteners through the graft and into engagement with the shaft at the turning areas. Further turning movement of the table turns the fasteners to couple the cuff to the graft. Movement of the housing 352 in direction 363″ engages J-shaped fastener 66′ with the housing and forces that fastener through the graft and into turning area 410. Further movement of the housing turns the fastener to couple the cuff to the graft. Once the J-shaped fasteners are coupled to the graft, the cuff is coupled to the graft and the housing can be moved in direction 363′ and, table 380 moved opposite to direction 386. The cuffed-graft can then be removed from the shaft 390. The J-shape of fasteners 66′ prevents the graft vessel from becoming damaged from otherwise protruding pins from the cuff as the tilt-table is being rotated. The variation in shape of the fasteners thus protects the graft vessel.

As before, once the graft vessel is cuffed, it can be set aside until the artery is cuffed.

Instrument for Coupling One Cuff to Another

Shown in FIGS. 38–40 is an instrument that can be used to couple one cuff to another in the double-cuff form of the invention. As shown in FIG. 38, instrument 450 is releasably attached to a vessel-mounted cuff, and is then operated to attach that cuff to another vessel-mounted cuff. One cuff can be attached to an artery using the instrument shown in FIG. 25 (using elements 130, 132 and 136) while a cuff can be attached to a graft using the instrument shown in either FIG. 31 or FIG. 35 in an end-to-side anastomosis, or using the instrument shown in FIG. 25 twice (using elements 130, 132 and 136 to attach a cuff to an artery and using element 134 to attach a cuff to a graft) in a side-to-side anastomosis.

The two cuffs are attached together using instrument 450 shown in FIG. 38. Instrument 450 includes a handle 452 having a hand-grip 454 on one end thereof. A trigger housing 456 is mounted adjacent to the hand grip. An anchor element 458 is also mounted on the handle adjacent to the hand grip. A cuff engaging section 460 is mounted on the other end of the handle and includes a base 462 having a forward end 464 and an aft end 466. Cuff engaging C-shaped hooks 468 are pivotally mounted on the base section by pivot bars, such as bar 470 extending through the hooks so the hooks pivot in directions 472 and 474. Clamping hooks 476 and 478 are also pivotally mounted on the base section by bars 470 to move in the directions 472 and 474. Hooks 468 are spring biased in direction 474 by springs, such as spring 480 and hooks 476 and 478 are fixed to bar 470 for rotation therewith. Hooks 476 include cutout portions, such as portion 482. It is noted that a hook 478 is not shown in FIG. 38 but is located on the base diametrically opposite to hook 478. Hooks 468 clamp instrument 450 to the cuff, and hooks 476 and 478 force the male fastening elements such as element 106 of one cuff through female elements, such as element 104, of the other cuff. For this reason, hooks 476 include a cutout section to accommodate the male element, whereas hooks 478 do not include a cutout section as these hooks engage the female elements.

The hooks are operated by hand. As shown in FIG. 38, hooks 468 are operated by mechanism 490 which includes a tether 492 attached at one end thereof to element 458 and at the other end thereof ears 494 on each hook 468. Tether 492 extends through guide 496 which is located between the ears 494. Therefore, movement of element 458 in direction 498 draws ears 494 together in directions 500′ and 500″ against the bias of springs 480. The springs tend to move the hooks into cuff engaging positions, such as shown in FIG. 39, and the tether is operated to release tool 450 from the cuff. The tool 450 is shown attached to a vessel mounted cuff in FIG. 39.

Hooks 476 and 478 are operated by a system 504 which includes a tether 506 attached at one end thereof to the trigger housing 456 and at the other end thereof to levers 506. The tether extends through guides 508. Levers 506 are pivotally mounted on the base section by pins 510 to move in direction 512 when the trigger housing is moved in direction 514. The pivot pins 510 are fixed to rod 470 to rotate that rod in direction 512 with the levers. Hooks 476 and 478 are fixed to the rod 470 for rotation therewith, and rotation of the levers in direction 512 rotates the rod 470 in direction 516. Rotation of the hooks 476 and 478 in direction 516 moves those hooks from the FIG. 38 position to the cuff engaging position shown in FIG. 40. Rod 470 is also spring biased by a torsion spring, so when the trigger housing is released, that rod will rotate to release hooks 476 and 478 back into the FIG. 38 position.

After the tool is mounted to a cuff, that cuff is attached to the other cuff. The cuff and tool are moved adjacent to the other cuff, as shown in FIG. 39, and the two cuffs are brought together and coupled as above described.

Method

FIGS. 41, 42A and 42B represent the method of using the above-described instrument in performing an anastomosis according to the teaching of the present invention.

The following steps are used to effect the anastomosis of the present invention in the single cuff method.

The location of the anastomosis is determined.

The graft is pulled onto the graft anvil.

The graft is garroted to the graft anvil.

The graft and graft anvil are set aside.

Perform arteriotomy.

Button-hole artery anvil into interior lumen of the artery.

Dock the artery anvil to the instrument.

Cinch the fasteners joining the cuff to the artery.

Operate the instrument to open the arteriotomy to full length.

Open the driver heads and bend shape the cuff.

Detach the artery anvil from the instrument and remove the artery anvil from the artery.

Close the drivers to accept the graft anvil.

Dock the graft anvil to the instrument.

Cinch the fasteners joining the cuff to the graft (single cuff form), or the cuff on the graft to the cuff on the artery (double cuff embodiment)

Release the graft garret.

Release the graft anvil from the instrument and tie off the graft end.

Open the shape of the anastomosis with the instrument.

Release the instrument from the cuff or cuffs.

The double cuff technique is shown in FIG. 42A for a side-to-side anastomosis and in FIG. 42B for an end-to-side anastomosis.

It should also be understood that while the hemostatic medium is shown in the preferred embodiments, there may be certain uses, such as mentioned above, of the device that will not require the hemostatic medium. The joining at lumens like fallopian tubes is one example. It is therefore contemplated that this disclosure will cover an anastomosis means and method which omits the hemostatic medium. One example of this hemostatic medium-less anastomosis is shown in FIG. 43 in which the tissue pins are staggered in a manner that allows the approximation of the tissue in a sinuous junction line. This will mimic the type of approximation that sutures provide by interweaving from one side to the other. The sinuous junction SJ is shown in FIG. 43 as tissue pins attached to an external malleable stent S. Tissue is shown as T.

It is further possible at that point to join the two stents with materials that are flexible but which still hold the edges in approximation creating a living hinge between the two stents. The junction SJ will thus be a living hinge about which the two vessels can pivot or move. FIG. 43 shows a single cuff design with only one bridge being shown for the sake of clarity of disclosure, it being understood that other bridges, as discussed above, are also included in the FIG. 43 embodiment. A double cuff design is shown in FIG. 45, with only one coupling element being shown.

Although this invention has been disclosed and illustrated to show the anastomosis of small distal grafts, there are other surgical procedures that will benefit from this type of improvement as will occur to those skilled in the art based on the teaching of this disclosure. For example, a proximal graft attachment to aortic supply, an anastomosis of other luminal structures such as, but not limited to, Fallopian tubes urethra, ureter, bile ducts, etc. can also be performed using the means and method disclosed herein.

FIG. 46 shows the use of the present means and method as applied to multiple grafts. As above discussed, where an existing blood supply conduit, such as the IMA, is not available to use, an artificial supply vessel must be grafted. Usually another vessel such as the saphenous vein is harvested from the patient's leg. At this point, the graft must be attached to a supply. This is usually the aorta AA. In the area above the aortic valve, a proximal anastomosis P is performed using the techniques discussed above to attach the new supply conduit to the aorta. The means and method discussed above is used to perform this procedure. The means and method discussed above is also used to attach the jump graft JG in an end-to-side manner ES in addition to the side-to-side manner SS shown. Multiple grafts are thus effected using the teaching of the present invention. As will be understood by those skilled in the art based on the teaching of to the present disclosure, any vessel that needs to be by-passed or joined use the techniques of this invention.

In addition, it is understood that while the invention is particularly well suited for endoscopic use, it is in no way limited to such application. This invention will work equally well in an "open" surgical setting. Accordingly, these situations are intended to be included in the scope of the present invention.

It is understood that while certain forms of the present invention have been illustrated and described herein, it is not to be limited to the specific forms or arrangements of parts described and shown.

We claim:

1. A method of performing an anastomosis comprising:
   A) defining an incision in a first vessel;
   B) defining an incision in a second vessel;
   C) positioning a first mounting structure on the first vessel adjacent to the incision in the first vessel so that an inner edge of the first vessel adjacent to the incision therein is spaced from an inner edge of the first mounting structure;
   D) fastening the first mounting structure to the first vessel;
   E) positioning a second mounting structure on the second vessel adjacent to the incision in the second vessel so that an inner edge of the second vessel adjacent to the incision therein is spaced from an inner edge of the second mounting structure;
   F) fastening the second mounting structure to the second vessel; and
   G) attaching the first and second mounting structures together.

2. The method defined in claim 1 wherein the step of attaching the first and second mounting structures together includes positioning the inner edges of the vessels in abutting contact with each other after said attaching steps.

3. The method defined in claim 1 further comprising a step of positioning the vessels in side-to-side orientation prior to said attaching step.

4. The method defined in claim 1 further comprising a step of positioning the vessels in end-to-side orientation prior to said attaching step.

5. The method defined in claim 1 further comprising a step of maintaining blood flow through one of the vessels.

6. The method defined in claim 1 further comprising a step of drawing the vessels together.

7. The method defined in claim 5 further comprising a step of stabilizing the first vessel.

8. The method defined in claim 5 further comprising a step of positioning the inside edges of each vessel in abutting contact with each other.

9. The method defined in claim 1 further comprising a step of shaping the fastened mounting structures to define a desired flow area between the first and second vessels.

10. The method defined in claim 1 further comprising a step of shaping the fastened mounting structures to define a flow area which exceeds a cross sectional area defined by one of the vessels prior to said attaching step.

11. A method of performing an anastomosis comprising:
    A) defining an incision in a first vessel;
    B) defining an incision in a second vessel;
    C) positioning a mounting structure on the first vessel adjacent to the incision in the first vessel so that an inner edge of the first vessel adjacent to the incision therein is spaced from an inner edge of the mounting structure;

D) fastening the mounting structure to the first vessel;

E) positioning the second vessel adjacent to the mounting structure so that an inner edge of the second vessel adjacent to the incision therein is spaced from an inner edge of the mounting structure;

F) fastening the mounting structure to the second vessel; and

G) shaping the fastened mounting structure to define a desired flow area between the first and second vessels.

12. The method defined in claim 11 further comprising a step of positioning the inner edges of the vessels in abutting contact with each other prior to said shaping step.

13. A method of performing an anastomosis comprising:
A) defining an incision in a first vessel;
B) defining an incision in a second vessel;
C) fastening a mounting structure to each vessel adjacent to each incision; and
D) shaping said mounting structure to define a desired flow area and shape for the junction of the two vessels.

14. A method of performing an anastomosis comprising: maintaining blood flow in a vessel; defining an incision in the vessel; fastening a stent on the outside of the vessel; and shaping the stent.

15. The method defined in claim 14 further including stabilizing the vessel during the step of fastening the stent.

16. The method defined in claim 14 further comprising steps of performing multiple grafts.

* * * * *